United States Patent [19]
Yoon et al.

[11] Patent Number: 5,696,134
[45] Date of Patent: Dec. 9, 1997

[54] IRREVERSIBLE HIV PROTEASE INHIBITORS, INTERMEDIATES, COMPOSITIONS AND PROCESSES FOR THE PREPARATION THEREOF

[75] Inventors: Heungsik Yoon; Nakyen Choy; Sung Chun Kim; Ho Il Choi; Young Chan Son; Chi Hyo Park; Kwang-Yul Moon; Wonhee Jung; Chung Ryeol Kim; Chang Sun Lee, all of Daejeon; Jong Sung Koh, Seoul; Sang Soo Kim, Daejeon, all of Rep. of Korea

[73] Assignee: LG Chemical Limited, Seoul, Rep. of Korea

[21] Appl. No.: 473,877

[22] Filed: Jun. 7, 1995

Related U.S. Application Data

[63] Continuation-in-part of Ser. No. 341,352, Nov. 17, 1994, abandoned, which is a continuation-in-part of Ser. No. 159,382, Nov. 30, 1993, Pat. No. 5,587,388.

[30] Foreign Application Priority Data

Jun. 15, 1994 [KR] Rep. of Korea .................. 94-13423

[51] Int. Cl.$^6$ .................. A61K 31/44; A61K 31/47
[52] U.S. Cl. .................. 514/314; 514/326; 514/475; 530/331
[58] Field of Search .................. 546/169, 175; 530/331; 549/525, 556; 568/27, 28, 30, 39, 44, 45, 59, 62, 67, 69, 75; 514/277, 307, 311, 438, 448, 460, 461, 475, 618, 619, 624, 709, 716, 718, 747, 751, 753, 314, 326

[56] References Cited

FOREIGN PATENT DOCUMENTS

| 575097 A1 | 12/1993 | European Pat. Off. |
| 601486 A1 | 6/1994 | European Pat. Off. |

Primary Examiner—Margaret Einsmann
Assistant Examiner—John R. Hardee
Attorney, Agent, or Firm—Anderson Kill & Olick, P.C.

[57] ABSTRACT

Novel cis-epoxide compounds of formula (I) are useful for treating or preventing diseases caused by HIV infection:

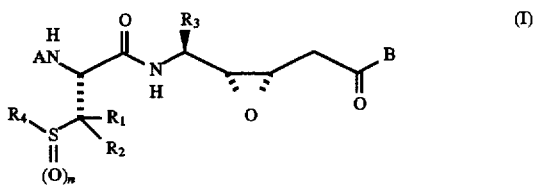

wherein A, B, $R_1$ to $R_4$ and n have the same meanings as defined in the specification.

The novel HIV protease inhibitor of the formula (I) has a specific structure to form a stable bonding with the enzyme active site, which entails a highly enhanced irreversible inhibition against HIV protease.

14 Claims, 1 Drawing Sheet

IRREVERSIBLE HIV PROTEASE INHIBITORS, INTERMEDIATES, COMPOSITIONS AND PROCESSES FOR THE PREPARATION THEREOF

CROSS REFERENCE TO RELATED APPLICATIONS

This application is a continuation-in-part application of U.S. Ser. No. 08/341,352 filed on Nov. 17, 1994, now abandoned which is in turn a continuation-in-part application of U.S. Ser. No. 08/159,382 filed on Nov. 30, 1993, now U.S. Pat. No. 5,587,388.

FIELD OF THE INVENTION

The present invention relates to novel compounds for inhibiting human immunodeficiency virus ("HIV") protease, their intermediates, pharmaceutical compositions containing the compounds as active ingredients, and processes for preparing the compounds and the intermediates.

BACKGROUND OF THE INVENTION

HIV, which is known to cause AIDS(acquired immunodeficiency syndrome), is one of retroviruses which contain their genetic information in RNA; and consists of a core, envelope proteins, a lipid membrane and glycoproteins. The HIV core comprising two single-stranded RNA and reverse transcriptase is enclosed by envelope proteins such as p17, p9,p24, p7 and the like, which are in turn enclosed by a lipid membrane. Glycoproteins located outside of the lipid membrane consist of gp41 and gp120, of which gp120 plays a major role to recognize and infect T cells.

Similar to other retroviruses, HIV is unusual in that its growth cycle has a stage in which the flow of information is reversed(that is, RNA→DNA) contrary to the usual mechanism (DNA→RNA). For such a reverse mechanism, existence of a reverse transcriptase which makes double-stranded DNA from a single-stranded RNA template is essential; and, consequently, only retroviruses have a reverse transcriptase.

Accordingly, it has been predicted that HIV can be incapacitated by way of inhibiting the activity of the reverse transcriptase; and, hitherto, many reverse transcriptase inhibitors have been developed. Such inhibitors include: 3-azido-3'-deoxythymidine(AZT) developed by Burrows-Wellcome Co.; 2', 3'-dideoxyinosine(DDI) of Bristol Meyers Squibb Co; and 2', 3'-dideoxycytosine(DDC) of F. Hoffmann-La Roche AG.

However, the above and other compounds known in the art as a treating agent for AIDS have shown rather limited effects of prolonging a patient's life; and, further, tend to cause serious side effects such as decrease in the number of blood platelets, kidney infection, bone marrow toxicity, and the like.

Another important enzyme active during HIV replication is the HIV protease responsible for the proteolytic processing of polyprotein precursors. Gag protein(p55) and gag-pol protein (p165) are processed into structural envelope proteins and essential functional proteins for HIV replication such as protease, reverse transcriptase, integrase, etc. (see Henderson et al., *J. Virol.*, 62, 2587(1988)). Accordingly, HIV protease inhibitors have been also considered as a potential AIDS treating agent.

The HIV protease is present in a dimeric form having a $C_2$ symmetry; and, each monomer has a molecular weight of 10,100 daltons and consists of 99 amino acids. The HIV protease is classified as an aspartic protease since it is proven to have the typical sequence of Asp-Thr-Gly at an active site, and can be inhibited by pepstatin, a known inhibitor of aspartic proteases. Pepstatin has a hydroxyethyl group instead of a peptide bond at the site where reaction with a protease occurs, which is similar to the form of a transition state during the protease reaction; and, it appears that the transition form having a hydroxyethyl group binds to a protease more strongly than a polypeptide having a peptide bond, thereby allowing the pepstatin to prohibit the protease reaction.

Consequently, recent studies on HIV protease inhibitors have been focused on the development of compounds similar to the transition state which has a high affinity to the protease (see Roberts et al., *Science*, 248, 358(1990); Signal et al., EP Publication No. 0337714; Handa et al., EP Publication No. 0346847; Desolms et al., EP Publication No. 0356223; Dreyer et al., EP Publication No. 0352000; Signal et al., EP Publication No. 0357332; Hanko et al., EP Publication No 0361341; Kempf et al., Korean Patent Laid-open Publication No. 90-18134; Bone et al., *J. Am. Chem. Soc.*, 113, 9382(1991); and Urban et al., *FEBS Letter*, 298, 9(1992)).

These compounds are, however, reversible inhibitors, which are less effective than an irreversible inhibitor as the latter can block the protease activity permanently. Accordingly, efforts have been made for the development of irreversible inhibitors by way of introducing an epoxide to the reaction site thereof (see Moelling et al., *FEBS Letter*, 261, 373(1990); Pal et al., *Proc. Natl. Aca. Sci.*, 85, 9283 (1988); Grant et al., *Bioorg. Med. Chem. Letter*, 2, 1441 (1992); and EP Publication No. 0492136A). However, these irreversible inhibitors are found to have a too limited inhibitory effect to be useful as an AIDS treating agent.

SUMMARY OF THE INVENTION

Accordingly, it is a primary object of the present invention to provide irreversible HIV protease inhibitors having a high inhibitory effect against HIV protease, useful for the treatment of AIDS.

Another object of the present invention is to provide novel compounds useful as intermediates for preparing the inhibitors.

A further object of the present invention is to provide processes for preparing said inhibitors and intermediates.

A still another object of the present invention is to provide pharmaceutical compositions containing the inhibitors in a therapeutically effective amount as active ingredients, and pharmaceutically acceptable carriers.

In accordance with one aspect of the present invention, there is provided a novel cis-epoxide compound of formula (I) and the pharmacologically acceptable salts, hydrates and solvates thereof:

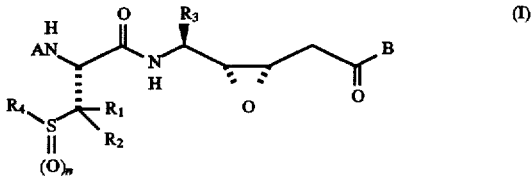

wherein:

$R_1$ and $R_2$ are independently a hydrogen or a lower alkyl group;

$R_3$ is an aryl group or a lower alkyl group optionally substituted with an aromatic radical or a $C_3$–$C_8$ cyclic alkyl radical;

$R_4$ is a hydrogen or a $C_1$–$C_4$ alkyl group;

n is 0, 1 or 2;

A is a group of the formula $(X)(Y)_mR_5$ (wherein X is —CO, —COCO, —SO, —SO$_2$ or —CS; Y is —O—, —CH$_2$—, —NH— or —NCH$_3$—; m is 0 or 1; and $R_5$ is a heterocycle, a straight, branched or cyclic $C_1$–$C_8$ alkyl radical, or a lower alkyl radical substituted with a heterocycle or cyclic alkyl substituent, or a straight, branched or cyclic $C_1$–$C_8$ alkoxy radical, or an aryl-substituted lower alkoxy radical), or a group of the formula $NR_6R_7$ (wherein $R_6$ is a straight or branched $C_1$–$C_8$ alkyl radical, or a cyclic alkyl radical, or a lower alkyl radical substituted with a cyclic alkyl substituent; and $R_7$ is a hydrogen or a lower alkyl radical); and B is a group of the formula

wherein Z is O, NH or NCH$_3$; and $R_8$ and $R_9$ are independently a lower alkyl radical optionally substituted with an aromatic hydrocarbon or cyclic alkyl substituent, or a $C_3$–$C_8$ cyclic alkyl radical, or an aromatic radical).

DETAILED DESCRIPTION OF THE INVENTION

Figure 1:
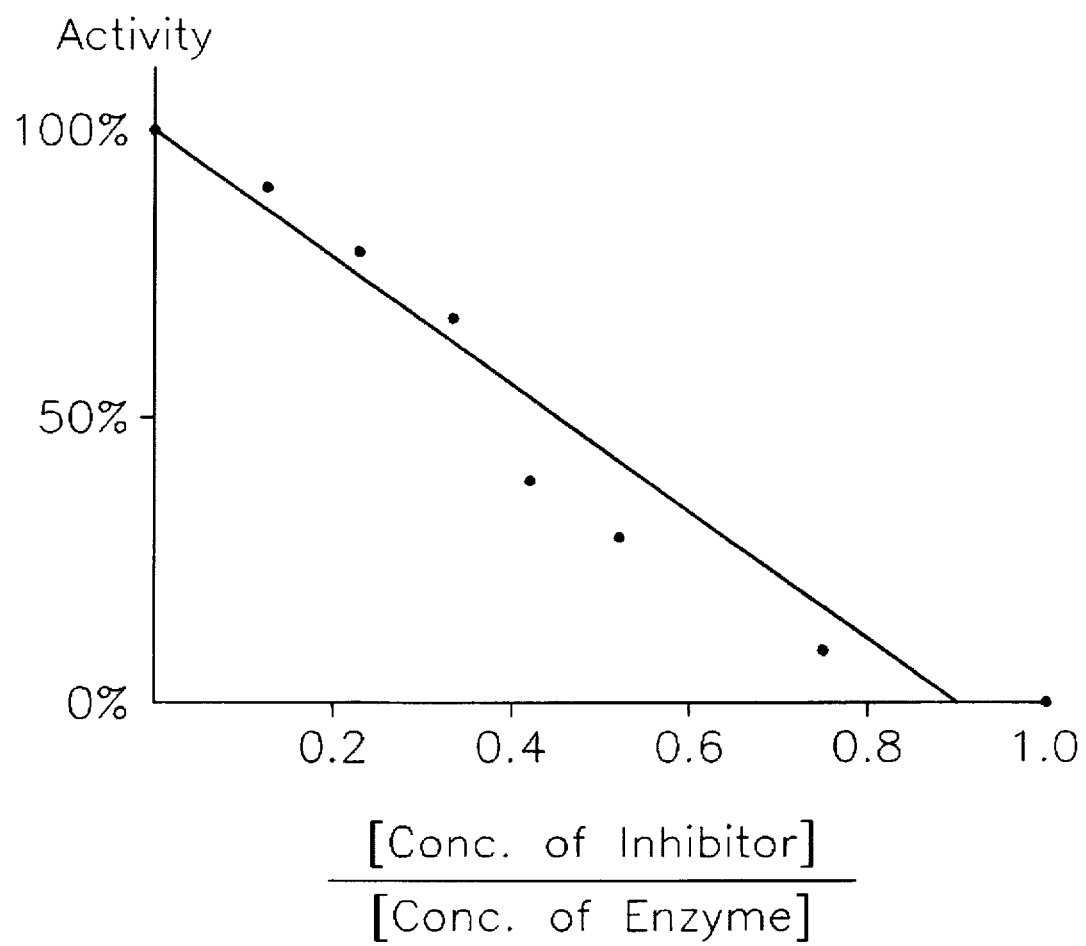
FIG. 1 is a graph representing the stoichiometric ratios of the novel inhibitors over the enzyme for the inactivation of the latter.

The novel HIV protease inhibitor of the present invention has a specific structure to form a stable bonding with an enzyme active site, which entails a highly enhanced irreversible inhibition against HIV protease. That is, in accordance with the present invention, a group having the ability to form a hydrogen bond around the epoxide group of the inhibitor is introduced so as to greatly enhance the irreversible inhibition of the inhibitor.

Among the compounds of formula(I) of the present invention, preferred are the compounds of formula(I-1):

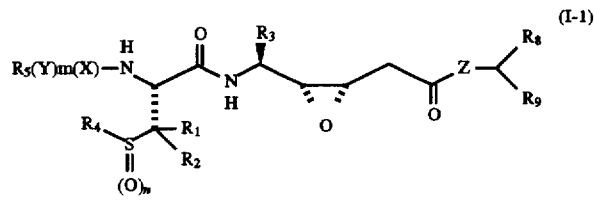

wherein:

$R_1$ and $R_2$ are independently a hydrogen, or a methyl or ethyl group;

$R_3$ is an isobutyl, cyclopentylmethyl, cyclohexylmethyl, benzyl or phenyl group;

$R_4$ is a hydorogen, or a methyl or ethyl group;

$R_5$ is a cyclohexylmethyl, benzyl, quinolinyl, tetrahydroquinolinyl, isoquinolinyl, indolyl, pyridyl, pyridylmethyl, isoquinolinyloxymethyl, naphtoxymethyl, tetrahydropyranyl, benzopyranyl, or 4-oxo-4H-1-benzopyranyl group;

$R_8$ and $R_9$ are independently an isopropyl, isobutyl, isopentyl, benzyl, cyclopropyl, cyclobutyl, cyclopentyl, cyclopropylmethyl, or phenyl group; and X, Y, Z, m and n have the same meanings as defined in formula(I).

Among the compounds of formula(I), also preferred are the compounds of the following formula(I-2):

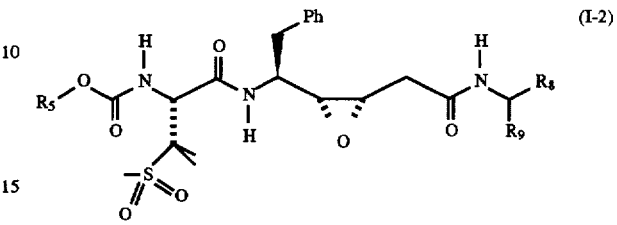

wherein:

$R_5$ is a straight or branched $C_1$–$C_8$ alkyl group, a lower alkyl group substituted with a heterocycle or cyclic alkyl radical, or a cyclic alkyl group; and $R_8$ and $R_9$ have the same meanings as defined in formula (I).

Among the compounds of formula(I-2), more preferred are those wherein:

$R_5$ is an isopropyl or cyclopropylmethyl group;

$R_8$ is an isopropyl group; and $R_9$ is a benzyl group.

Among the compounds of formula(I), similarly preferred are the compounds of the following formula (I-3):

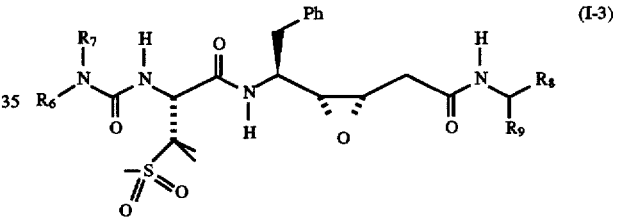

wherein:

$R_6$, $R_7$, $R_8$ and $R_9$ have the same meanings as defined in formula(I).

Among the compounds of formula(I-3), more preferred are those wherein:

$R_6$ is a 2-furanylmethyl or benzyl group;

$R_7$ is a hydrogen or a methyl group;

$R_8$ is a benzyl group; and $R_9$ is an isopropyl group.

Among the compounds of formula(I), equally preferred are the compounds of the following formula (I-4):

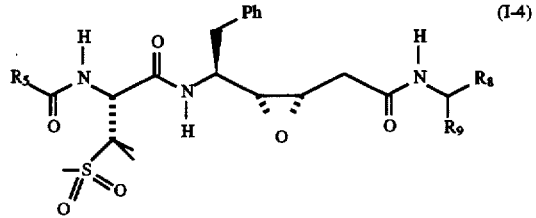

wherein:

$R_5$ is a cyclic $C_1$–$C_8$ alkyl group, or a heterocycle; and $R_8$ and $R_9$ have the same meanings as defined in formula (I).

Among the compounds of formula(I-4), more preferred are those wherein:

$R_5$ is a 2-thiophene, 2-furanyl or 4-oxo-2,3-dihydro-6,6-diphenylpyran group;

$R_8$ is an isopropyl group; and $R_9$ is a benzyl group.

Among the compounds of formula(I), also preferred are the compounds of the following formula (I-5):

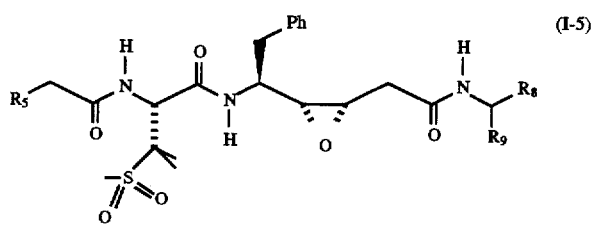

wherein:

$R_5$ is a straight, branched or cyclic $C_1$–$C_8$ alkyl group, a straight, branched or cyclic $C_1$–$C_8$ alkoxy group, an aryl-substituted lower alkoxy group, or a heterocycle; and $R_8$ and $R_9$ have the same meanings as defined in formula (I).

Among the compounds of formula(I-5), more preferred are those wherein:

$R_5$ is 3-thiophene;

$R_8$ is an isopropyl group; and $R_9$ is a benzyl group.

On the other hand, the present invention encompasses, within its scope, novel cis-epoxide compounds of formula (II) and the pharmacologically acceptable salts, hydrates and solvates thereof:

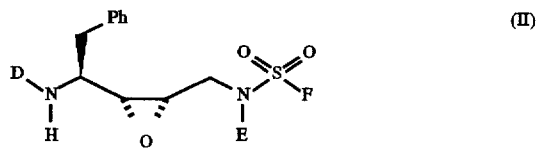

wherein:

D is a group having the formula

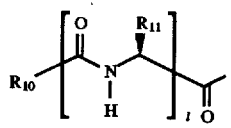

(wherein $R_{10}$ is a lower alkoxy radical optionally substituted with an aromatic hydrocarbon, or a nitrogen-containing aromatic radical; $R_{11}$ is a lower alkyl radical optionally substituted with an amide; and l is 0, 1 or 2);

E is a hydrogen, or a lower alkyl group optionally substituted with an aromatic radical; and F is a lower alkyl group optionally substituted with an aromatic radical, a lower alkoxy group, or a group having the formula

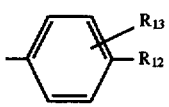

(wherein $R_{12}$ and $R_{13}$ are independently a hydrogen, a lower alkyl radical, OH, or $NH_2$).

Among the compounds of formula(II), preferred are those wherein:

$R_{10}$ is 2-quinoline;

$R_{11}$ is an asparagine residue;

l is 1;

E is a hydrogen; and

F is a p-methylphenyl or p-aminophenyl group.

As used in this specification, the following terms shall have the following respective meanings:

The term "lower alkyl" refers to a $C_{1-4}$ straight or branched alkyl including methyl, ethyl, isopropyl, isobutyl and t-butyl, preferably, methyl.

The term "lower alkyl or alkoxy substituted with an aromatic radical" means lower alkyl or alkoxy, preferably, $C_{1-2}$ alkyl or alkoxy, substituted with an aromatic radical, preferably, benzyl, at the end carbon position of a straight chain.

The term "nitrogen-containing aromatic radical or group" refers to a monocyclic or bicyclic aromatic radical containing 1 to 3 nitrogen atoms in the ring, inclusive of, e.g., pyridine, quinoline, quinoxaline and benzimidazole, and preferably, quinoline.

The term "heterocycle" refers to a triangular or hexagonal radical containing 1 to 3 heteroatoms such as oxygen, nitrogen and sulfur atoms in the ring, wherein the nitrogen and sulfur atoms may be oxidized; and encompasses a bicycle wherein it is bonded with a benzene, cyclohexane or other heterocycle. Representative examples of the heterocycle include pyrol, pyrolinyl, pyrolidinyl, pyrazoyl, pyrazolinyl, pyrazolidinyl, imidazoline, imidazolinyl, imidazolidinyl, pyridyl, piperidinyl, pyrazinyl, piperazinyl, pyrimidinyl, pyridazinyl, oxazoyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, tetrahydroquinolinyl, isoquinolinyl, benzimidazoylyl, benzithiazoylyl, benzoxazoyl, benzoperfuranyl, furyl, dihydrofuranyl, tetrahydrofuranyl, dioxanyl, dioxolinyl, thienyl, benzothianyl and benzothiranyl.

The term "aryl" means a monovalent monocyclic or bicyclic aromatic radical, for example, phenyl and naphthalene.

The term "aryl-substituted lower alkyl" refers to a lower alkyl substituted with an aryl or arylalkoxy including phenoxy and naphtoxy, preferably, benzyl.

The term "amino acid" means, among other things, asparagine, valine, threonine, isoleucine and glutamic acid, preparably.

In this specification, standard three letter abbreviations are used to represent amino acids. The meanings of these abbreviations can be found in, for example, *Eur. J. Biochem.*, 158, 9–31(1984).

Important compounds of the present invention are listed in Table 1 below.

TABLE 1
| Comp. No. | Structure |
|---|---|
| 1 | 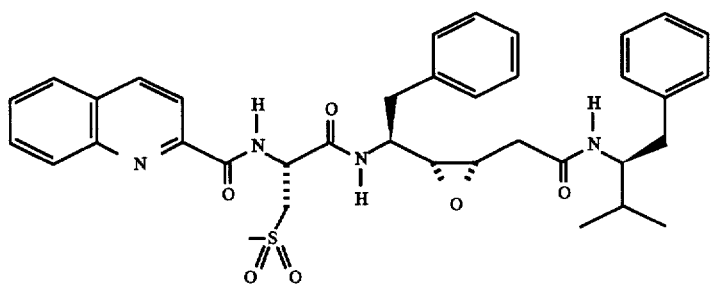 |
| 2 | 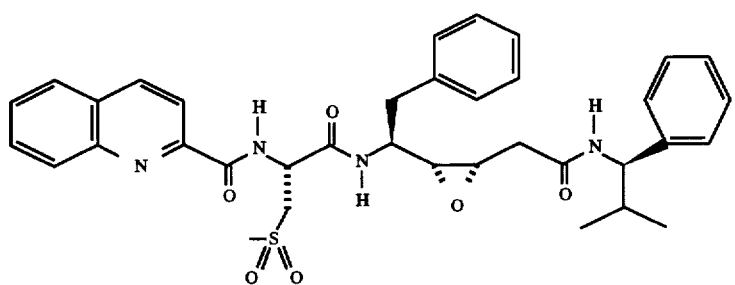 |
| 3 | 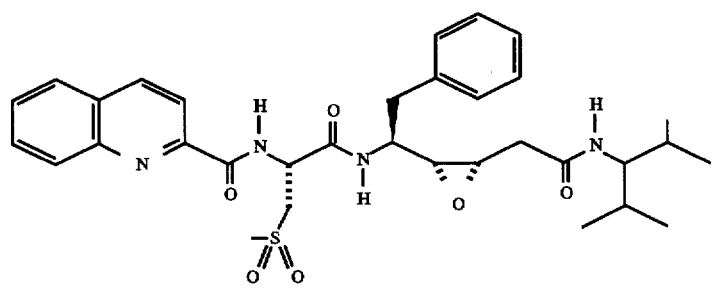 |
| 4 | 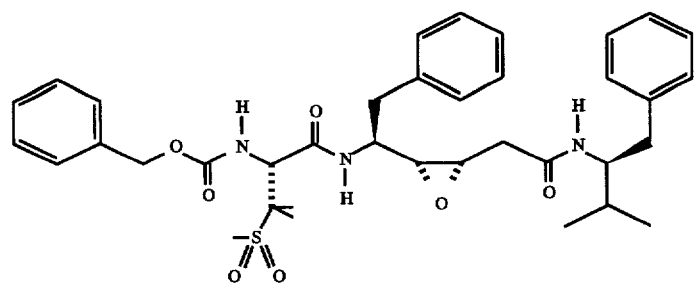 |
| 5 | 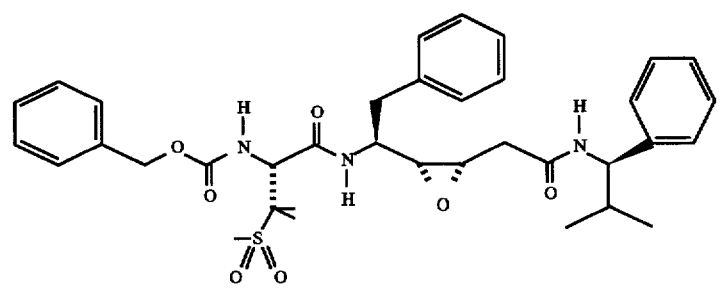 |

TABLE 1-continued
| Comp. No. | Structure |
|---|---|
| 6 | 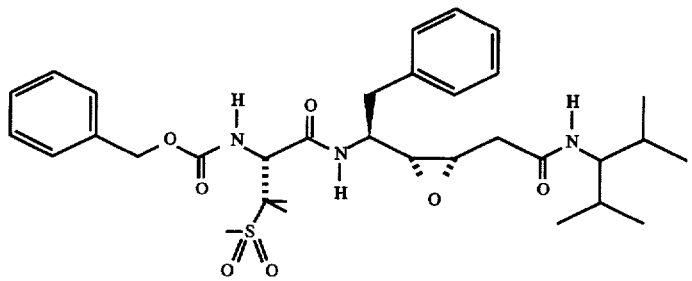 |
| 7 | 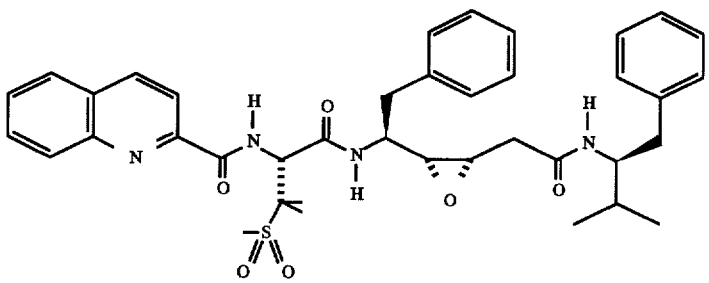 |
| 8 | 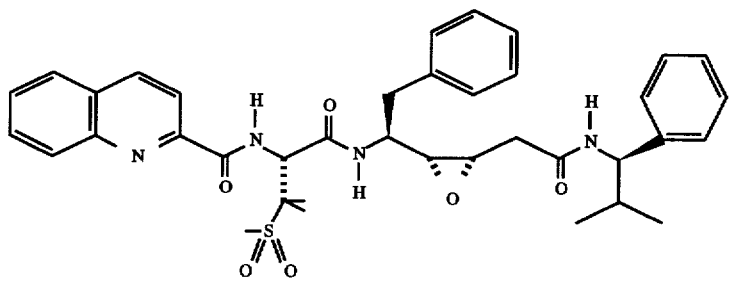 |
| 9 | 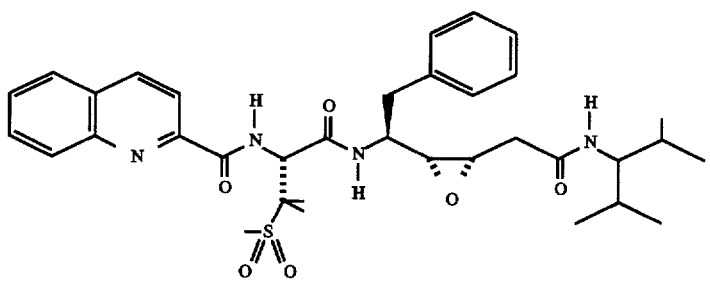 |
| 10 | 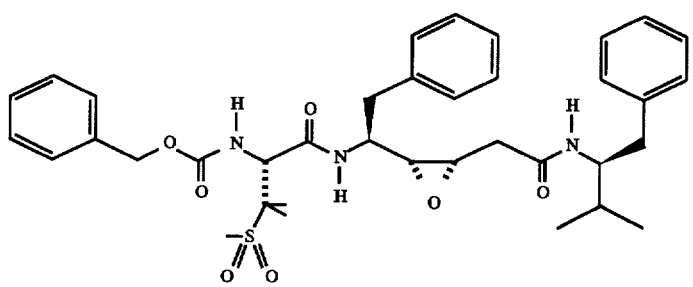 |

TABLE 1-continued
| Comp. No. | Structure |
|---|---|
| 11 | 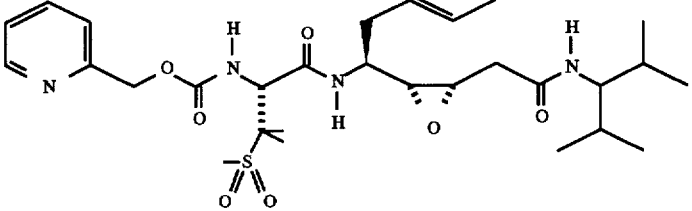 |
| 12 | 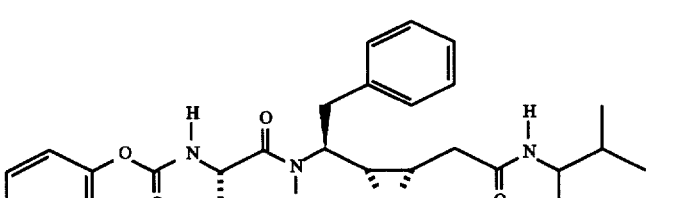 |
| 13 | 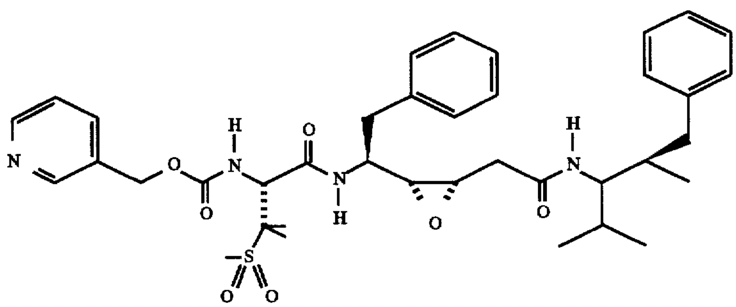 |
| 14 | 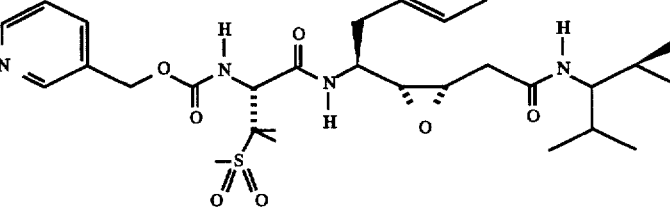 |
| 15 | 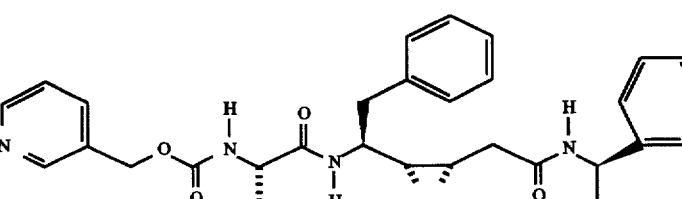 |

TABLE 1-continued

| Comp. No. | Structure |
|---|---|
| 16 | 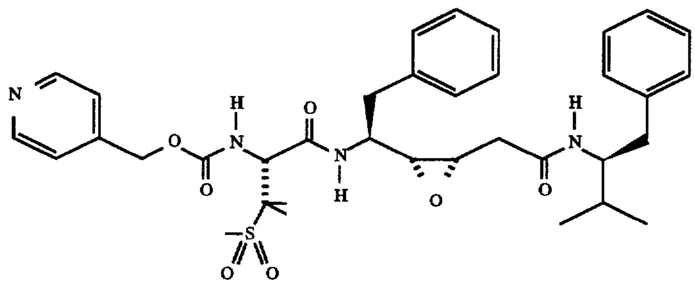 |
| 17 | 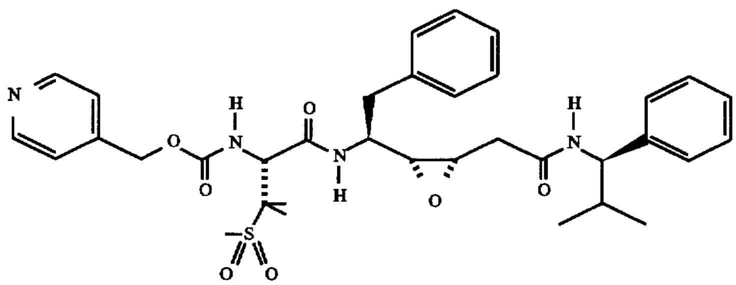 |
| 18 | 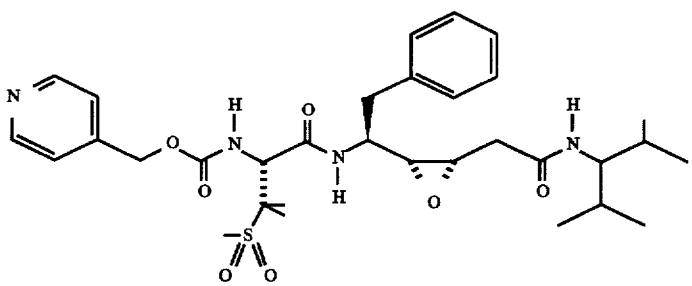 |
| 19 | 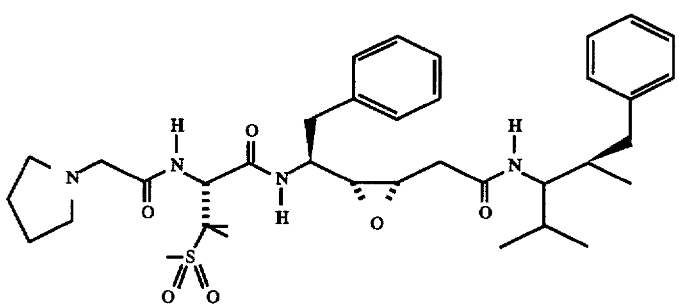 |
| 20 | 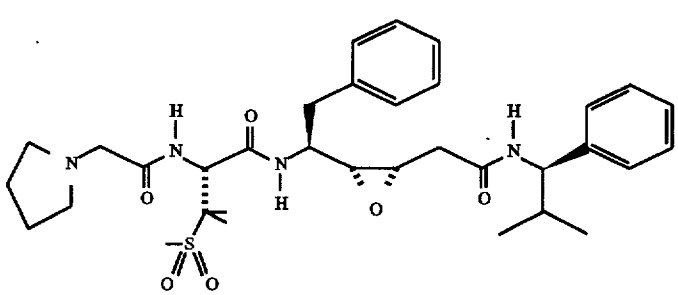 |

TABLE 1-continued
| Comp. No. | Structure |
|---|---|
| 21 | 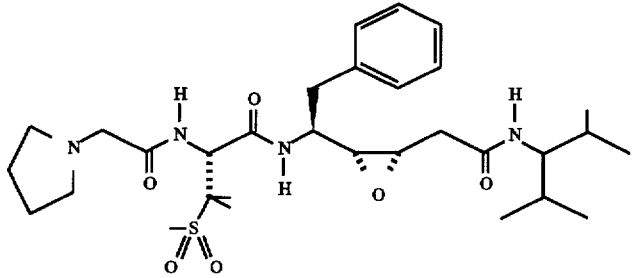 |
| 22 | 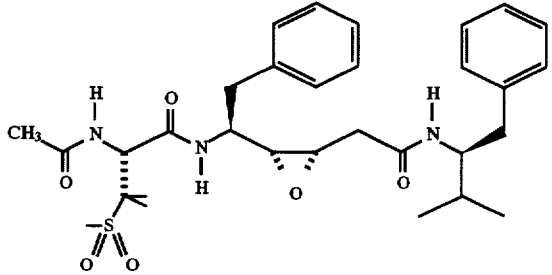 |
| 23 | 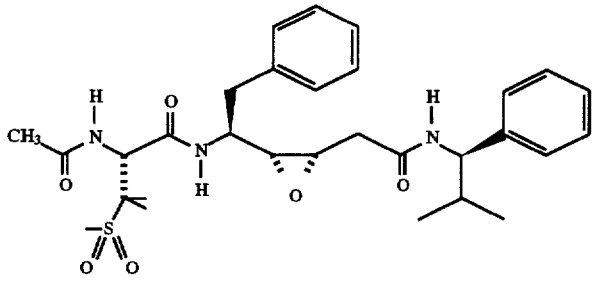 |
| 24 | 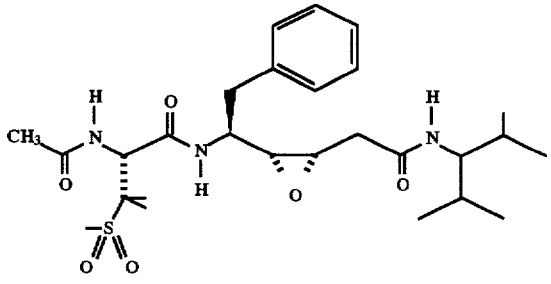 |
| 25 | 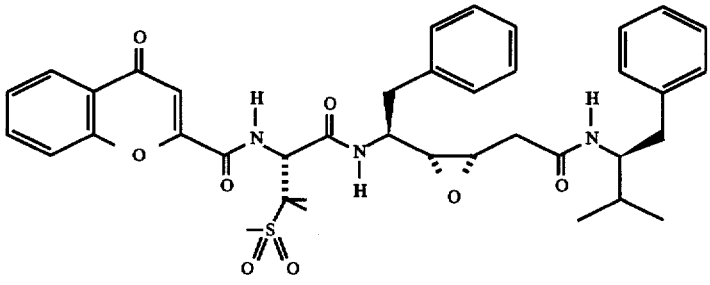 |

TABLE 1-continued
| Comp. No. | Structure |
|---|---|
| 26 | 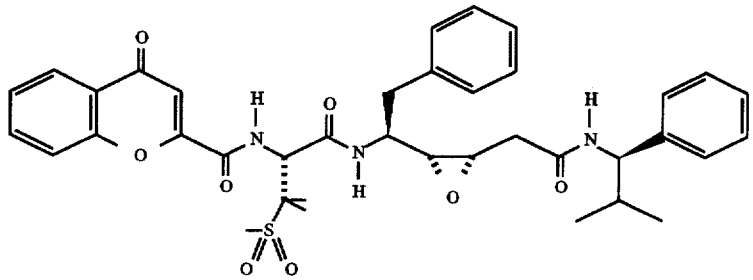 |
| 27 | 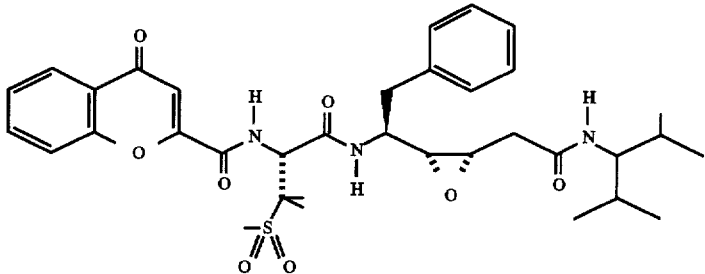 |
| 28 | 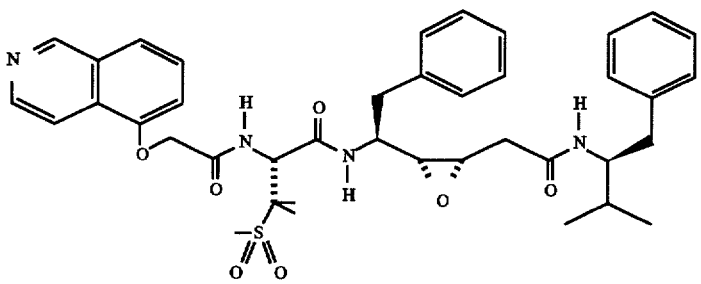 |
| 29 | 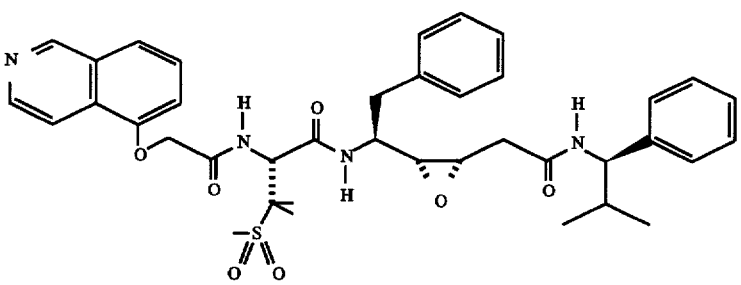 |
| 30 | 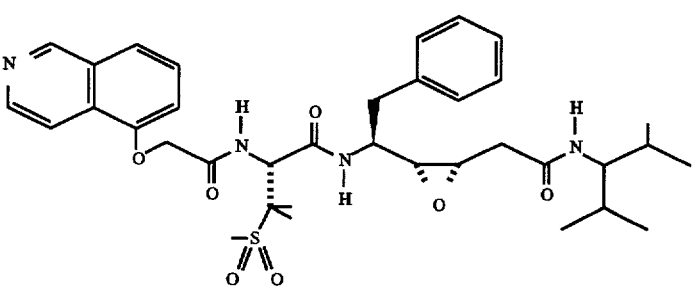 |

TABLE 1-continued
| Comp. No. | Structure |
|---|---|
| 31 | 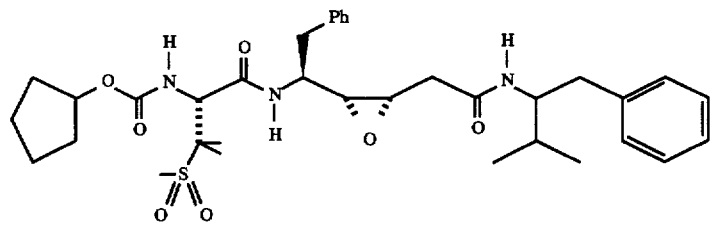 |
| 32 | 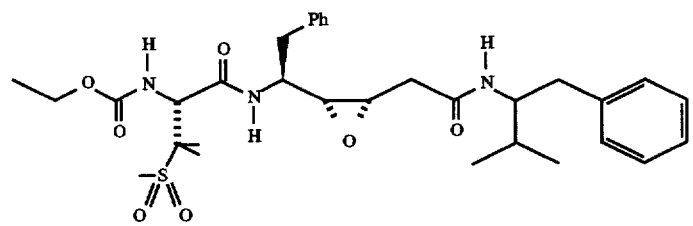 |
| 33 | 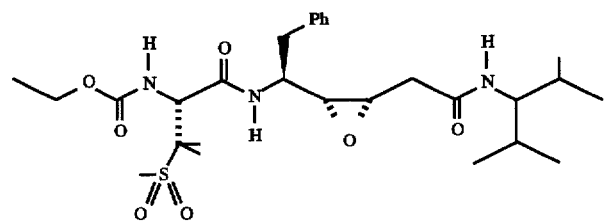 |
| 34 | 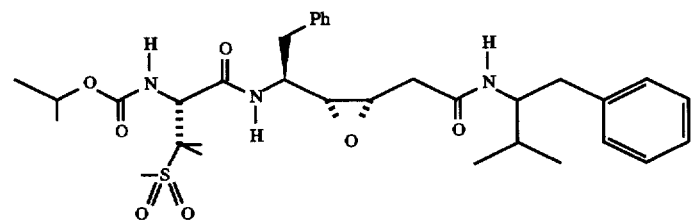 |
| 35 | 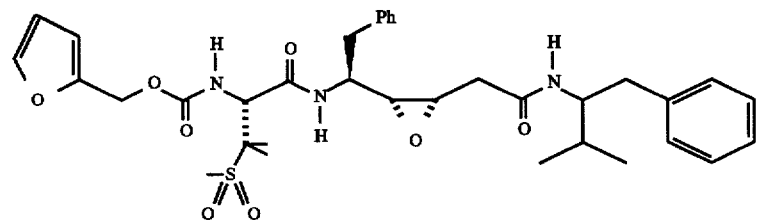 |
| 36 | 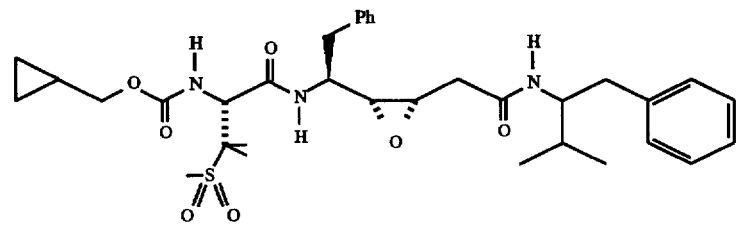 |

TABLE 1-continued
| Comp. No. | Structure |
|---|---|
| 37 | 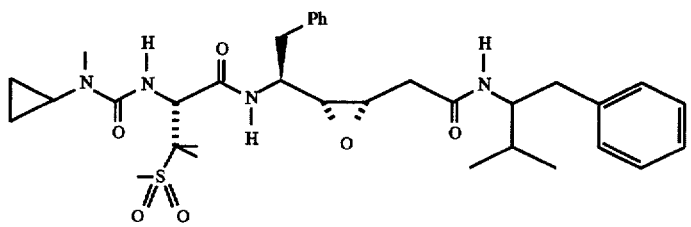 |
| 38 | 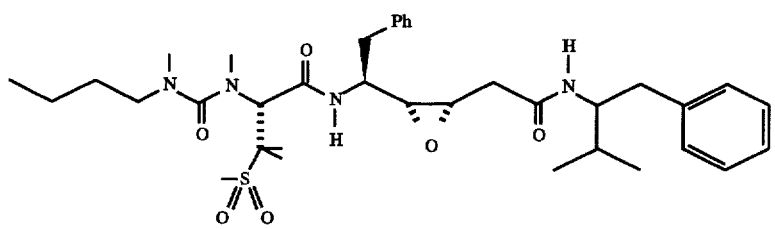 |
| 39 | 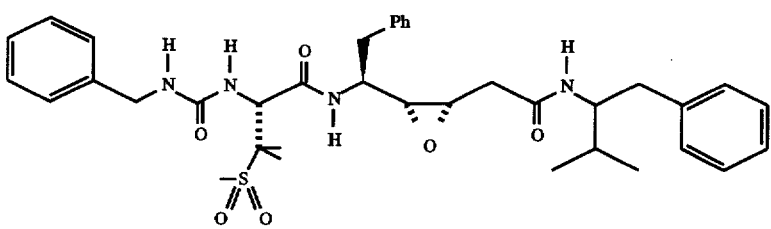 |
| 40 | 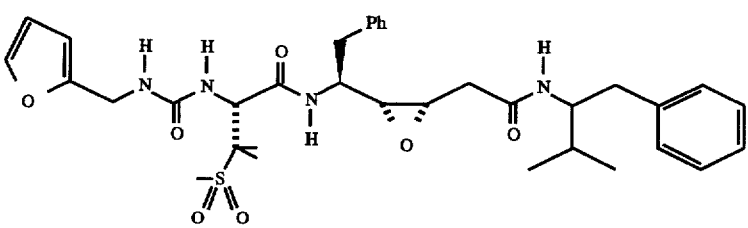 |
| 41 | 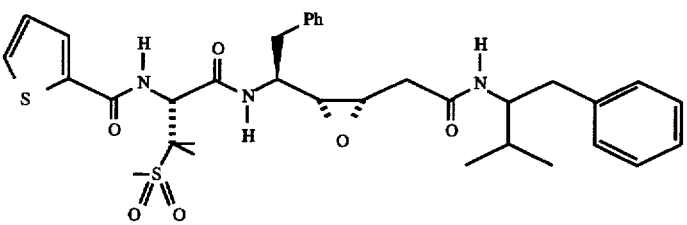 |
| 42 | 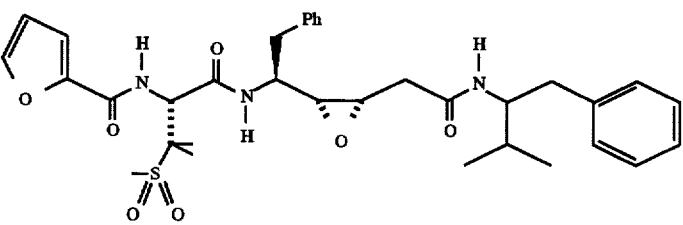 |

TABLE 1-continued
| Comp. No. | Structure |
|---|---|
| 43 | 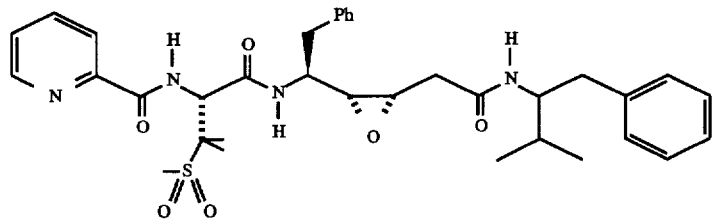 |
| 44 | 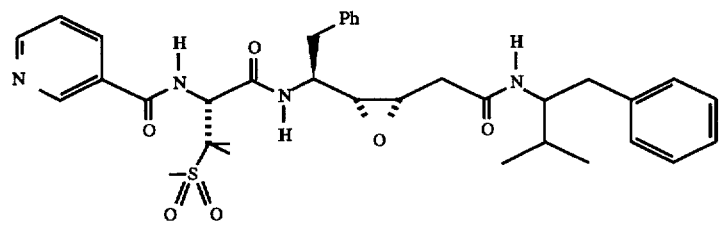 |
| 45 | 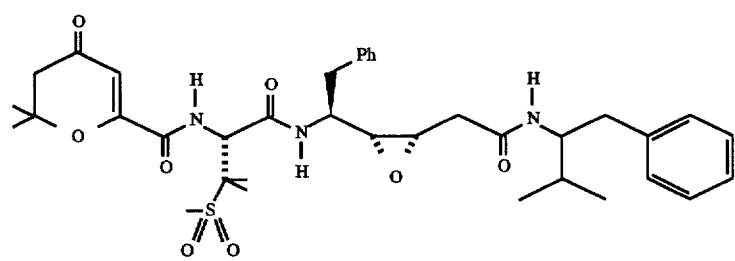 |
| 46 | 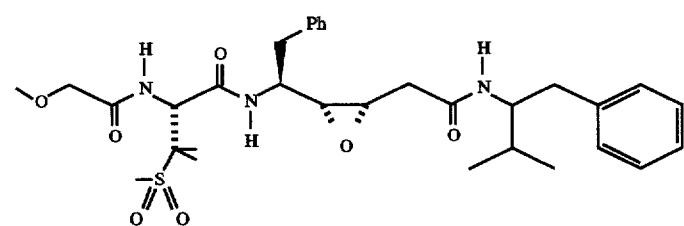 |
| 47 | 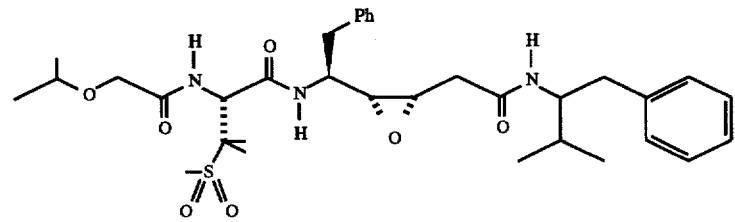 |
| 48 | 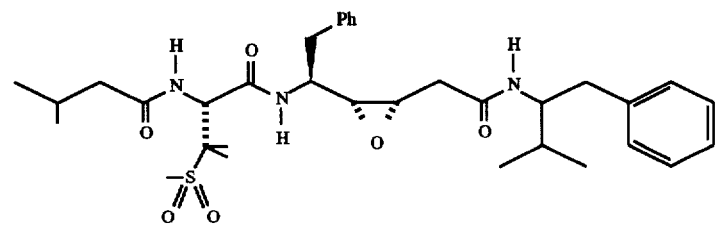 |

TABLE 1-continued
| Comp. No. | Structure |
|---|---|
| 49 | 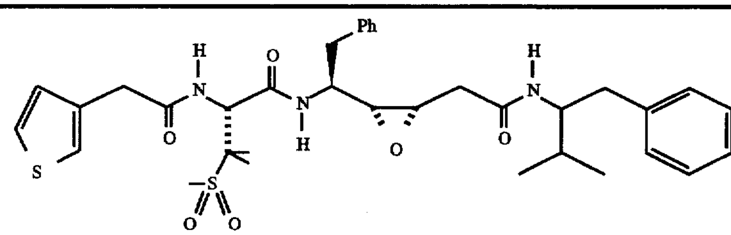 |
| 50 | 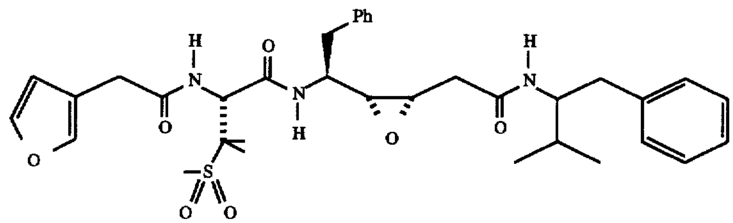 |
| 51 | 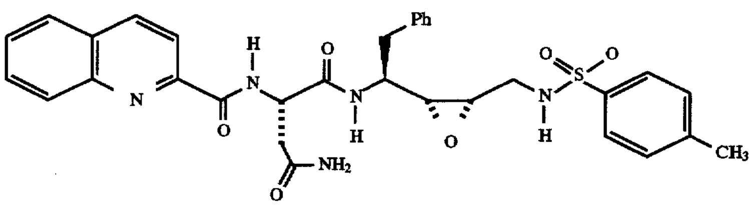 |
| 52 | 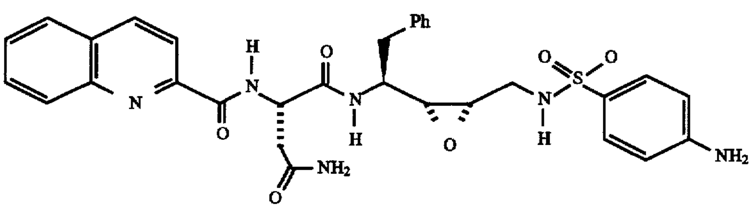 |
| 53 | 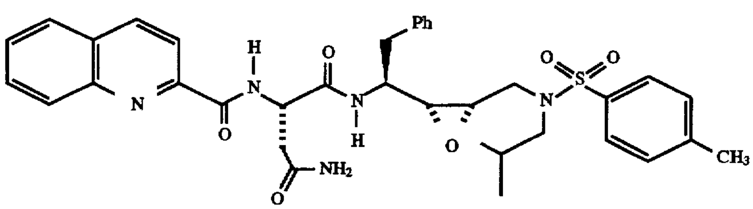 |
The cis-epoxide compounds of formula(I) of the present invention may be prepared as illustrated in the following Scheme 1.
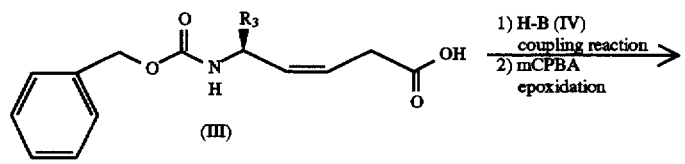
Scheme 1

-continued
Scheme 1

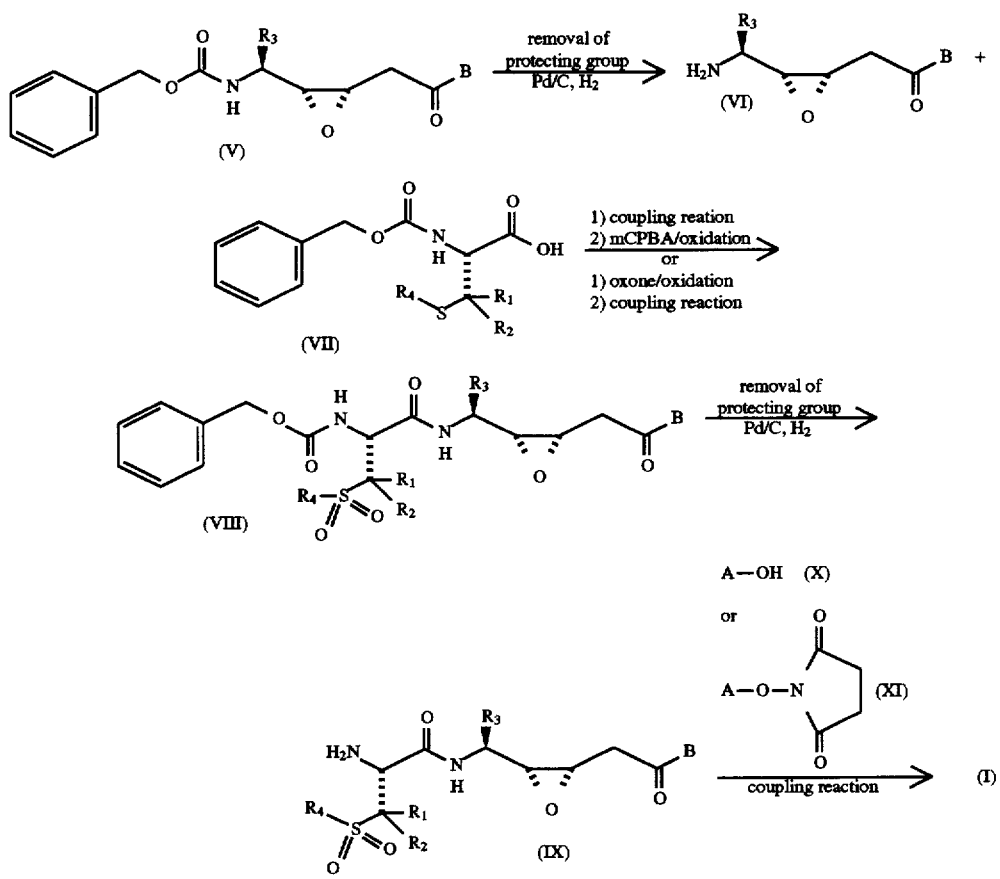

(wherein A, B and $R_1$ to $R_4$ have the same meanings as defined in formula(I)).

In the above Scheme 1, the compound of formula(III) is made to undergo a coupling reaction with the compound of formula(IV), and the resulting compound is epoxidized to give the compound of formula(V). Removal of the protecting group from the compound of formula(V) gives the compound of formula (VI). Another coupling reaction between the compound of formula(VI) and the compound of formula(VII) is carried out and the resulting compound is oxidized to give the compound of formula(VIII).

Alternatively, oxidation of the compound of formula(VII) with oxone followed by a coupling reaction between the resulting compound and the compound of formula(VI) gives the compound of formula(VIII). Deprotecting reaction of the compound of formula(VIII) gives the compound of formula (IX), which is then made to undergo a coupling reaction with the compound of formula(X) or (XI) to obtain the desired compound of formula(I).

In particular, the compounds of formula (I-2) may be prepared as illustrated in the following Scheme 2.

Scheme 2

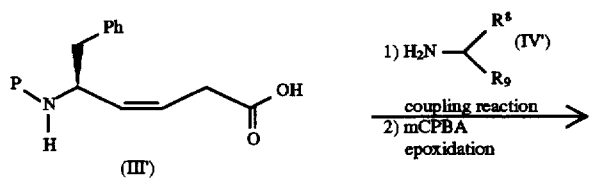

-continued
Scheme 2

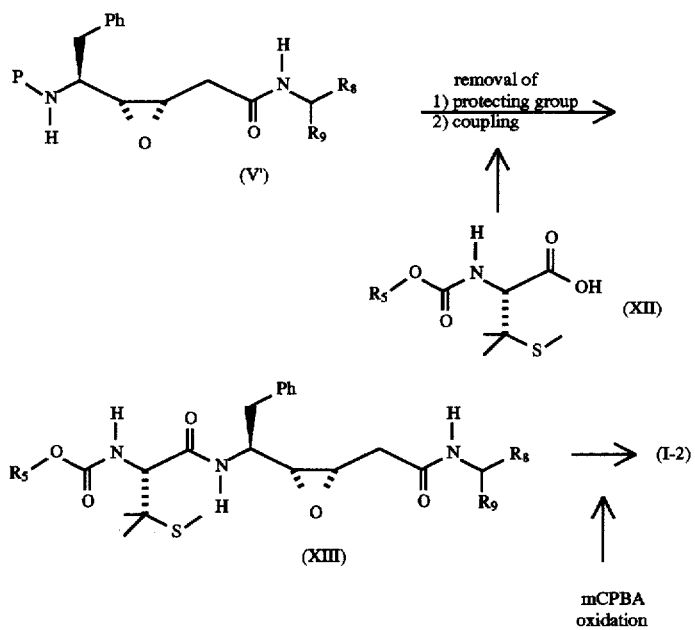

(wherein:

R$_5$, R$_8$ and R$_9$ have the same meanings as defined in formula (I-2); and

P is an amino protecting group, preferably, a benzyloxycarbonyl group).

In the above Scheme 2, the compound of formula(III') is made to undergo a coupling reaction with the compound of formula(IV'), and the resulting compound is epoxidized to give the compound of formula(V'). After removal of the protecting group from the compound of formula(V'), another coupling reaction between the deprotected compound and the compound of formula(XII) is carried out to give the compound of formula(XIII), which is then oxidized to obtain the desired compound of formula(I-2).

Further, the compound of formula(I-3) can be prepared by using the compound of following formula(XII') instead of the compound of formula(XII) in the above Scheme 2:

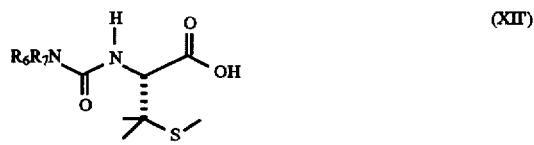

(XII')

(wherein R$_6$ and R$_7$ have the same meanings as defined in formula(I-3)).

The epoxidation reaction in the above Schemes 1 and 2 can be carried out in accordance with a known method by employing metachloroperoxybenzoic acid(mCPBA).

Further, the coupling reagents which can be used for the above coupling reactions in Schemes 1 and 2 may include, but are not limited to, dicyclohexyl carbodiimide (DCC), 3-ethyl-3'-(dimethylamino)propylcarbodiimide(EDC), bis-(2-oxo-3-oxazolidinyl)-phosphinic chloride(BOP-Cl), diphenylphosphorylazide(DPPA) and the like.

Alternatively, the coupling reactions may be carried out without any coupling reagent by employing an acyl halide or activated ester derivative. Suitable acyl halides include acyl chlorides; and, suitable activated ester derivatives are those commonly used for activating carboxylic acid groups for coupling with an amine to form an amide bond, or for coupling with an alcohol to form an ester bond including, but not limited to, anhydrides derived from alkoxycarbonyl chlorides such as methoxycarbonyl chloride, isobutoxycarbonyl chloride, and the like, carboxylic acid derived anhydrides, and, esters derived from N-hydroxybenzotriazole, N-hydroxyphthalimide, N-hydroxysuccinimide,N-hydroxy-5-norbornene-2,3-dicarboxamide, 2,4,5-trichloro-phenol and the like.

The removal of the protecting groups may be carried out in accordance with a known method in the art, depending on the kind of the protecting group involved: for instance, a benzyloxycarbonyl group can be removed in the presence of a Pd/C catalyst under a pressure of hydrogen; and a t-butoxycarbonyl group can be removed by reacting with trifluoroacetic acid.

The above compound of the formula(III), which is a useful intermediate for the preparation of the compounds of the present invention, is also novel and form another aspect of the present invention, and may be prepared in accordance with Scheme 3 given below.

Scheme 3

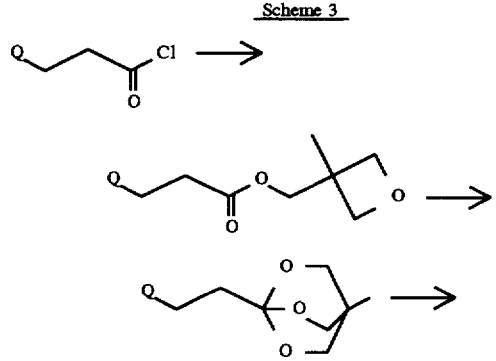

-continued
Scheme 3

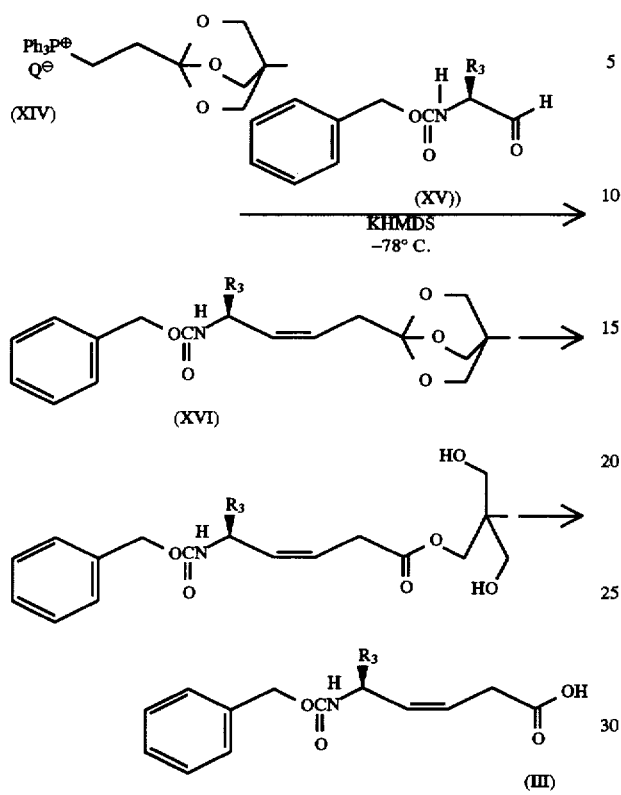

(wherein:

R³ has the same meaning as defined in Scheme 1; and
Q is a halogen such as Br or I).

As shown in Scheme 3, the compound of formula(XIV) is reacted with the compound of formula(XV) at −78° C. in the presence of potassium hexamethyldisilazane(KHMDS) to give the compound of formula(XVI), which is then heated to a reflux temperature of t-butanol in the presence of an acid catalyst in t-butanol to obtain the desired compound of formula(III).

On the other hand, a compound of formula(III') used in Scheme 2 may be prepared in accordance with the following Scheme 4.

Scheme 4

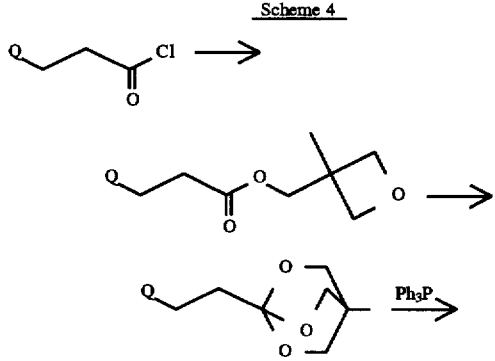

-continued
Scheme 4

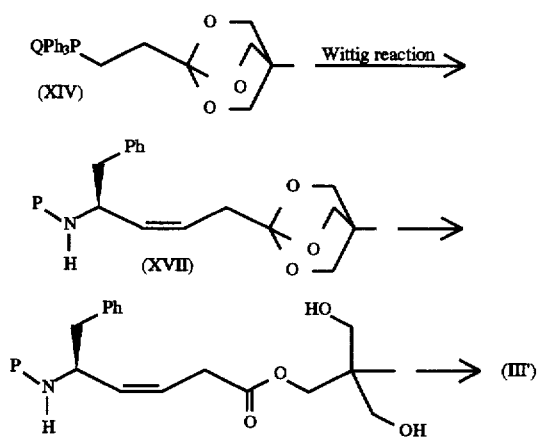

(wherein P and Q have the same meanings as defined in Schemes 2 and 3).

As shown in Scheme 4, the compound of formula(XIV) is made to undergo a Wittig reaction to give the compound of formula(XVII), which is then heated to a reflux temperature of t-butanol in the presence of an acid catalyst in t-butanol to obtain the desired compound of formula(III').

The compounds of formulae(III) and (III'), which are cis-β,γ-olefinic acids, may be prepared in accordance with a known method(see Keinan et al., Tetrahedron, 47, 4631–4638 (1991); and Corey & Shimaji, JACS, 105, 1662–1664(1983)). In the method described in the above references, an aldehyde compound, such as that of formula (XIV) in Scheme 3, is made to undergo a Wittig reaction using $K_2CO_3$ to obtain a cis-β,γ-olefinic compound, such as that of formula(III) in Scheme 3. In this case, the reaction should be carried out at a high temperature ranging from 70° to 80° C., which entails racemization of the aldehyde compound.

On the other hand, in the present invention, the Wittig reaction may be carried out at a low temperature, e.g., −78° C., by employing potassium hexamethyldisilazane (KHMDS) as a base, and therefore, the racemization is avoided.

Furthermore, in the method described in the above references, orthoesters, such as those of formulae(XVI) and (XVII) in Schemes 3 and 4 are acid-treated, and then base-treated to remove a protecting group. In this case, more than 50% of β,γ-olefinic acid is converted to α,β-olefinic acid; and, consequently, the yield of β,γ-olefinic acid decreases. Further, it is difficult to purify β,γ-olefinic acid from the mixture. On the other hand, in the present invention, said orthoesters are heated at a reflux temperature of a solvent(t-butanol, tetrahydrofuran or dioxane may be used.) in the presence of an acid catalyst, e.g., HCl , to give the β,γ-olefinic compounds of formulae(III) and (III') in a 80–90% yield.

The amines of formulae (IV) and (IV') in the above Schemes 1 and 2 may be prepared in accordance with the following Schemes 5 and 6.

Scheme 5

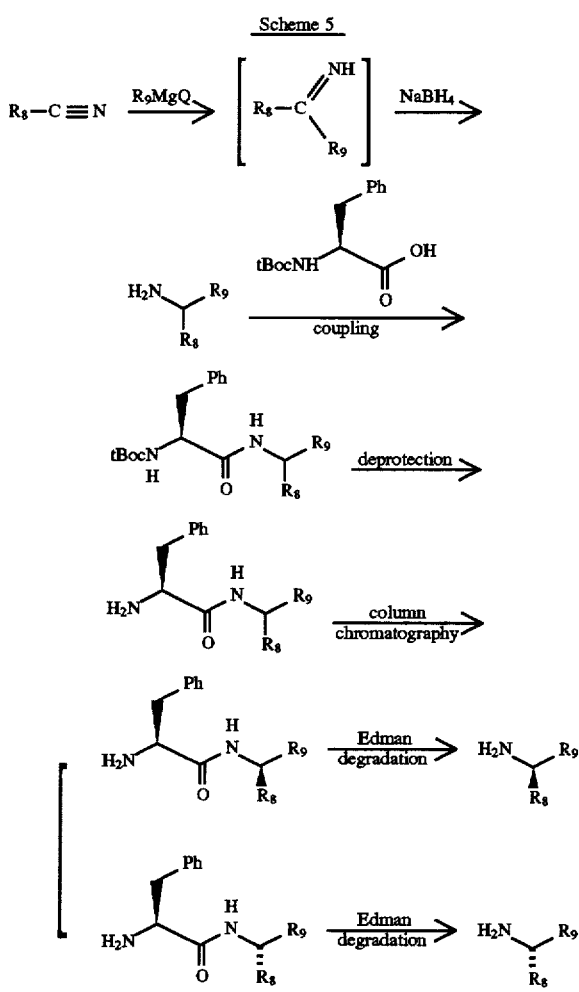

(wherein $R_8$, $R_9$ and Q have the same meaning as defined in Schemes 2 and 3).

As shown in Scheme 5, the desired amine may be prepared by a Grignard reaction and a reduction with NaBH₄ from an alkyl nitrile. In this reaction, the amine compound is produced as a racemic mixture. After the racemic mixture is coupled to t-butoxycarbonyl-L-phenylalanine and then removed t-butoxycarbonyl group therefrom, two diastereomers may be separated from each other by way of column chromatography. Each separated diastereomer is cleaved by employing Edman method to produce the desired compound.

The following Scheme 6 shows a process for preparing the optically pure amine wherein $R_8$ is an isopropyl.

Scheme 6

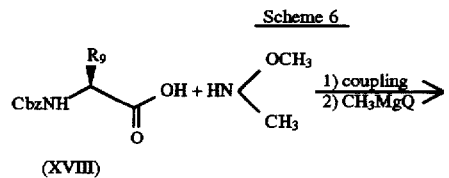

-continued
Scheme 6

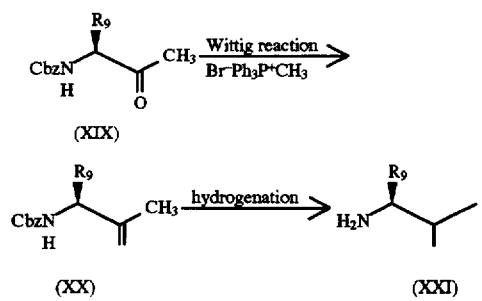

(wherein $R_9$ and Q have the same meaning as defined in Scheme 5).

In the above Scheme 6, benzyloxycarbonyl-protected L- or D-amino acid of formula(XVIII) is coupled to methoxymethyl amine, and then the coupled compound is made to undergo a Grignard reaction give the compound of formula (XIX). The compound of formula(XIX) is made to undergo a Wittig reaction at −20° C. using KHMDS as a base to give the compound of formula(XX), which is then hydrogenized to afford the desired amine compound of formula(XXI).

Further, the compound of formula(VII) which is used in the above Scheme 1 may be prepared in accordance with the following Scheme 7. In the following Scheme 7, the thiol group of a substituted cystein is methylated in the presence of a base and then the amino group is protected with benzyl chloroformate.

Scheme 7

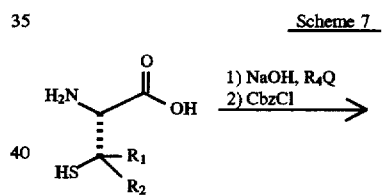

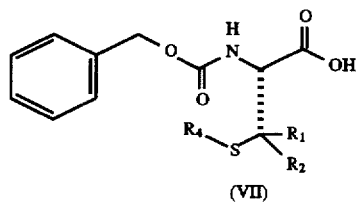

(wherein $R_1$, $R_2$, $R_4$ and Q have the same meanings as defined in Schemes 1 and 3).

The compound of formula(XII) which is used in order to prepare the compound of formula(I-2) in the above Scheme 2 may be prepared in accordance with the following Scheme 8.

Scheme 8

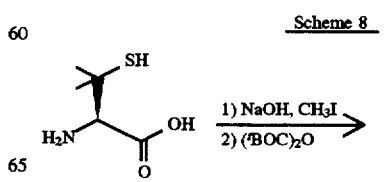

-continued
Scheme 8

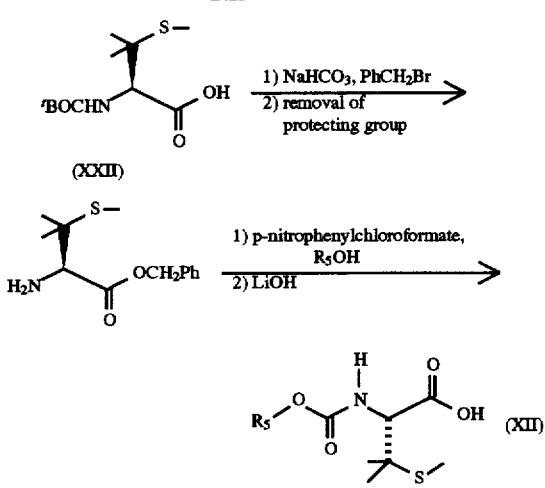

(wherein R₅ has the same meanings as defined in Scheme 2).

As shown in Scheme 8, the thiol group of L-penicilamine is methylated in the presence of a base, and the methylated compound is protected with an amino protecting group such as benzyloxycarbonyl or t-butoxycarbonyl group to give the compound of formula(XXII). The compound of formula (XXII) is esterified to a benzyl ester, the amino protecting group of which is removed. After introduction of a carbamate group thereto, the acyl protecting group is removed to give the desired compound of formula(XII).

Similarly, the compound of formula(XII') which is used in order to prepare the compound of formula(I-3) may be prepared in accordance with the following Scheme 9, that is, methylation of the thiol group of L-penicilamine, protection of the amino group, esterification to a benzyl ester, deprotection of the amino group, introduction of an urea group and deprotection of the acyl group.

Scheme 9

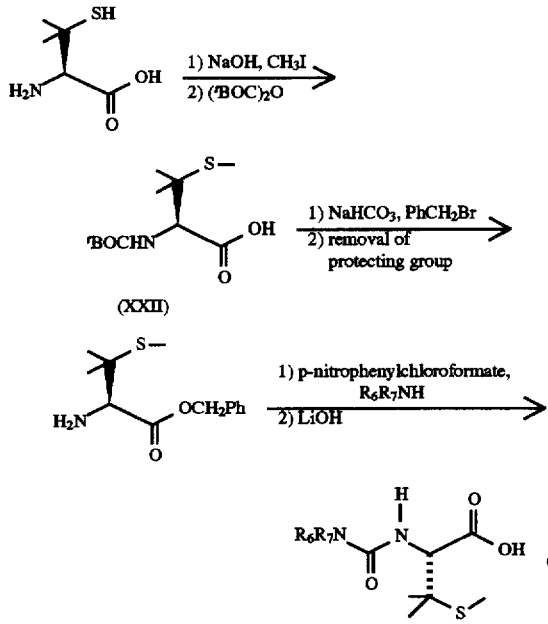

(wherein R₆ and R₇ have the same meanings as defined in formula(I-3)).

The processes for preparing carbamate and asymmetric urea through an intermediate of N-p-nitrophenyloxycarbonylamine, which is produced by the reaction of p-nitrophenylchloroformate with an amine, as shown in the above Schemes 8 and 9, are novel and form still another aspect of the present invention.

That is, the present invention further provides novel processes for preparing carbamates and asymmetric ureas which are used as intermediates in preparing the compound of formula(I).

Said process comprises reacting p-nitrophenylchloroformate with the compound of formula (XXIII) to give N-p-nitrophenyloxycarbonylamine of formula(XXIV), and then reacting the compound of formula (XXIV) directly with an amine of formula(XXV) or an alchol of formula(XXVI) to obtain an asymmetric urea of formula(XXVII) or carbamate of formula(XXVIII), respectively.

R₁₄NH₂ (XXIII)

(XXIV)
R₁₄\N(H)\C(O)\O—⟨phenyl⟩—NO₂

R₁₅R₁₆NH (XXV)

R₁₇OH (XXVI)

(XXVII)
R₁₄\N(H)\C(O)\N(R₁₅)\R₁₆

(XXVIII)
R₁₄\N(H)\C(O)\O\R₁₇ wherein:

R₁₄ is D- or L-amino acid residue, a lower alkyl group substituted with an aromatic radical, or a straight, branched or cyclic C₁-C₈ alkyl group;

R₁₅ and R₁₆ are independently a hydrogen, D- or L-amino acid residue, a lower alkyl group substituted with an aromatic radical, or a straight, branched or cyclic C₁-C₈ alkyl group; and R₁₇ is a lower alkyl group substituted with an aromatic radical, or a straight, branched or cyclic C₁-C₈ alkyl group.

On the other hand, the compound of formula(II) of the present invention may be prepared in accordance with the following Scheme 10.

Scheme 10

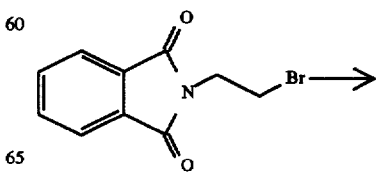

37

-continued
Scheme 10

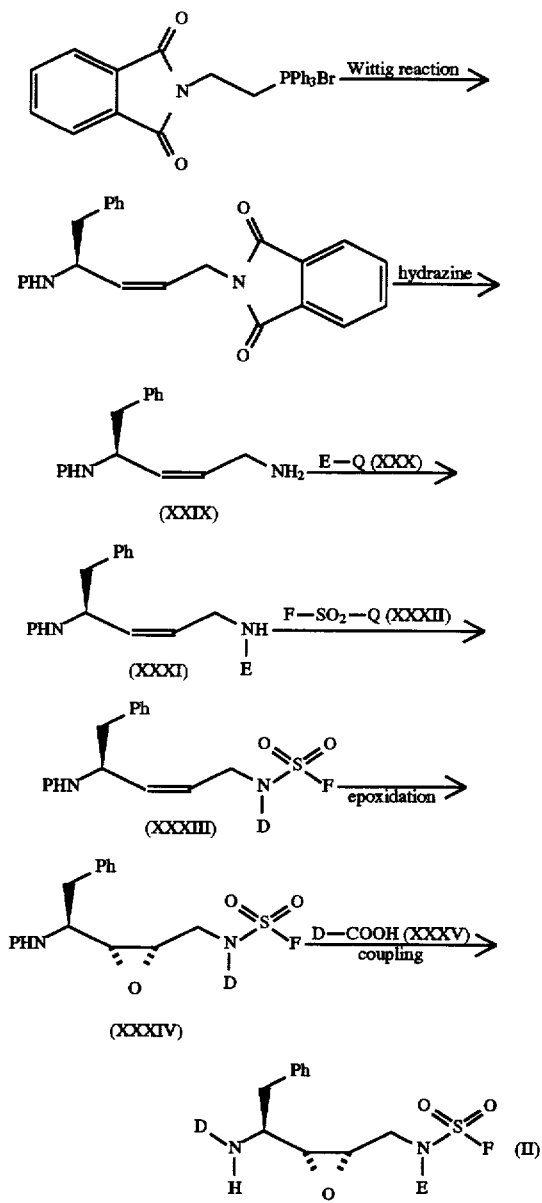

(wherein, D, E, F and Q have the same meanings as defined in formula(II) and Scheme 3).

In accordance with Scheme 10, the compound of formula (XXIX) is obtained through a Wittig reaction and deprotection with hydrazine from N-(2-bromoethyl)phthalimide. The compound of formula(XXIX) is reacted with the compound of formula(XXX) to give the compound of formula(XXXI), which is then reacted with the compound of formula (XXXII) to give the compound of formula(XXXIII). Thereafter, the compound of formula(XXXIII) is epoxidized to give the compound of formula (XXXIV), which is then deprotected. A coupling reaction between the deprotected compound and the compound of formula(XXXV) gives the desired compound of formula(II).

The compounds of the present invention may have one or more asymmetric carbons; and, therefore, the present invention encompasses, within its scope, racemic mixtures, mixtures of diastereomers, as well as single diastereomers which can be collectively represented by the formulae (I) and (II).

38

Furthermore, the present invention encompasses, within its scope, those pharmacologically acceptable non-toxic salts, solvates and hydrates of the compounds of formula (I) and (II).

Suitable pharmacologically acceptable salts of the compounds of formulae (I) and (II) are conventional non-toxic salts and may include inorganic salts, for example, metal salts such as alkali metal salts(e.g., sodium salt, potassium salt, etc.), and alkaline earth metal salts(e.g., calcium salt, magnesium salt, etc.), ammonium salts, etc.; organic salts, for example, organic amine salts(e.g., trimethylamine salt, N-methyl-glucamine salt, diethanolamine salt, triethanolamine salt, triethylamine salt, pyridine salt, procaine salt, picoline salt, dicyclohexylamine salt, N,N'-dibenzylethylenediamine salt, tris(hydroxymethylamino) methane salt, phenylethyl-benzylamine salt, dibenzylethylenediamine salt, etc.); organic carboxylic or sulfonic acid salts (e.g., formate, acetate, maleate, tartrate, methanesulfonate, benzenesulfonate, toluenesulfonate, etc.); inorganic acid salts(e.g., hydrochloride, hydrobromide, sulfate, phosphate, etc.); salts with basic or acidic amino acids(e.g., arginine, aspartic acid, glutamic acid, lysine, etc.); more preferably, alkali metal salts, alkaline earth metal salts, inorganic acid salts, organic carboxylic acid salts and salts with basic or acidic amino acids; and most preferably, sodium salts, potassium salts, hydrochlorides and sulfates.

The above pharmacologically acceptable non-toxic salts may be prepared by reacting the compounds of formula (I) or (II) with one to four equivalents of corresponding acids or bases to the salts mentioned above in the presence of a solvent which may be water, or a mixture of water and water-miscible solvent(e.g., methanol, ethanol, acetonitrile, acetone, etc).

Exemplary solvates of the compounds of formula (I) or (II) may include solvates with water-miscible solvents, preferably, ethanol, which may be prepared by employing a conventional method, for example, as described in "Techniques of Solubilization of Drugs," ed. by Yalkowsky(1981), Marcel Dekker Inc., New York.

The hydrates of the compounds of formula (I) or (II) may be prepared by employing a known method, for example, as described in "Techniques of Solubilization of Drugs," supra.

The compounds of the present invention may be used for the treatment or prophylaxis of diseases caused by HIV, including AIDS. Accordingly, the present invention includes pharmaceutical compositions which contain, in addition to non-toxic, inert pharmaceutically suitable carriers, one or more compounds of the invention. In general, it is advantageous both in human and veterinary medicines to administer the active compound or compounds of the invention in the total amount of about 5~30 mg/kg of body weight every 24 hours, if appropriate, in the form of several individual dosages, to achieve desired results. However, it may be necessary to deviate from the amounts mentioned and in particular to do so as a function of the identity and body weight of the subject to be treated, the kind and severity of the disease, the type of formulation and administration method of the medicament and the interval over which the administration takes place.

The composition of the present invention may be administered orally or by injection. These compositions may be in the form of tablets, capsules, pills, granules, solutions, emulsions, suspensions and the like.

Solutions, emulsions and suspensions may be prepared by using a conventional method. Solutions and emulsions may contain, in addition to the active compound or compounds of the invention, customary carriers or excipients, such as solvents, solubilizing agents and emulsifiers, for example, water, ethyl alcohol, isopropyl alcohol, propylene glycol, oils. Suspensions can contain, in addition to the active compound, customary carriers or excipients, such as liquid diluents, for example, water, ethyl alcohol or propylene glycol and suspending agents, for example, ethoxylated isostearyl alcohol, polyoxyethylene sorbitol and sorbitan esters, microcrystalline cellulose and aluminum metahydroxide, or mixtures of these substances.

Solid compositions for oral administration may include an inert diluent such as sucrose, lactose, etc. and a lubricant such as magnesium stearate. The compound of the present invention may be administered simultaneously with one or more other anti-AIDS agents or immunomodulators.

The following Preparation Examples and Examples are provided for purposes of illustrating certain aspects of the present invention only; and are not to be construed as limiting the scope of the present invention in any way.

The terms and abbreviations used in the Examples have their normal meaning unless otherwise designated, for example: "°C." refers to degrees Celsius; "N" refers to normal or normality; "mmol" refers to millimole; "g" refers to gram; "ml" means milliliter; "M" refers to molar; "NMR" refers to nuclear magnetic resonance; "FABMS" refers to fast atomic bombardment mass spectrometry; "IR" refers to infrared (spectrophotometry); "v/v" means volume per volume; "w/v" refers to weight per volume; and "w/w" means weight per weight.

Unless otherwise specified, percentages or ratios given below for solids in solid mixtures, liquids in liquids and solids in liquids are on a w/w, v/v and w/v basis, respectively.

PREPARATION EXAMPLE 1

Preparation of N-benzyloxycarbonyl-β-methanesulfonyl-L-valine 1-1) Preparation of N-benzyloxycarbonyl-β-(S-methyl)-L-valine 8.9 g (0.06 mol) of L-penicillamine was added to a mixture of 120 ml of dioxane and 40 ml of water. After cooling the mixture to 0° C., 20 ml of 6N NaOH solution was added to dissolve the mixture. To the resulting solution was added 9.24 g (0.066 mol) of iodomethane. After being covered, the mixture was reacted at 0° C. for 3 hours and subsequently at room temperature for 2 hours. The methylated product was cooled to 0° C. and thereto was slowly added 10 ml of 6N NaOH solution and 10.20 g (0.09 mol) of benzylchloroformate. The reaction mixture was stirred at 0° C. for 1 hour and subsequently at 5° C. for 2 hours, and then distilled under reduced pressure to remove the solvent. Then, thereto were added 20 ml of water and ether to remove unreacted benzylchloroformate, and the organic layer was removed. To the aqueous layer was added 60 ml of ethyl acetate and adjusted to pH 3 or less with 6N HCl. The organic layer was separated and dried over anhydrous $MgSO_4$, and the solvent was removed by distillation under reduced pressure to give 14.25 g of the title compound (yield: 80%).

$^1$H NMR($CD_3OD$) δ1.2(s, 6H), 2.1(s, 3H), 4.3(d, 1H), 5.1(s, 2H), 7.1(m, 5H)

1-2) Preparation of N-benzyloxycarbonyl-S-methanesulfonyl-L-valine 2.97 g(0.01 mol) of the compound obtained in Preparation Example 1-1) was dissolved in 30 ml of methanol and the resulting solution was cooled to 0° C. To the solution was added 18.42 g(0.03 mol) of oxone. The mixture was reacted for 3 hours and distilled under reduced pressure to remove the solvent, and to the residue were added 60 ml of ethyl acetate and 20 ml of water. The organic layer was separated and dried over anhydrous $MgSO_4$, and the solvent was removed by distillation under reduced pressure to give 2.73 g of the title compound (yield: 83%).

$^1$H NMR(DMSO) δ2.8(s, 3H), 3.4(m, 2H), 4.6(m, 1H), 5.1(s, 2H), 5.3(d, 1H), 7.2(m, 5H), 8.6(bs, 1H)

PREPARATION EXAMPLE 2

Preparation of (S)-2-amino-3-methyl-1-phenylbutane 2-1) Preparation of 2-methyl-3S-benzyloxycarbonylamino-4-phenyl-1-butene 5.7 g (0.012 mol) of methyltriphenyl phosphine bromide was dissolved in 40 ml of dry toluene, and the mixture was cooled to -20° C. To the mixture, 22 ml (0.011 mol) of 0.5N potassium hexamethyl disilazane solution was added slowly under a nitrogen atmosphere. After stirring for 30 minutes at 0° C., the reaction temperature was reduced to -20° C. 2.97 g (0.01 mol) of 3S-benzyloxycarbonylamino-4-phenyl-2-butanone prepared in accordance with Nahm's method [Tetrahedron Letter, 54, 3815 (1981)] was added slowly thereto. The mixture was reacted at the same temperature for 30 minutes and the temperature was raised to room temperature slowly. Then the mixture was stirred for 3 hours and distilled under reduced pressure to remove the solvent. The residue was purified with column chromatography using ethyl acetate:hexane(10:90) as an eluent to obtain 2.48 g of the title compound(yield: 84%).

$^1$H NMR($CDCl_3$) δ1.77(s, 3H), 2.65–2.95(m, 3H), 4.27 (br, 1H), 4.51(b, 1H), 4.80(d, 2H), 5.12(s, 2H), 7.19–7.33(m, 10H)

2-2) Preparation of (S)-2-amino-3-methyl-1-phenylbutane 2.95 g (0.01 mol) of the compound obtained in Preparation Example 2-1) was dissolved to 30 ml of methanol, and 100 mg of 10% Pd/C was added thereto. The reaction mixture was stirred for 3 hours under an atmosphere of hydrogen (rubber balloon). The resulting solution was filtered through Celite to remove Pd/C and the filtrate was distilled under reduced pressure to remove the solvent to afford 1.61 g of the title compound (yield: 99%).

$^1$H NMR($CDCl_3$) δ0.98(t, 6H), 1.65(m, 1H), 2.39(m, 1H), 2.82(m, 2H), 7.19–7.33(m, 5H)

PREPARATION EXAMPLE 3

Preparation of 2-amino-3-methyl-1-phenylbutane 3-1) Preparation of 2-amino-3-methyl-1-phenylbutane hydrochloride To a solution of 13.8 g(0.2 mol) of isobutylnitrile in 50 ml of dry tetrahydrofuran(THF) was added 110 ml(0.22 mol) of 2.0M benzyl magnesium chloride solution at room temperature. The reaction mixture was refluxed for 1 hour and then cooled to room temperature. 200 ml of methanol and 11.4 g(0.3 mol) of $NaBH_4$ were added to the resulting solution. The reaction mixture was stirred at room temperature for 1 hour, adjusted to pH 11 with 1N NaOH solution, extracted with chloroform, and the extract was dried over anhydrous $NaSO_4$. 50 ml of 5N HCl in methanol was added thereto and the resulting solution was purified with column chromatography using dichloromathane: methanol(10:1) as an eluent to obtain 37.5 g of the title compound (yield 94%).

$^1$H NMR($CDCl_3$) δ1.08(m, 6H), 1.96(m, 1H), 2.90–3.16 (m, 2H), 3.37(m, 1H), 7.15–7.31(m, 5H), 8.36(b, 3H)

3-2) Preparation of L-(N-t-butoxycarbonyl)-phenylalaninyl-2-(1-phenyl-3-methyl-butyl)amide A mixture of 26.5 g(0.1 mol) of N-t-butoxycarbonyl-L-phenylalanine and 1.5 equivalent of each 3-ethyl-3'-(dimethylamino)-propyl carbodiimide(EDC) and N-hydroxybenzotriazol(HOBT) was dissolved in a mixture of 130 ml of dimethyl formamide(DMF) and 15 ml of triethylamine. 20 g(0.1 mol) of the compound obtained in Preparation Example 3-1) was added to the reaction mixture at 0° C. and the whole mixture was stirred at room temperature for 5 hours. The solvent was removed by distillation under a reduced pressure, and the residue was dissolved in ethyl acetate. After washed with 1N hydrochloric acid and saturated NaHCO$_3$ solution, the organic layer was dried over anhydrous MgSO$_4$ and the solvent was removed to give 37.7 g of the title compound (yield: 92%).

3-3) Preparation of L-phenylalaninyl-2-(1-phenyl-3-methyl-butyl)amide 20.5 g(0.05 mol) of the compound obtained in Preparation Example 3-2) was dissolved in a mixture of 30 ml of dichloromethane and 15 ml of trifluoroacetic acid, and the reaction mixture was stirred at room temperature for 1 hour. Thereafter, the mixture was distilled under reduced pressure to remove the solvent, and the residue was purified with column chromato-graphy using ethyl acetate as an eluent to isolate two isomers.

8.0 g($R_f$=0.50) and 7.4 g($R_f$=0.45) of two isomers were obtained respectively, and the total yield was 99%.

$^1$H NMR(CDCl$_3$) δ

$R_f$=0.50 0.93(m, 6H), 1.80(m, 1H), 2.22(m, 1H), 2.63(m, 1H), 2.85(m, 1H), 3.05(m, 1H), 3.51(m, 1H), 4.11(m, 1H), 7.10–7.34(m, 10H)

$R_f$=0.45 0.91(m, 6H), 1.79(m, 1H), 2.65–2.70(m, 2H), 2.83 (m, 1H), 3.18(m, 1H), 3.44(m, 1H), 4.08(m, 1H), 7.10–7.32(m, 10H)

3-4) Preparation of 2-amino-3-methyl-1-phenylbutane

Each 1.46 g(4.7 mmol) of the two isomers obtained in Preparation Example 3-3) was dissolved in 50 ml of dry dichloromethane, and 0.66 ml (5.5 mmol) of phenylisothiocyanate was added thereto at room temperature. Each of the reaction mixtures was refluxed for 2 hours, cooled to room temperature and then 10 ml of trifluoroacetic acid was added thereto. Each of the resulting solutions was refluxed at 60° C. for 40 minutes and then the solvent was removed by distillation under reduced pressure. Each residue was dissolved in 20 ml of water and washed with ether, and then the solution was adjusted to pH 11 with NaOH. The resultant was extracted with chloroform to obtain each isomer of the title compound (yield: 82 to 85%).

$^1$H NMR(CDCl$_3$) δ0.94(m, 6H), 1.11(bs, 2H), 1.65(m, 1H), 2.39(m, 1H), 2.82(m, 2H), 7.16–7.32(m, 5H)

[α]$_D$ (1)–38.1(C=0.12, dichloromethane)
[α]$_D$ (2)+38.1(C=0.12, dichloromethane)

PREPARATION EXAMPLE 4

Preparation of (S)-5-[(N-benzyl-oxycarbonyl)amino]-6-phenyl-hex-3-(cis)-ene-1-carboxylic acid 4-1) Preparation of 5-L-(N-benzyloxycarbonyl)amino-6-phenyl-hex-3-(cis)-enyl-4'-methyl-2',6',7'-trioxa-bicyclo[2',2',2']-oxetane 60.89 g (0.12 mol) of 1-(2-triphenylphosphonium-methyl)-4'-methyl-2',6',7'-trioxa-bicyclo[2',2', 2']oxetane bromide, which is prepared in accordance with the method by Keinan et al. in *Tetrahedron* 26, 4631–4638(1991), was dissolved in 400 ml of tetrahydrofuran, and the mixture was stirred at −78° C. for 10 minutes. Thereto was added 21.9 g(0.11 mol) of potassium hexamethyl disilazane and the whole mixture was stirred at −40° C. for 1 hour. To the mixture, was added a solution of 30 g (0.106 mol) of L-(N-benzyloxycarbonyl)phenyl-alanal dissolved in 150 ml of tetrahydrofuran was added slowly over 20 minutes. The whole mixture was cooled and stirred at −78° C. for 1 hour and subsequently at room temperature for 1 hour, and then, the reaction was quenched with water. The solvent was removed from the reaction mixture and the residue was dissolved in ethyl acetate. The organic layer was washed with saturated NaHCO$_3$ solution and water, dried over anhydrous Na$_2$SO$_4$ and the residue was purified with column chromatography using hexane:ethylacetate:triethylamine (70:25:5) as an eluent to obtain 36.5 g of the title compound (yield: 84%).

$^1$H NMR(CDCl$_3$) δ0.8(s, 3H), 2.2–3.0(m, 4H), 3.9(s, 6H), 4.6(m, 1H), 4.8(br, 1H), 5.05(s, 2H), 5.4–5.6(m, 2H), 7.1–7.5(m, 10H)

4-2) Preparation of (S)-5-[(N-benzyloxycarbonyl)amino]-6-phenyl-hex-3-(cis)-ene-1-carboxylic acid 2.5 g (6 mmol) of the compound obtained in Preparation Example 4-1) was dissolved in 1N HCl in a mixture of water and t-butanol, and the resulting solution was heated at the reflux temperature of the solvent for 20 hours. The solvent was removed by distillation under reduced pressure and the residue was adjusted to pH 9 or higher with saturated K$_2$CO$_3$ solution and then washed with ethyl acetate. The aqueous layer was adjusted to pH 2, and then extracted with ethyl acetate. The extract was dried over anhydrous MgSO$_4$, and the solvent was removed to obtain 1.62 g of the title compound (yield: 80%).

$^1$H NMR(CDCl$_3$) δ2.7–3.3(m, 4H), 4.6(m, 1H), 4.8(br, 1H), 5.05(s, 2H), 5.4(t, 1H), 5.6(m, 1H), 7.1–7.3(m, 10H)
Mass(FAB, m/e) 340(M$^+$+1)
[α]$_D$=+30.6(C=0.10, methanol)

EXAMPLE 1

Preparation of [(5S)-[[N-(2-quinolinecarbonyl)-β-methanesulfonyl-L-alanylyl]amino]-(4R,3S)-epoxy-6-phenyl-hexanoyl]-[(2S)-[1-phenyl-3-methyl]butyl]amide (Compound No. 1)

1-1) Preparation of [(5S)-[(N-benzyloxycarbonyl)amino]-3-(cis)-ene-6-phenyl-1-hexanoyl]-[(2S)-[1-phenyl-3-methyl]butyl]amide A mixture of 3.39 g (10 mmol) of the compound obtained in Preparation Example 4-2) and 1.5 equivalents of each of EDC and HOBT was dissolved in 40 ml of DMF. To the resulting solution was added 1.63 g (10 mmole) of (S)-2-amino-3-methyl-1-phenylbutane at 0° C., and the mixture was stirred at room temperature for 12 hours. The solvent was removed by distillation under reduced pressure, and the residue was dissolved in ethyl acetate. The organic layer was washed with 1N HCl and saturated NaHCO$_3$ solution, dried over anhydrous MgSO$_4$, and distilled under reduced pressure to remove the solvent. The residue was purified with column chromatography using ethyl acetate:hexane (1:1) as an eluent to give 3.8 g of the title compound (yield: 87.5%).

$^1$H NMR(CDCl$_3$) δ0.85–1.01(m, 6H), 1.78(m, 1H), 2.42–3.25(m, 6H), 4.05(m, 1H), 4.58(m, 1H), 4.95(bs, 1H), 5.08(s, 2H), 5.35(m, 1H), 5.58(m, 1H), 7.09–7.41(m, 16H)

1-2) Preparation of [(5S)-[(N-benzyloxycarbonyl)amino]-(4R,3S)-epoxy-6-phenyl-1-hexanoyl]-[(2S)-[1-phenyl-3-methyl]butyl]amide 3.60 g (7 mmol) of the compound obtained in Example 1-1) in 100 ml of dichloromethane was added 2.5 equivalents of metachloroperoxybenzoic acid and the mixture was stirred at room temperature for 24 hours. 10% Na$_2$S$_2$O$_3$ solution was added thereto and the mixture was stirred for 30 minutes. The organic layer was washed with saturated NaHCO$_3$ solution and dried over anhydrous MgSO$_4$. The organic solvent was removed to obtain 3.0 g of the title compound (yield: 83%).

$^1$H NMR(CDCl$_3$) δ0.83–0.99(m, 6H), 1.77(m, 1H), 2.61–3.24(m, 8H), 3.74(m, 1H), 4.11(m, 1H), 4.95(m, 1H), 5.10(s, 2H), 7.21–7.50(m, 15H)

1-3) Preparation of [(5S)-[[N-(benzyloxycarbonyl)-β-methanesulfonyl-L-alanylyl]amino]-(4R,3S)-epoxy-6-phenyl-1-hexanoyl]-[(2S)-[1-phenyl-3-methyl]butyl]amide 315 mg (0.6 mmol) of the compound obtained in Example 1-2) was dissolved in 20 ml of methanol and about 10% by weight of 10% Pd/C was added thereto. The reaction mixture was stirred for 3 hours under an atmosphere of hydrogen (rubber balloon). The resulting solution was filtered through Celite to remove Pd/C and the solvent was removed by distillation under reduced pressure. 181 mg (0.6 mmol) of N-benzyloxycarbonyl-β-methanesulfonyl-L-alanine, 1.5 equivalents of EDC and 1.5 equivalents of HOBT were dissolved in DMF. To the resulting solution, the amine obtained from the above was added at 0° C., and the mixture was stirred at room temperature for 3 hours. The organic solvent was removed by distillation under reduced pressure, and the residue was dissolved in dichloromethane. The organic layer was washed with saturated NaHCO$_3$ solution, dried over anhydrous MgSO$_4$, and the solvent was removed. The residue was purified with column chromatography using hexane:ethyl acetate (1:1) as an eluent to obtain 292 mg of the title compound (yield: 75%).

$^1$H NMR(DMSO) δ1.85(t, 6H), 2.65(m, 2H), 2.0(m, 1H), 2.25(m, 1H), 2.50–3.30(m, 9H), 3.68(br, 1H), 3.43(br, 1H), 5.07(s, 2H) 7.0–7.5(m, 15H), 7.73(m, 2H), 8.41(br, 1H)

1-4) Preparation of [(5S)-[[N-(2-quinolinecarbonyl)-β-methanesulfonyl-L-alanylyl]amino]-(4R,3S)-epoxy-6-phenyl-hexanoyl]-[(2S)-[1-phenyl-3-methyl]butyl]amide 260 mg (0.4 mmol) of the compound obtained in Example 1-3) was dissolved in 20 ml of methanol and about 10% by weight of 10% Pd/C was added thereto. The reaction mixture was stirred for 6 hours under an atmosphere of hydrogen (rubber balloon). The resulting solution was filtered through Celite to remove Pd/C and the solvent was removed by distillation under reduced pressure. 70 mg (0.4 mmol) of 2-quinolinecarboxylic acid, 1.5 equivalents of EDC and 1.5 equivalents of HOBT were dissolved in DMF. To the resulting solution was added the amine obtained from the above at 0° C., and the mixture was stirred at room temperature for 3 hours. The organic solvent was removed by distillation under reduced pressure, and the residue was dissolved in methylene chloride. The organic layer was washed with saturated NaHCO$_3$ solution, dried over anhydrous MgSO$_4$, and the solvent was removed. The residue was purified with column chromatography using ethyl acetate as an eluent to obtain 188 mg of the title compound (yield: 70%).

$^1$H NMR(CDCl$_3$) δ0.8(m, 6H), 1.8(m, 1H), 2.1(m, 2H), 2.6–3.6(m, 11H), 4.1(m, 2H), 5.0(m, 1H), 6.4(d, 1H), 7.1–7.5(m, 11H), 7.5–8.4(m, 6H), 9.3(d, 1H)

Mass(FAB, m/e) 671(M+1)

EXAMPLES 2 and 3

The same procedures as described in Example 1 were repeated using (R)-1-amino-2-methyl-1-phenylpropane and diisopropylmethylamine instead of (S)-2-amino-3-methyl-1-phenylbutane to obtain the Compounds 2 and 3 listed in Table 2, respectively.

EXAMPLE 4

Preparation of [[(5S)-[(N-benzyloxycarbonyl)-β-methanesulfonyl-L-valinylyl]amino]-(4R,3S)-epoxy-6-phenyl-hexanoyl]-[(2S)-[1-phenyl-3-methyl]butyl] amide (Compound No. 4)

4-1) Preparation of [[(5S)-[(N-benzyloxycarbonyl)-β-(S-methyl)-L-valinylyl]amino]-(4R,3S)-epoxy-6-phenyl-hexanoyl]-[(2S)-[1-phenyl-3-methyl]butyl]amide 2.63 g (5 mmol) of the compound obtained in Example 1-2) was dissolved in 100 ml of methanol and about 10% by weight of 10% Pd/C was added thereto. The reaction mixture was stirred for 3 hours under an atmosphere of hydrogen (rubber balloon). The resulting solution was filtered through Celite to remove Pd/C and the solvent was removed. 1.49 g (5 mmol) of the compound obtained in Preparation Example 1-1), 1.5 equivalents of EDC and 1.5 equivalents of HOBT were dissolved in 50 ml of DMF. To the resulting solution was added the amine obtained from the above at 0° C., and the mixture was stirred at room temperature for 3 hours. The organic solvent was removed by distillation under reduced pressure, and the residue was dissolved in dichloromethane. The organic layer was washed with saturated NaHCO$_3$ solution and dried over anhydrous MgSO$_4$. The residue was purified with column chromatography to obtain 1.97 g of the title compound (yield: 75%).

$^1$H NMR(CD$_3$OD) δ0.8(m, 6H), 1.5–2.2(m, 12H), 2.6–3.4(m, 4H), 4.0(m, 2H), 4.5(d, 1H), 5.1(s, 2H), 7.2–7.5 (m, 15H)

4-2) Preparation of [[(5S)-[(N-benzyloxycarbonyl)-β-methaneulfonyl-L-valinylyl]amino]-(4R,3S)-epoxy-6-phenyl-hexanoyl]-[(2S)-[1-phenyl-3-methyl]butyl]amide To 1.93 g (3 mmol) of the compound obtained in Example 4-1) in 100 ml of dichloromethane was added 5 equivalents of metachloroperoxybenzoic acid and the mixture was stirred at room temperature for 2 hours. 10% Na$_2$S$_2$O$_3$ solution was added thereto and the mixture was stirred for 30 minutes. The organic layer was washed with saturated NaHCO$_3$ solution and dried over anhydrous MgSO$_4$. The organic solvent was removed to obtain 1.64 g of the title compound (yield: 85%).

$^1$H NMR(CDCl$_3$) δ0.8(dd, 6H) 1.6–2.2(m, 9H), 2.7–3.4 (m, 7H), 4.0(m, 2H), 4.5(d, 1H), 5.1(s, 2H), 7.1–7.6(m, 15H)

Mass(FAB, m/e) 678(M$^+$+1)

EXAMPLES 5 and 6

The same procedures as described in Example 4 were repeated using (R)-1-amino-2-methyl-1-phenylpropane and diisopropylmethylamine instead of (S)-2-amino-3-methyl-1-phenylbutane to obtain the Compounds 5 and 6 listed in Table 2, respectively.

EXAMPLE 7

Preparation of [[(5S)-N-(2-quinolinecarbonyl)-β-methanesulfonyl-L-valinylyl]amino]-(4R,3S)-epoxy-6-phenyl-hexanoyl]-[(2S)-[1-phenyl-3-methyl]butyl] amide (Compound No. 7)

339 mg (0.5 mmol) of the compound obtained in Example 4-2) was dissolved in 10 ml of methanol and about 10% by weight of 10% Pd/C was added thereto. The reaction mixture was stirred for 3 hours under an atmosphere of hydrogen (rubber balloon). The resulting solution was filtered through Celite to remove Pd/C and the solvent was removed. 0.5 mmol of 2-quinoline carboxylic acid, 1.5 equivalents of EDC and 1.5 equivalents of HOBT were dissolved in 5 ml of DMF. To the resulting solution was added the amine obtained from the above at 0° C., and the mixture was stirred at room temperature for 3 hours. The organic solvent was removed by distillation under reduced pressure, and the residue was dissolved in dichloromethane. The organic layer was washed with saturated NaHCO$_3$ solution and dried over anhydrous MgSO$_4$. The residue was purified with column chromatography using ethyl acetate as an eluent to obtain 271 mg of the title compound (yield: 80%).

$^1$H NMR(CD$_3$OD) δ0.9(m, 6H), 1.5–2.2(m, 9H), 2.6–3.3 (m, 9H), 4.1(m, 2H), 4.7(d, 1H), 5.6(br, 1H)6.8(bs, 1H), 7.1–7.4(m,10H), 7.6–8.4(m, 6H), 9.2(bs, 1H)

Mass(FAB, m/e) 699(M+1)

EXAMPLES 8 and 9

The same procedures as described in Example 7 were repeated using (S)-1-amino-2-methyl-1-phenylpropane and diisopropylmethylamine instead of (S)-2-amino-3-methyl-1-phenylbutane to obtain the Compounds 8 and 9 listed in Table 2, respectively.

EXAMPLE 10

Preparation of [[(5S)-[[N-(2-pyridylmethoxy) carbonyl]-β-methanesulfonyl-L-valinylyl]amino]-(4R,3S)-epoxy-6-phenyl-hexanoyl]-[(2S)-[1-phenyl-3-methyl]butyl]amide (Compound No. 10)

10-1) Preparation of 2-pyridylmethyl-N-succinimidyl carbonate 24.5 mg (0.23 mmol) of 2-pyridylcarbinol and 68.1 mg (0.68 mmole) of triethylamine were dissolved in dry acetonitrile, and 75.9 mg (0.3 mmole) of disuccinimidyl carbonate was added thereto. The reaction mixture was stirred for 3 hours and the solvent was removed by distillation under reduced pressure. The residue was dissolved in ethyl acetate, and the organic layer was washed with saturated NaHCO$_3$ solution and NaCl solution and then dried over anhydrous MgSO$_4$. The solvent was removed by distillation under reduced pressure to obtain 53 mg of the title compound (yield: 92%).

$^1$H NMR(CDCl$_3$) δ2.7(s, 4H), 5.4(s, 2H), 7.6(t, 1H), 7.8(t, 1H), 8.8(m, 2H)

10-2) Preparation of [(5S)-[[N-(2-pyridylmethoxy) carbonyl]-β-methansulfonyl-L-valinylyl]amino]-(4R,3S)-epoxy-6-phenyl-hexanoyl]-[(2S)-[1-phenyl-3-methyl]butyl] amide 101 mg (0.15 mmol) of the compound obtained in Example 4-2) which was deprotected in the same manner as described in Example 7, 68.1 mg (0.68 mmole) of triethylamine and 40 mg (0.16 mmole) of the compound obtained in Example 10-1) were dissolved in dry dichloromethane and the mixture was stirred at room temperature for 20 hours or longer. The organic layer was washed with saturated NaHCO$_3$ solution and dried over anhydrous MgSO$_4$, and then the organic solvent was removed. The residue was purified with column chromatography using ethyl acetate as an eluent to obtain 50.8 mg of the title compound (yield: 50%).

$^1$H NMR(CDCl$_3$) δ0.9(m, 6H), 1.5–2.1(m, 9H), 2.6–3.3 (m, 9H), 4.1(m, 2H), 4.7(d, 1H), 5.2(bs, 3H), 5.6(br, 1H), 6.8(br, 1H), 7.1–7.4(m, 12H), 7.7(d, 1H), 8.7(m, 1H)

Mass(FAB, m/e) 631(M+1)

EXAMPLES 11 and 12

The same procedures as described in Example 10 were repeated using (R)-1-amino-2-methyl-1-phenylpropane and diisopropylmethylamine instead of (S)-2-amino-3-methyl-1-phenylbutane to obtain the Compounds 11 and 12 listed in Table 2, respectively.

EXAMPLE 13

The same procedures as described in Example 10 were repeated using 3-pyridylcarbinol instead of 2-pyridylcarbinol to obtain the Compound 13 listed in Table 2.

EXAMPLES 14 and 15

The same procedures as described in Example 10 were repeated using (R)-1-amino-2-methyl-1-phenylpropane and diisopropylmethylamine instead of (S)-2-amino-3-methyl-1-phenylbutane to obtain the Compounds 14 and 15 listed in Table 2, respectively.

EXAMPLE 16

The same procedures as described in Example 10 were repeated using 4-pyridylcarbinol instead of 2-pyridylcarbinol to obtain the Compound 16 listed in Table 2.

EXAMPLES 17 and 18

The same procedures as described in Example 10 were repeated using (R)-1-amino-2-methyl-1-phenylpropane and diisopropylmethylamine instead of (S)-2-amino-3-methyl-1-phenylbutane to obtain the Compounds 17 and 18 listed in Table 2, respectively.

EXAMPLES 19 to 30

The reactions of carboxylic acids with amines were carried out by the same procedures as described in Example 7 to obtain the compounds 19 to 30 listed in Table 2.

PREPARATION EXAMPLE 5

Preparation of N-cyclopentyloxy carbonyl-S-methyl-O-benzylpenicillamine 5-1) Preparation of (N-t-butoxycarbonyl)amino-S-methyl-L-penicillamine 8.9 g (0.06 mol) of L-penicillamine was added to a mixture of 120 ml of dioxane and 40 ml of water. After cooling the mixture to 0° C., 20 ml of 6N NaOH solution was added to dissolve the mixture. To the resulting solution was added 9.24 g (0.066 mol) of methane iodide. After being covered, the mixture was reacted at 0° C. for 3 hours and subsequently at room temperature for 2 hours. The reaction mixture was cooled to 0° C. and thereto was slowly added 12.18 g (0.07 mol) of t-butoxydicarbonate. The mixture was stirred at 0° C. for 1 hour and subsequently at room temperature for 2 hours and distilled under reduced pressure to remove the solvent. 20 ml of water and ether were added to the residue to remove unreacted t-butoxydicarbonate, and then the organic layer was removed. To the aqueous layer was added 300 ml of ethyl acetate and adjusted to pH 3 with 6N HCl . The organic layer was separated and dried over anhydrous MgSO$_4$, and then the solvent was removed by distillation under reduced pressure to obtain 12.62 g of the title compound (yield: 80%).

$^1$H NMR(CDCl$_3$) δ1.38(s, 3H), 1.41(s, 3H), 1.46(s, 9H), 2.06(s, 3H), 4.35(d, 1H), 5.68(d, 1H)

5-2) Preparation of S-methyl-O-benzyl penicillamine 2.63 g(0.01 mol) of the compound obtained in Preparation Example 5-1) was dissolved in 50 ml of DMF and to the resulting solution were added 2 equivalents of potassium carbonate and 1 equivalent of benzyl bromide. The mixture was reacted for 3 hours and distilled under reduced pressure to remove the solvent. To the residue were added 100 ml of ethyl acetate and 200 ml of water. The organic layer was separated and dried over anhydrous Na$_2$SO$_4$, and the solvent was removed by distillation under reduced pressure. The residue was dissolved in 20 ml of dichloromethane and thereto was added 10 ml of CF$_3$COOH. The mixture was stirred for 1 hour and distilled under reduced pressure to remove the solvent. To the residue were added 100 ml of ethyl acetate and 200 ml of saturated NaHCO₃ solution. The organic layer was separated and dried over anhydrous MgSO₄, and the solvent was removed by distillation under reduced pressure to obtain 2.33 g of the title compound (yield: 92%).

¹H NMR(CDCl₃) δ1.26(s, 3H), 1.34(s, 3H), 2.02(s, 3H), 3.52(s, 1H), 5.17(s, 2H), 7.37–7.43(m, 5H)

5-3) Preparation of N-p-nitrophenyloxycarbonyl-S-methyl-O-benzyl penicillamine 1.5 equivalents of NaHCO₃ and 1 equivalent of the compound obtained in Preparation Example 5-2) were added to 2.1 g(10.5 mmol) of p-nitrophenyl chloroformate dissolved in 50 ml of acetonitrile at 0° C. The mixture was stirred for 1 hour at room temperature and distilled under reduced pressure to remove the solvent. The residue was dissolved in ethyl acetate, and the mixture was washed with K₂CO₃ and dried over anhydrous MgSO₄. The solvent was removed by distillation under reduced pressure to obtain 3.84 g of the title compound (yield: 92%).

¹H NMR(CDCl₃) δ1.40(s, 3H), 1.42(s, 3H), 2.03(s, 3H), 4.43(d, 1H), 5.21(dd, 2H), 6.03(d, 1H), 7.32–7.73(m, 7H), 8.23(d, 2H)

5-4) Preparation of N-cyclopentyloxycarbonyl-S-methyl-O-benzyl penicillamine

A solution of 86 mg (10 mmol) of cyclopentyl alcohol and 1.1 equivalents of triethylamine dissolved in 10 ml of acetonitrile was added to the reaction solution of Preparation Example 5-3) at room temperature. The mixture was refluxed for 10 hours and distilled under reduced pressure to remove the solvent. The residue was dissolved in ethyl acetate, and the solution was washed with 1N HCl and K₂CO₃ solution and then dried over anhydrous MgSO₄. The solvent was removed and the residue was purified with column chromatography using hexane:ethyl acetate (25:1) as an eluent to obtain 240 mg of the title compound (yield: 72%).

¹H NMR(CDCl₃) δ1.18(d, 1H), 1.32–1.83(m, 8H), 1.89(s, 3H), 4.23(d, 1H), 4.91(bs, 1H), 5.08(dd, 2H), 5.31(d, 1H), 7.23(m, 5H)

EXAMPLE 31

Preparation of [(5S)-[[N-cyclopentyloxycarbonyl)-β-methanesulfonyl-L-valinyl]amino]-(4R,3S)-epoxy-6-phenyl-1-hexanoyl]-[(2S)-[1-phenyl-3-methyl]butyl]amide (Compound No. 31)

250 mg (0.5 mmol) of the compound obtained in Example 1-2) was dissolved in 20 ml of methanol and 10% by weight of 10% Pd/C was added thereto. The reaction mixture was stirred for 3 hours under an atmosphere of hydrogen (rubber balloon). The resulting solution was filtered through Celite to remove Pd/C and the solvent was removed by distillation under reduced pressure. 0.5 mmol of the acid, which was prepared by treating the compound obtained in Preparation Example 5-4) with LiOH, and 1.5 equivalents of each of EDC, HOBT and triethylamine were dissolved in 10 ml of DMF. To the resulting solution, the amine obtained from the above was added at 0° C., and the mixture was stirred at room temperature for 3 hours. The organic solvent was removed by distillation under reduced pressure, and the residue was dissolved in ethyl acetate. The organic layer was washed with saturated NaHCO₃ solution and added to 20 ml of dichloromethane. Thereto was added 3 equivalents of metachloroperoxybenzoic acid, and the mixture was stirred at room temperature for 24 hours. 30 ml of 10% of Na₂S₂O₃ solution was added thereto and the mixture was stirred for 30 minutes. The organic layer was washed with saturated NaHCO₃ solution, dried over anhydrous MgSO₄ and the organic solvent was removed by distillation under reduced pressure. The residue was purified with column chromatography using dichloromethane:methanol(20:1) as an eluent to obtain 153 mg of the title compound (yield: 47%).

¹H NMR(CDCl₃) δ0.86–0.95(m, 6H), 1.13–2.22(m, 17H), 2.45–3.47(m, 9H), 4.13(m, 2H), 4.61(d, 1H), 4.91(m, 1H), 6.43(bs, 1H), 7.08–7.42(m, 11H)

Mass(FAB, m/e) 656(M+1)

EXAMPLE 32

The same procedures as described in Example 31 were repeated using ethanol instead of cyclopentylalcohol in Preparation Example 5-4) to obtain the Compound 32 listed in Table 2.

EXAMPLE 33

The same procedures as described in Example 32 were repeated using 3-amino-2,4-dimetylpentane instead of (S)-2-amino-3-methyl-1-phenylbutane in Preparation Example 2 to obtain the Compound 33 listed in Table 2.

EXAMPLE 34

The same procedures as described in Example 31 were repeated using isopropanol instead of cyclopentylalcohol in Preparation Example 5-4) to obtain the Compound 34 listed in Table 2.

EXAMPLE 35

The same procedures as described in Example 31 were repeated using 2-furanylmethylalcohol instead of cyclopentyl alcohol in Preparation Example 5-4) to obtain the Compound 35 listed in Table 2.

EXAMPLE 36

The same procedures as described in Example 31 were repeated using cyclopropylmethanol instead of cyclopentyl alcohol in Preparation Example 5-4) to obtain the Compound 36 listed in Table 2.

PREPARATION EXAMPLE 6

Preparation of [S-methyl-O-benzyl-L-penicillamine]-[methyl-n-butylamine]urea

A solution of 0.12 g (10 mmol) of methyl-n-butylamine and 1.1 equivalents of triethylamine dissolved in 10 ml of acetonitrile was added to the reaction solution of Preparation Example 5-3) at room temperature. After 10 minutes, the solvent was removed by distillation under reduced pressure and the residue was dissolved in ethyl acetate. The solution was washed with 1N HCl and K₂CO₃ solution and dried over anhydrous MgSO₄. The solvent was removed and the residue was purified with column chromatography using hexane:ethyl acetate(8:2) as an eluent to obtain 3.09 g of the title compound(yield: 92%).

¹H NMR(CDCl₃) δ0.82(t, 3H), 1.18(m, 8H), 1.35(m, 2H), 1.98(s, 3H), 2.81(s, 3H), 3.12(t, 2H), 4.32(d, 1H), 5.05(dd, 2H), 5.2(d, 1H), 7.24(m, 5H)

EXAMPLE 37

Preparation of [(5S)-[[[(N,N-methylbutyl)aminocarbonyl]-β-methanesulfonyl-L-valinyl]amino]-(4R,3S)-epoxy-6-phenyl-1-hexanoyl]-[(2S)-[1-phenyl-3-methyl]butyl]amide (Compound No. 37)

250 mg (0.5 mmol) of the compound obtained in Example 1-2) was dissolved in 20 ml of methanol and 10% by weight of 10% Pd/C was added thereto. The reaction mixture was stirred for 3 hours under an atmosphere of hydrogen (rubber balloon). The resulting solution was filtered through Celite to remove Pd/C and the solvent was removed by distillation under reduced pressure. 0.5 mmol of the acid, which was prepared by treating the compound obtained in Preparation Example 6 with LiOH, and 1.5 equivalents of each of EDC, HOBT and triethylamine were dissolved in 10 ml of DMF. To the resulting solution, the amine obtained from the above was added at 0° C., and the mixture was stirred at room temperature for 3 hours. The organic solvent was removed by distillation under reduced pressure, and the residue was dissolved in ethyl acetate. The organic layer was washed with saturated NaHCO$_3$ solution, and added to 20 ml of dichloromethane. Thereto was added 3 equivalents of metachloroperoxybenzoic acid, then the mixture was stirred at room temperature for 24 hours. 30 ml of 10% of Na$_2$S$_2$O$_3$ solution was added thereto and the mixture was stirred for 30 minutes. The organic layer was washed with saturated NaHCO$_3$ solution, dried over anhydrous MgSO$_4$ and the organic solvent was removed by distillation under reduced pressure. The residue was purified with column chromatography using dichloromethane:methanol(20:1) as an eluent to obtain 223 mg of the title compound (yield: 68%).

$^1$H NMR(CDCl$_3$) δ0.92(m, 9H), 1.21–2.22(m, 10H), 2.64–3.32(m, 14H), 4.02(m, 2H), 4.82(d, 1H), 6.2(bs, 2H), 7.12–7.33(m, 11H)

Mass(FAB, m/e) 657(M+1)

EXAMPLES 38 to 40

The same procedures as described in Example 37 were repeated using cyclopropylmethylamine, benzylamine and 2-furanylmethylamine, instead of methyl-n-butylamine in Preparation Example 6 to obtain the Compounds 38, 39 and 40 listed in Table 2, respectively.

EXAMPLE 41

Preparation of [(5S)-[[(N-2-thiophenecarbonyl)-β-methanesulfonyl-L-valinyl]amino]-(4R,3S)-epoxy-6-phenyl-1-hexanoyl]-[(2S)-[1-phenyl-3-methyl]butyl] amide (Compound No. 41)

339 mg (0.5 mmol) of the compound obtained in Example 4-2) was dissolved in 20 ml of methanol and 10% by weight of 10% Pd/C was added thereto. The reaction mixture was stirred for 3 hours under an atmosphere of hydrogen (rubber balloon). The resulting solution was filtered through Celite to remove Pd/C and the solvent was removed by distillation under reduced pressure. 64.1 mg (0.5 mmol) of 2-thiophenic acid, and 1.5 equivalents of each of EDC, HOBT and triethylamine were dissolved in 10 ml of DMF. To the resulting solution was added the amine obtained from the above at 0° C., and the mixture was stirred at room temperature for 3 hours. The solvent was removed by distillation under reduced pressure, and the residue was dissolved in ethyl acetate. The organic layer was washed with saturated NaHCO$_3$ solution and dried over anhydrous MgSO$_4$, and the organic solvent was removed by distillation under reduced pressure. The residue was purified with column chromatography using dichloromethane:methanol(20:1) as an eluent to obtain 236 mg of the title compound (yield: 72%).

$^1$H NMR(CDCl$_3$) δ0.89(m, 6H), 1.49–2.05(m, 9H), 2.62 (m, 1H), 2.76–3.01(m, 8H), 4.03(m, 2H), 4.98(d, 1H), 5.73(d, 1H), 7.09–7.56(m, 15H)

Mass(FAB, m/e) 654(M+1)

EXAMPLES 42 to 45

The same procedures as described in Example 41 were repeated using 2-furanic acid, 2-pyridinic acid, 3-pyridinic acid and 2-(4-oxo-2,3-dihydro-6,6-dimethylpyranic acid) instead of 2-thiophenic acid to obtain the Compounds 42, 43, 44 and 45 listed in Table 2, respectively.

EXAMPLE 46

Preparation of [(5S)-[[(N-isovaleroyl)-β-methanesulfonyl-L-valinyl]amino]-(4R,3S)-epoxy-6-phenyl-1-hexanoyl]-[(2S)-[1-phenyl-3-methyl]butyl] amide 339 mg (0.5 mmol) of the compound obtained in Example 4-2) was dissolved in 20 ml of methanol and 10% by weight of 10% Pd/C was added thereto. The reaction mixture was stirred for 3 hours under an atmosphere of hydrogen (rubber balloon). The resulting solution was filtered through Celite to remove Pd/C and the solvent was removed by distillation under reduced pressure. 51 mg (0.5 mmol) of isovaleric acid, and 1.5 equivalents of each of EDC, HOBT and triethylamine were dissolved in 10 ml of DMF. To the resulting solution was added the amine obtained from the above at 0° C., and the mixture was stirred at room temperature for 3 hours. The solvent was removed by distillation under reduced pressure, and the residue was dissolved in ethyl acetate. The organic layer was washed with saturated NaHCO$_3$ solution and dried over anhydrous MgSO$_4$, and the organic solvent was removed by distillation under reduced pressure. The residue was purified with column chromatography using dichloromethane:methanol(20:1) as an eluent to obtain 260 mg of the title compound (yield: 83%).

$^1$H NMR(CDCl$_3$) δ0.85–0.98(m, 12H), 1.47(d, 6H), 1.71 (m, 1H), 1.83(m, 1H), 2.10–2.12(m, 2H), 2.60(m, 1H), 2.72–3.15(m, 10H), 3.95–4.10(m, 2H), 4.95(d, 1H), 5.93(d, 1H), 6.95(d, 1H), 7.10–7.35(m, 10H), 7.72(bs, 1H)

Mass(FAB, m/e) 628(M+1)

EXAMPLES 47 to 50

The same procedures as described in Example 46 were repeated using methoxyacetic acid, isopropyloxyacetic acid, thiopheneacetic acid and furanacetic acid instead of isovaleric acid to obtain the Compounds 47, 48, 49 and 50 listed in Table 2, respectively.

EXAMPLE 51

Preparation of 4S-[(N$^1$-toluenesulfonyl)amino]-[N$^4$-[N'-(2-quinolinecarbonyl)-L-asparaginyl]amino]-5-phenyl-(2S,3R)-epoxy pentane (Compound No. 51)

51-1) Preparation of N-[(2-triphenylphosphine)ethyl] phthalimide bromide

A mixture of 2.54 g(10 mmol) of N-(2-bromoethyl) phthalimide and 2 equivalents of triphenylphosphine was stirred in the absence of a solvent at 150° C. for 16 hours, and the resulting mixture was recrystallized from ethanol and ether to obtain 4.5 g of the title compound (yield: 88%).

$^1$H NMR(CDCl$_3$) δ4.32(m, 2H), 4.54(m, 2H), 7.51–7.71 (m, 15H), 7.81–7.93(m, 4H)

51-2) Preparation of 4S-[(N$^1$-phthaloyl)amino]-[(N$^4$-benzyloxycarbonyl)amino]-5-phenyl-(2,3)-pentene 0.568 g (1.1 mmol) of the compound obtained in Example 51-1) was dissolved in 30 ml of dry tetrahydrofuran, and to the resulting solution was slowly added 2.2 ml (1.1 mmol) of 0.5M potassium hexamethyl disilazane solution at −78° C. The resulting mixture was stirred for 1 hour and thereto was added a solution of 0.283 g (1 mmol) of N-benzyloxycarbonyl-L-phenylalanal dissolved in 10 ml of dry tetrahydrofuran. The whole mixture was stirred at −78°

C. for 1 hour and subsequently at room temperature for 1 hour, and then, the reaction was quenched with water. After removing the solvent from the reaction mixture, the residue was dissolved in 50 ml of ethyl acetate. The solution was washed with saturated NaHCO$_3$ solution and water, and then dried over anhydrous MgSO$_4$ and distilled under reduced pressure. The residue was purified with column chromatography using hexane:ethyl acetate (70:30) as an eluent to obtain 0.374 g of the title compound (yield: 84%).

$^1$H NMR(CDCl$_3$) δ2.78–2.99(m, 2H), 4.26(m, 2H), 4.59 (bs, 1H), 4.85(m, 1H), 5.10(s, 2H), 5.44–5.58(m, 2H), 7.15–7.32(m, 10H), 7.72–7.95(m, 4H)

51-3) Preparation of 4S-[(N$^4$-benzyloxycarbonyl)amino]-1-amino-5-phenyl-(2,3)-pentene 0.44 g (1 mmol) of the compound obtained in Example 51-2) and 3 equivalents of hydrazine were dissolved in 20 ml of ethanol. The resulting mixture was refluxed for 3 hours and filtered to remove the solid products. The solvent was removed from the filtrate and the residue was dissolved in 50 ml of ethyl acetate. The organic layer was washed with 0.2N NaOH solution and dried over anhydrous MgSO$_4$ to obtain 0.298 g of the title compound (yield: 96%).

$^1$H NMR(CDCl$_3$) δ2.65–3.23(m, 4H), 4.64(m, 1H), 5.11 (s, 2H), 5.15–5.54(m, 2H), 7.09–7.43(m, 10H)

Preparation of 4S-[(N$^1$-toluenesulfonyl)amino]-[(N$^4$-benzyloxycarbonyl)amino]-5-phenyl-(2,3)-pentene 0.31 g (1 mmol) of the compound obtained in Example 51-3) and 1.1 equivalents of each of toluenesulfonyl chloride and tirethylamine were dissolved in 20 ml of DMF and the mixture was stirred for 16 hours. The solvent was removed by distillation under reduced pressure, and the residue was dissolved in 50 ml of ethyl acetate. The organic layer was washed with NaHCO$_3$ solution and dried over anhydrous MgSO$_4$, and then the solvent was removed. The residue was purified with column chromatography using ethyl acetate:hexane(1:3) as an eluent to obtain 0.36 g of the title compound in which 2,3-position was cis-olefin(yield: 77%).

$^1$H NMR(CDCl$_3$) δ2.43(s, 3H), 2.62(m, 1H), 2.85(m, 1H), 3.20–3.41(m, 2H), 4.40(m, 1H), 4.78(bs, 1H), 5.01(bs, 1H), 5.10(s, 2H), 5.31(m, 1H), 5.52(m, 1H), 7.01–7.75(m, 14H)

51-5) Preparation of 4S-[(N$^1$-toluenesulfonyl)amino]-[(N$^4$-benzyloxycarbonyl)amino]-5-phenyl-(2S,3R)-epoxy pentene To 0.464 g (1 mmol) of the compound obtained in Example 51-4) in 20 ml of dichloromethane was added 3 equivalents of metachloroperoxybenzoic acid and the mixture was stirred at room temperature for 24 hours. 30 ml of 10% Na$_2$S$_2$O$_3$ solution was added thereto and the mixture was stirred for 30 minutes. The organic layer was washed with saturated NaHCO$_3$ solution and dried over anhydrous MgSO$_4$. The organic solvent was removed and the residue was purified with column chromatography using ethyl acetate:hexane(2:3) as an eluent to obtain 0.39 g of the title compound (yield: 81%).

$^1$H NMR(CDCl$_3$) δ2.39(m, 1H), 2.42(s, 3H), 2.74(m, 2H), 2.97(m, 2H), 3.14(m, 1H), 3.68(m, 1H), 3.89(m, 1H), 4.95(bs, 1H), 5.11(s, 2H), 7.15–7.76(m, 14H) 51-6) Preparation of 4S-[(N$^1$-toluenesulfonyl)amino]-[N$^4$-[N'-(2-quinolinecarbonyl)-L-asparaginyl]amino]-5-phenyl-(2S, 3R) epoxy pentane 241 mg (0.5 mmol) of the compound obtained in Example 51-5) was dissolved in 20 ml of methanol and 10% by weight of 10% Pd/C was added thereto. The reaction mixture was stirred for 3 hours under an atmosphere of hydrogen (rubber balloon). The resulting solution was filtered through Celite to remove Pd/C and the solvent was removed by distillation under reduced pressure. 144 mg(0.5 mmol) of N-(2-quinolinecarbonyl)-asparagine, and 1.5 equivalents of each of EDC, HOBT and triethylamine were dissolved in 10 ml of DMF. To the resulting solution, the amine obtained from the above was added at 0° C., and the mixture was stirred at room temperature for 3 hours. The solvent was removed by distillation under reduced pressure, and the residue was dissolved in ethyl acetate. The organic layer was washed with saturated NaHCO$_3$ solution and dried over anhydrous MgSO$_4$. The solvent was removed by distillation under reduced pressure and the residue was purified with column chromatography using dichloromethane: methanol (10:1) as an eluent to obtain 206 mg of the title compound (yield: 67%).

$^1$H NMR(CDCl$_3$) δ2.41(s, 3H), 2.46(m, 2H), 2.65–3.13 (m, 8H), 3.89(m, 1H), 5.02(m, 1H), 5.78(d, 1H), 6.19(d, 1H), 6.70(d, 1H), 7.07–8.29(m, 16H), 9.37(d, 1H)

Mass(FAB, m/e) 616(M+1)

EXAMPLE 52

The same procedures as described in Example 51 were repeated using p-aminobenzenesulfonyl chloride instead of toluenesulfonyl chloride to obtain the Compound 52 listed in Table 2.

EXAMPLE 53

The same procedures as described in Example 51 were repeated using isobutyl bromide together with the title compound of Example 51-3) to obtain the compound 53 listed in Table 2.

TABLE 2
| Comp. No. | Structure | FAB MS (M+1) | ¹HNMR δ (CDCl₃) |
|---|---|---|---|
| 1 | 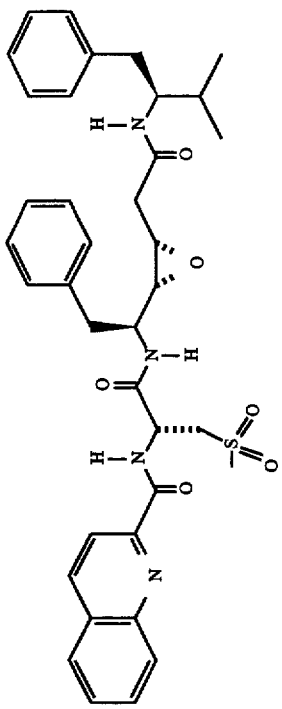 | 671 | 0.85(m, 6H), 1.82(m, 1H), 2.11(m, 2H), 2.6–3.6(m, 11H), 4.11(m, 2H), 5.01(m, 1H), 6.41(d, 1H), 7.10–7.51(m, 11H), 7.5–8.4(m, 6H), 9.31(d, 1H). |
| 2 | 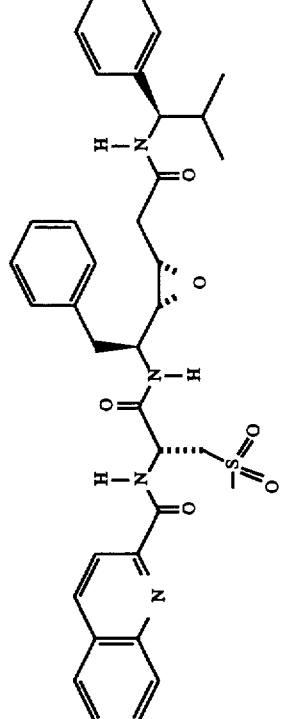 | 657 | 0.82(m, 6H), 1.82(m, 1H), 2.12(m, 2H), 2.71–3.60(m, 9H), 4.12(m, 1H), 4.55(m, 1H), 4.92(m, 6H), 6.61(d, 1H), 7.1–7.6(m, 11H), 7.5–8.14(m, 6H), 9.40(d, 1H). |
| 3 | 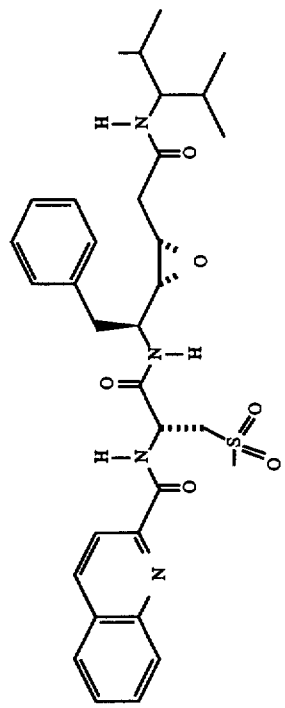 | 623 | 0.82(m, 12H), 1.82(m, 2H), 2.01(m, 2H), 2.80–3.61(m, 10), 4.12(m, 1H), 5.01(m, 1H), 5.62(d, 1H), 7.0–7.5(m, 6H), 7.5–8.4(m, 7H), 9.25(d, 1H). |

TABLE 2-continued

| | Structure | MS | NMR |
|---|---|---|---|
| 4 | 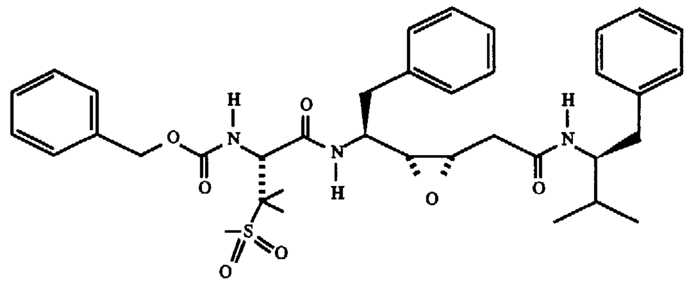 | 678 | 1.90(m, 6H), 1.42(s, 3H), 1.51(s, 3H), 1.71(m, 1H), 1.80–2.20(m, 2H), 2.50–3.15(m, 9H), 4.05(m, 2H), 4.51(d, 1H), 5.10(s, 2H), 5.71(d, 1H), 5.98(d, 1H), 6.89(d, 1H), 7.10–7.40(m, 15H). |
| 5 | 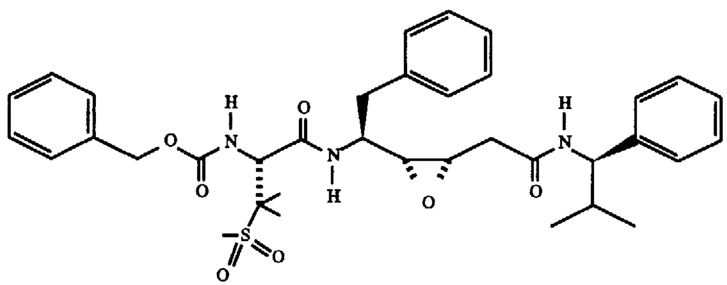 | 664 | 0.81(d, 3H), 0.89(d, 3H), 1.50(s, 6H), 1.90–2.20(m, 3H), 2.80–3.30(m, 7H), 4.10(m, 1H), 4.58(d, 1H), 4.67(m, 1H), 5.10(s, 2H), 5.94(d, 1H), 6.27(d, 1H), 6.80(d, 1H), 7.10–7.40(m, 15H). |
| 6 | 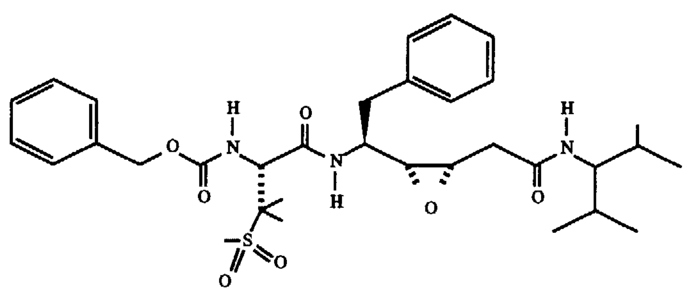 | 630 | 0.75–0.85(d, 6H), 0.85–0.95(d, 6H), 1.45(s, 3H), 1.55(s, 3H), 1.65–1.85(m, 2H), 1.90–2.21(m, 2H), 2.79–3.15(m, 6H), 3.20–3.35(m, 1H), 3.45–3.55(m, 1H), 4.00–4.21(m, 1H), 4.55–4.65(d, 1H), 5.12(s, 2H), 5.50–5.65(br, 1H), 6.95–6.05(br, 1H), 6.80–6.95(br, 1H), 7.10–7.40(m, 10H). |

TABLE 2-continued
| | | | |
|---|---|---|---|
| 7 | 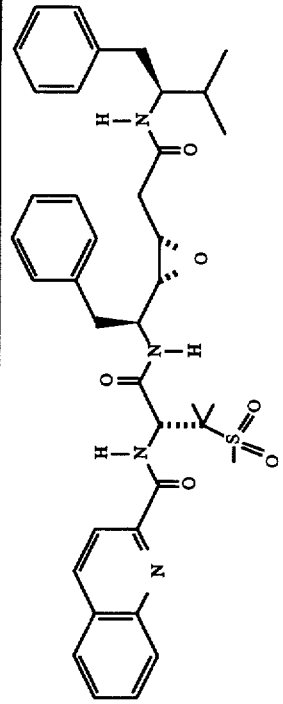 | 699 | 0.95(d, 6H), 1.60(s, 6H), 1.75(m, 1H), 1.90–2.20(m, 2H), 2.60–3.15(m, 9H), 4.15(m, 2H), 5.12(d, 1H), 5.83(d, 1H), 6.95–7.20(m, 11H), 7.50–8.45(m, 6H), 9.33(d, 1H). |
| 8 | 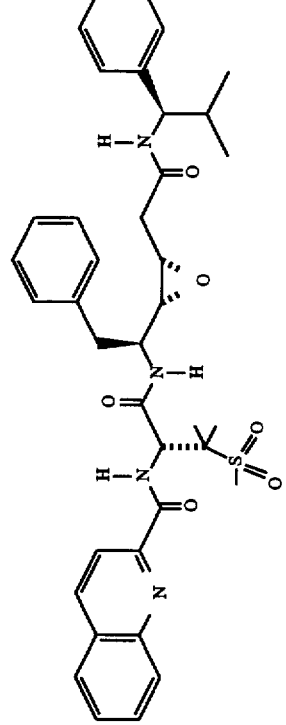 | 685 | 0.81(d, 3H), 0.90(d, 3H), 1.55(s, 6H), 1.90–2.20(m, 3H), 2.80–3.30(m, 7H), 4.17(m, 1H), 4.69(m, 1H), 5.07(d, 1H), 6.45(d, 1H), 6.90–7.30(m, 11H), 7.50–8.45(m, 6H), 9.36(d, 1H). |
| 9 | 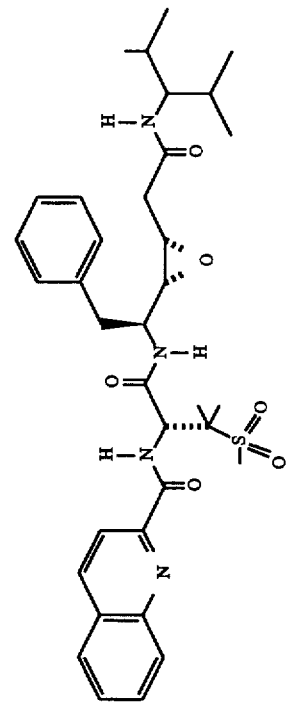 | 651 | 0.81(m, 12H), 1.60(s, 6H), 1.78(m, 2H), 1.90–2.21(m, 2H), 2.80–3.15(m, 6H), 3.37(m, 1H), 3.50(m, 1H), 4.13(m, 1H), 5.12(d, 1H), 5.71(d, 1H), 6.95–7.30(m, 6H), 7.50–8.45(m, 6H), 9.31(d, 1H). |

TABLE 2-continued

| | Structure | MW | NMR |
|---|---|---|---|
| 10 | 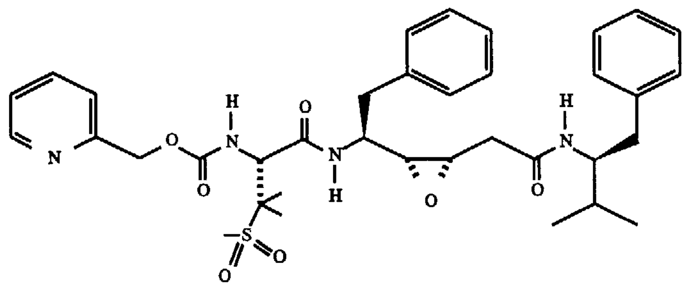 | 679 | 0.72–0.91(m, 6H), 1.36(s, 3H), 1.45(s, 3H), 2.5–2.10(m, 9H), 2.50–3.10(m, 9H), 4.12(m, 2H), 4.58(d, 1H), 5.13(s, 2H), 5.65(d, 1H), 6.14(d, 1H), 6.93(d, 1H), 7.10–7.40(m, 12H), 7.61(br, 1H), 8.21(br, 1H). |
| 11 | 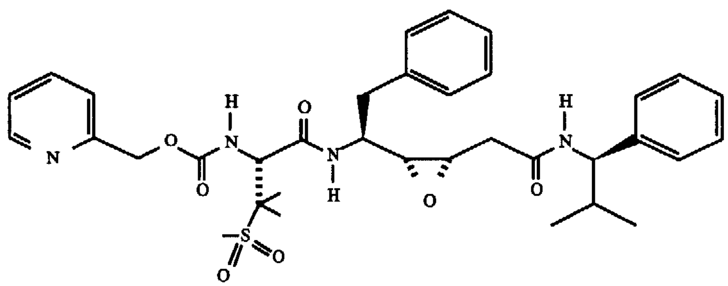 | 665 | 0.75–0.97(m, 6H), 1.51(s, 3H), 1.56(s, 3H), 1.80–2.30(m, 3H), 2.80–3.15(m, 6H), 3.31(m, 1H), 4.15(m, 1H), 4.61(d, 1H), 4.71(m, 1H), 5.12(s, 1H), 5.15(s, 1H), 6.15(d, 1H), 5.38(d, 1H), 6.95(d, 1H), 7.1–7.40 (m, 7H), 7.61(m, 1H), 8.20(br, 1H). |
| 12 | 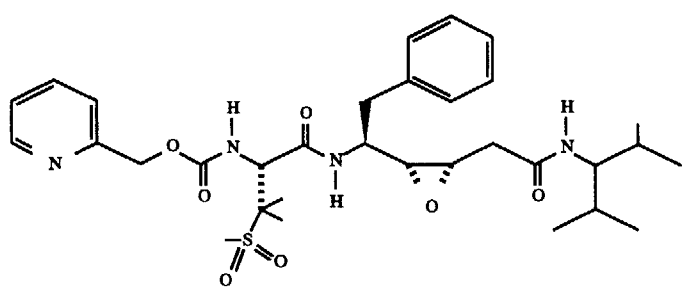 | 631 | 0.80(m, 12H), 1.51–2.32(m, 10H), 2.71–3.80(m, 8H), 4.10(m, 1H), 4.62(d, 1H), 5.21(s, 2H), 5.86(br, 1H), 6.10(br, 1H), 6.91–7.40(m, 8H), 7.61(br, 1H), 8.20(br, 1H). |

TABLE 2-continued

| | Structure | | NMR |
|---|---|---|---|
| 13 | (structure) | 679 | 0.70–0.90(m, 6H), 1.37(s, 3H), 1.45(s, 3H), 2.55–2.10(m, 3H), 2.50–3.10(m, 9H), 3.97–4.20(m, 2H), 4.52–4.63(d, 1H), 5.13(s, 2H), 5.60–5.70(br, 1H), 6.10–6.20(br, 1H), 6.90–7.00(br, 1H), 7.05–7.30(m, 11H), 7.65–7.75(br, 1H), 8.40–8.65(m, 2H). |
| 14 | (structure) | 665 | 0.75–1.00(m, 6H), 1.45(s, 3H), 1.57(s, 6H), 1.80–2.30(m, 3H), 2.80–3.15(m, 6H), 3.30(m, 1H), 4.60(d, 1H), 4.73(m, 1H), 5.11(s, 1H), 5.15(s, 1H), 6.10(d, 1H), 6.38(d, 1H), 7.0–7.45(m, 12H), 7.81(m, 1H), 8.50–8.70(m, 2H). |
| 15 | (structure) | 631 | 0.90(m, 12H), 1.44(s, 3H), 1.50(s, 3H), 1.70(m, 2H), 1.85–2.20(m, 2H), 2.80–3.15(m, 6H), 3.27(m, 1H), 3.55(m, 1H), 4.05(m, 1H), 4.55(d, 1H), 5.15(s, 2H), 5.60(br, 1H), 6.03(br, 1H), 6.97(br, 1H), 7.10–7.40(m, 7H), 7.70(d, 1H), 8.60(m, 2H). |

TABLE 2-continued

| | Structure | MS | NMR |
|---|---|---|---|
| 16 | 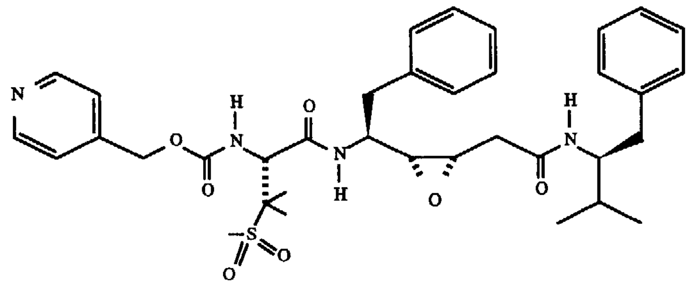 | 679 | 0.71–0.90(m, 6H), 1.37(s, 3H), 1.45(s, 3H), 2.5–2.10(m, 3H), 2.50–3.01(m, 9H), 4.11(m, 2H), 4.57(d, 1H), 5.13(s, 2H), 5.65(d, 1H), 6.15(d, 1H), 6.95(d, 1H), 7.05–7.50(m, 12H), 8.60(m, 2H). |
| 17 | 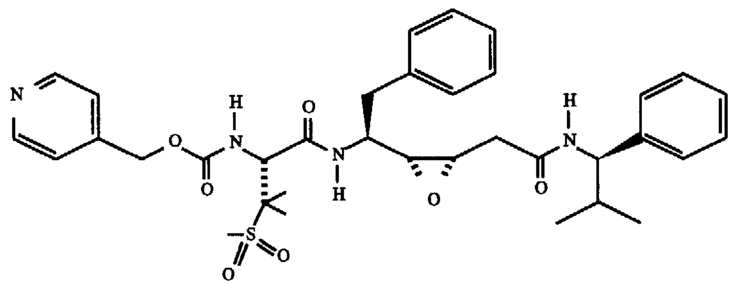 | 665 | 0.75–1.00(m, 6H), 1.50(s, 3H), 1.57(s, 3H), 1.80–2.30(m, 3H), 2.80–3.15(m, 6H), 3.31(m, 1H), 4.15(m, 1H), 4.60(d, 1H), 4.72(m, 1H), 5.12(s, 1H), 5.15(s, 1H), 6.15(d, 1H), 6.37(d, 1H), 6.95(d, 1H), 7.05–7.50(m, 12H), 8.60(m, 2H). |
| 18 | 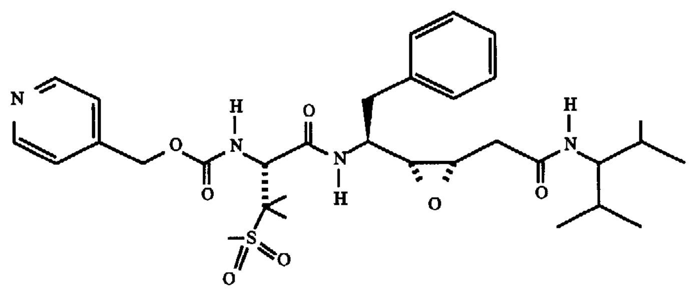 | 631 | 0.80(m, 12H), 1.44(s, 3H), 1.50(s, 3H), 1.71(m, 2H), 1.85–2.20(m, 2H), 2.80–3.15(m, 6H), 3.26(m, 1H), 3.55(m, 1H), 4.05(m, 1H), 4.56(d, 1H), 5.15(s, 2H), 5.60(d, 1H), 6.02(d, 1H), 6.95(d, 1H), 7.05–7.50(m, 7H), 8.61(m, 2H). |

TABLE 2-continued

| # | Structure | MW | NMR |
|---|---|---|---|
| 19 | 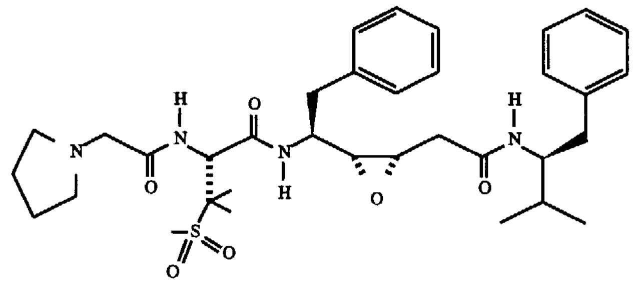 | 645 | 0.90(m, 6H), 1.50–2.10(m, 13H), 2.61–3.33(m, 15H), 4.10(m, 2H), 4.61(d, 1H), 6.01(d, 1H), 6.9(d, 1H), 7.20–7.50(m, 10H), 8.20(d, 1H). |
| 20 | 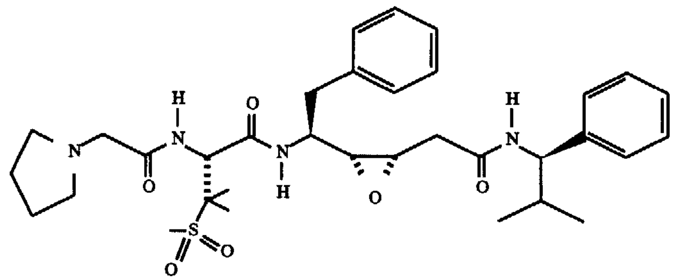 | 631 | 0.91(m, 6H), 1.50–2.12(m, 13H), 2.60–3.30(m, 13H), 4.12(m, 1H), 4.40(m, 6H), 4.61(d, 1H), 6.02(d, 1H), 6.91(d, 1H), 7.20–7.50(m, 10H), 8.31(d, 1H). |
| 21 | 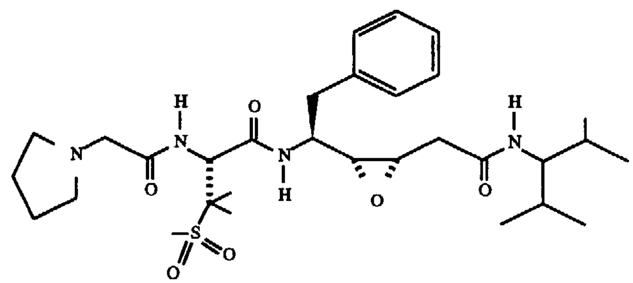 | 597 | 0.91(m, 12H), 1.5–2.1(m, 14H), 4.10(m, 1H), 4.80(d, 1H), 6.01(d, 1H), 6.91(br, 1H), 7.10–7.40(m, 5H), 8.40(d, 1H). |

TABLE 2-continued

| | Structure | | NMR |
|---|---|---|---|
| 22 | (structure) | 586 | 0.80(m, 6H), 1.50(d, 6H), 1.80(m, 1H), 2.12(m, 5H), 2.60–3.40(m, 9H), 4.10(m, 2H), 4.61(d, 1H), 5.60(d, 1H), 6.80(br, 1H), 7.10–7.40(m, 11H). |
| 23 | (structure) | 572 | 0.81(m, 6H), 1.50(d, 6H), 1.82(m, 1H), 2.10(m, 5H), 2.60–3.40(m, 7H), 4.12(m, 1H), 4.31(m, 1H), 4.61(d, 1H), 5.61(br, 1H), 6.80(d, 1H), 7.00–7.40(m, 11H). |
| 24 | (structure) | 538 | 0.85(m, 12H), 1.43(s, 3H), 1.50(s, 3H), 1.77(m, 2H), 1.90–2.20(m, 5H), 2.80–3.15(m, 6H), 3.30(m, 1H), 3.57(m, 1H), 4.15(m, 1H), 4.80(d, 1H), 5.77(d, 1H), 6.85(d, 1H), 7.00(d, 1H), 7.10–7.40(m, 5H). |

TABLE 2-continued

| | | | |
|---|---|---|---|
| 25 | [structure] | 716 | 0.91(d, 6H), 1.60(s, 6H), 1.75(m, 1H), 1.85–2.20(m, 2H), 2.5–3.1(m, 9H), 4.09(m, 2H), 5.12(d, 1H), 5.85(d, 1H), 6.9–7.30(m, 11H), 7.47(t, 1H), 7.60(d, 1H), 7.79(t, 1H), 8.20(d, 1H), 8.40(d, 1H). |
| 26 | [structure] | 702 | 0.80(d, 3H), 0.90(d, 3H), 1.50(s, 6H), 1.95–2.25(m, 3H), 2.80–3.25(m, 7H), 4.10(m, 1H), 4.64(m, 1H), 5.13(d, 1H), 6.47(d, 1H), 7.1–7.30(m, 11H), 7.51(t, 1H), 7.61(d, 1H), 7.79(t, 1H), 8.20(d, 1H), 8.40(d, 1H). |
| 27 | [structure] | 668 | 0.85(d, 12H), 1.50(s, 6H), 1.78(m, 2H), 1.95–2.30(m, 2H), 2.80–3.19(m, 6H), 3.31(m, 1H), 3.55(m, 1H), 4.12(m, 1H), 5.00(d, 1H), 5.55(d, 1H), 7.10–7.30(m, 6H), 7.50(t, 1H), 7.61(d, 1H), 7.79(t, 1H), 8.20(d, 1H), 8.40(d, 1H). |

TABLE 2-continued

| | Structure | MS | NMR |
|---|---|---|---|
| 28 | (structure) | 729 | 0.9(d, 6H), 1.6(s, 6H), 1.7(m, 1H), 1.8–2.2(m, 2H), 2.5–3.1(m, 9H), 4.0(m, 2H), 5.1(d, 1H), 5.5(d, 1H), 6.9–7.3(m, 11H), 7.5–7.7(m, 3H), 8.2(d, 2H), 8.6(br, 1H), 9.2(s, 1H). |
| 29 | (structure) | 715 | 0.8(d, 3H), 0.9(d, 3H), 1.5(s, 6H), 1.9–2.2(m, 3H), 2.8–3.2(m, 7H), 4.1(m, 1H), 4.6(m, 1H), 5.0(d, 1H), 6.4(d, 1H), 7.1–7.3(m, 11H), 7.5–7.7(m, 3H), 8.2(d, 2H), 8.6(br, 1H), 9.3(s, 1H). |
| 30 | (structure) | 681 | 0.9(m, 12H), 1.6(d, 6H), 1.8(m, 2H), 2.1(m, 2H), 2.8–3.1(m, 7H), 3.3(m, 1H), 3.6(m, 1H), 4.8(s, 2H), 5.0(d, 1H), 5.8(br, 1H), 6.9(br, 1H), 7.1–7.4(m, 5H), 7.5–7.7(m, 3H), 8.2(d, d, 2H), 8.6(br, 1H), 9.3(s, 1H). |

TABLE 2-continued

| Comp. No. | Structure | $^1$H NMR (CDCl$_3$) δ, FAB MS (M+1) |
|---|---|---|
| 31 | 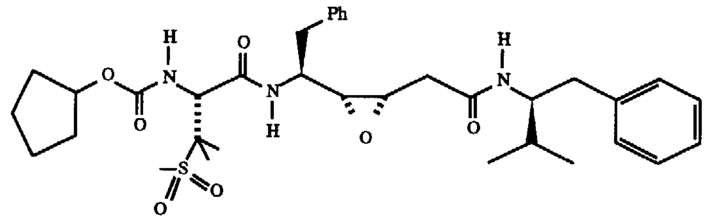 | 0.86–0.95(m, 6H), 1.13–2.22(m, 17H), 2.45–3.47(m, 9H), 4.13(m, 2H), 4.61(d, 1H), 4.91(m, 1H), 6.43(bs, 1H), 7.08–7.42(m, 11H) FAB: 656(M+1) |
| 32 | 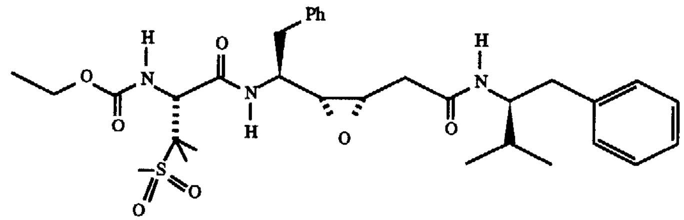 | 0.98(m, 6H), 1.23–2.21(m, 12H), 2.81–3.12(m 9H), 4.12(m, 4H), 4.63(d, 1H), 5.83(bs, 1H), 6.10(bs, 1H), 6.98(bs, 1H), 7.02–7.31(m, 10H). FAB: 615(M+1). |
| 33 | 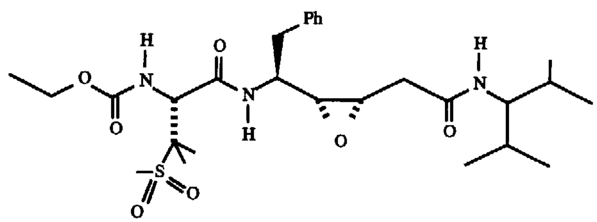 | 1.01(m, 12H), 1.32–2.21(m, 13H), 2.81–3.34 (m, 8H), 4.02(m, 4H) 4.12(m, 1H), 4.62(d, 1H), 5.83(bs, 1H), 6.98(bs, 1H), 7.12–7.29(m, 5H). FAB: 567(M+1). |
| 34 | 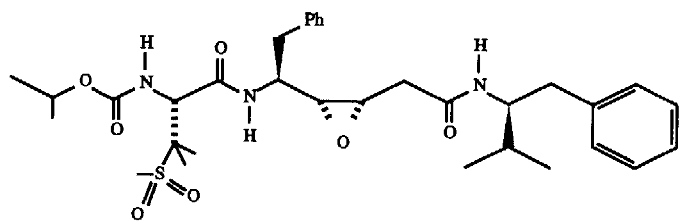 | 0.98(m, 6H), 1.23–2.21(m, 15H), 2.81–3.32(m 9H), 3.98–4.12(m, 2H), 4.73(d, 1H), 4.95(m, 1H), 5.70(bs, 1H), 5.92(bs, 1H), 7.00(bs, 1H), 7.23(m, 10H). FAB: 629(M+1). |

TABLE 2-continued

| # | Structure | NMR/MS |
|---|---|---|
| 35 | (furfuryl carbamate structure) | 0.98(m, 6H), 1.23–2.21(m, 9H), 2.81–3.12(m, 9H), 4.12(m, 2H), 4.63(d, 1H), 5.12(s, 2H), 5.83(bs, 1H), 6.10(bs, 1H), 6.98(bs, 1H), 7.02–7.31(m, 13H). FAB: 667(M+1). |
| 36 | (cyclopropylmethyl carbamate structure) | 0.30(m, 2H), (0.58(m, 2H), 0.97(m, 6H), 1.15(m, 1H), 1.24–2.21(m, 15H), 2.80–3.31(m, 9H), 3.95(m, 2H), 4.10(m, 2H), 4.59(d, 1H), 5.75(d, 1H), 5.92(d, 1H), 6.95(d, 1H), 7.10–7.38(m, 10H) |
| 37 | (cyclopropyl urea structure) | 0.92(m, 9H), 1.21–2.22(m, 10H), 2.64–3.32(m, 14H), 4.02(m, 2H), 4.82(d, 1H), 6.2(bs, 2H), 7.12–7.33(m, 11H) FAB: 657(M+1) |
| 38 | (butyl urea structure) | 0.84(m, 8H), 0.94(m, 2H), 1.41–1.94(m, 9H), 1H), 2.65–2.77(m, 6H), 2.93(m, 1H), 2.97(s, 3H), 3.02(m, 1H), 3.95(m, 1H), 4.83(d, 1H), 6.02(m, 1H), 6.08(d, 1H), 6.21(d, 1H), 7.04–7.21(m, 12H), 1H). FAB: 631(M+1). |

TABLE 2-continued

| | Structure | Data |
|---|---|---|
| 39 | [structure with benzyl urea, sulfone, epoxide, phenylalanine-valine amide] | 0.84(m, 6H), 1.41–1.94(m, 9H), 2.55(m, 1H), 2.77(m, 6H), 2.93(m, 1H), 3.02(m, 1H), 3.98(4.23(m, 2H), 4.83(d, 1H), 6.02(d, 1H), 6.08–6.3H), 7.04–7.21(m, 12H), 7.46(d, 1H). FAB: 66(M+1). |
| 40 | [structure with furfuryl urea, sulfone, epoxide, phenylalanine-valine amide] | 0.84(m, 6H), 1.41–1.94(m, 9H), 2.55(m, 1H), 2.77(m, 6H), 2.93(m, 1H), 3.02(m, 1H), 3.98(4.33(m, 2H), 4.85(d, 1H), 6.02(d, 1H), 6.08–6.3H), 7.04–7.21(m, 14H), 7.41(d, 1H). FAB: 65(M+1). |
| 41 | [structure with thiophene amide, sulfone, epoxide, phenylalanine-valine amide] | 0.89(m, 6H), 1.49–2.05(m, 9H), 2.62(m, 1H), 2.76–3.01(m, 8H), 4.03(m, 2H), 4.98(d, 1H), 5.73 (d, 1H), 7.09–7.56(m, 15H) FAB: 654(M+1) |
| 42 | [structure with furan amide, sulfone, epoxide, phenylalanine-valine amide] | 0.91(m, 6H), 1.52–1.76(m, 8H), 1.94(m, 1H), 2.56–2.98(m, 8H), 3.97(m, 2H), 5.05(d, 1H), 5.72(d, 1H), 6.45(d, 1H), 7.04–7.57(m, 14H). FAB: 638(M+1). |

TABLE 2-continued

| | Structure | Data |
|---|---|---|
| 43 | (pyridin-2-yl structure) | 0.90(m, 6H), 1.52–1.77(m, 8H), 1.94(m, 1H), 2.56–2.98(m, 8H), 3.97(m, 2H), 5.05(d, 1H), 5.92(d, 1H), 6.65(d, 1H), 7.04–7.67(m, 15H). FAB: 649(M+1). |
| 44 | (pyridin-3-yl structure) | 0.90(m, 6H), 1.52–1.79(m, 8H), 1.95(m, 1H), 2.56–2.99(m, 8H), 3.96(m, 2H), 5.05(d, 1H), 5.99(d, 1H), 6.65(d, 1H), 7.04–7.67(m, 15H). FAB: 649(M+1). |
| 45 | (dihydropyranone structure) | 0.87(m, 6H), 1.41–1.58(m, 12H), 1.80(m, 1H), 2.05(m, 1H), 2.50–2.60(m, 4H), 2.75–2.82(m, 7H), 3.92–4.05(m, 2H), 4.82(d, 1H), 6.20(1, 1H), 7.05–7.25(m, 11H). FAB: 696(M+1). |
| 46 | (methoxyacetyl structure) | 0.85–0.98(m, 12H), 1.47(d, 6H), 1.71(m, 1H), 1.83(m, 1H), 2.10–2.12(m, 2H), 2.60(m, 1H), 2.72–3.15(m, 10H), 3.95–4.10(m, 2H), 4.95(d, 1H), 5.93(d, 1H), 6.95 (d, 1H), 7.10–7.35(m, 10H), 7.72(bs, 1H) FAB: 628(M+1) |

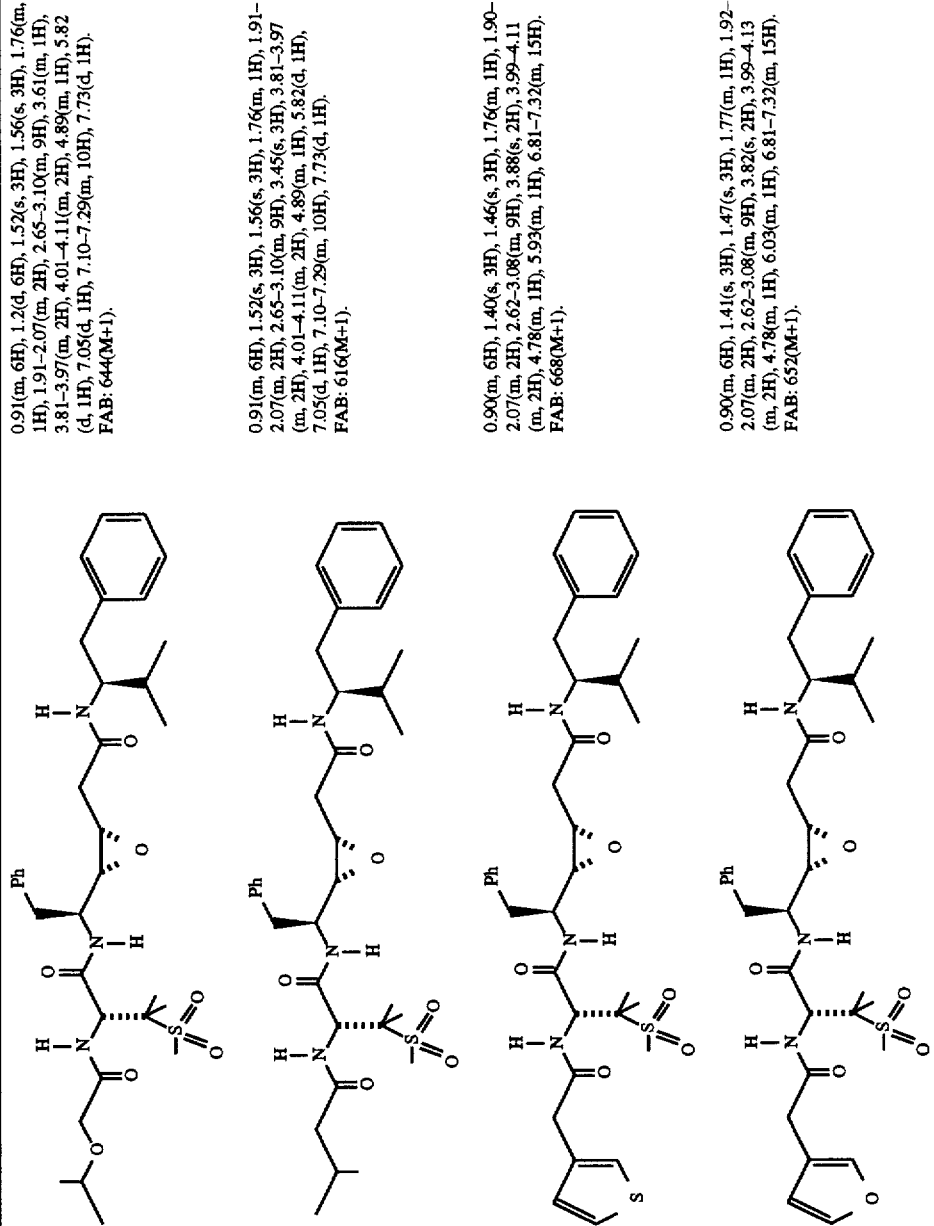

TABLE 2-continued
| | | |
|---|---|---|
| 51 | 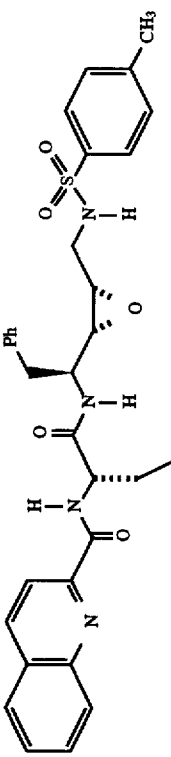 | 2.41(s, 3H), 2.46(m, 2H), 2.65–3.13(m, 8H), 3.89(m, 1H), 5.02(m, 1H), 5.78(d, 1H), 6.19(d, 1H), 6.70(d, 1H), 7.07–8.29(m, 16H), 9.37(d, 1H) FAB: 616(M+1) |
| 52 | 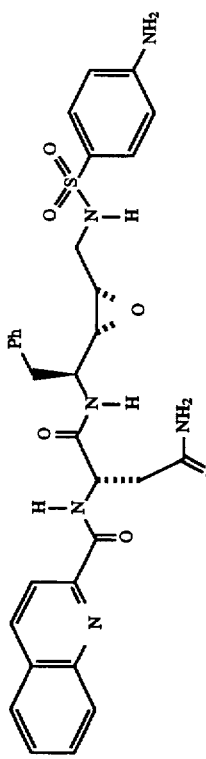 | 2.46(m, 2H), 2.65–3.13(m, 8H), 3.89(m, 1H), 5.02(m, 1H), 5.78(d, 1H), 6.19(d, 1H), 6.70(d, 1H), 6.75(m, 2H), 7.07–8.29(m, 16H), 9.37(d, 1H) |
| 53 | 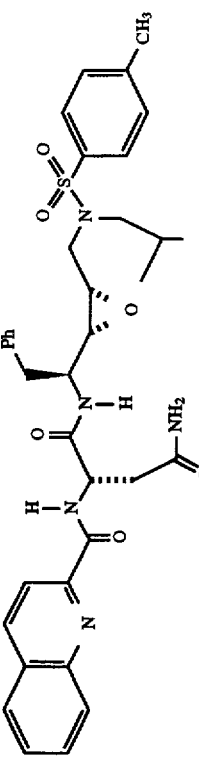 | 0.72–1.05(m, 6H), 2.41(s, 3H), 2.46(m, 2H), 2.58(m, 2H), 2.65–3.13(m, 8H), 3.89(m, 1H), 5.02(m, 1H), 5.78(d, 1H), 6.19(d, 1H), 6.70(d, 1H), 7.07–8.29(m, 16H), 9.37(d, 1H) |

Assay for inhibitory effect on HIV protease

The inhibitory effect on HIV protease of the compounds of the present invention was determined by the following method.

To a buffer solution comprising 50 mM sodium acetate, pH 5.5, 1 mM dithiothreitol(DTT), 1 mM ethylenediaminetetraacetate (EDTA), 0.75M ammonium sulfate, 0.2M sodium chloride and 0.1% NP40 (NONIGET P-40; Sigma Chemical Co., U.S.A.), were added various concentrations of a compound selected from Compound Nos. 1 to 53 to prepare a preincubation solution. Inhibition reaction was started with the addition of 2.6 nM of HIV-1 protease to the preincubation solution. Each 10 µl of the reaction solution was taken at a given time interval and added to 80 µl of assay solution containing 100 µM of reaction substrate in the same buffer solution as the above to assay for the residual enzyme activity. In this context, an oligopeptide($K_M$=20 µM) consisting of 11 amino acids, i.e., Ser-Ile-Ala-Glu-(p-NO$_2$)-Phe-Leu-Val-Arg-Ala-Lys-His, was used as a reaction substrate, which oligopeptide was to be cleaved in two by the breakage of amide bond between (P—NO$_2$)-Phe and Leu upon the attack of HIV protease. The reaction rate was determined by subjecting the substrate before the reaction and the product after the reaction to HPLC separation and then measuring the relative amount of the product, using the strong absorbance of (p—NO$_2$)-Phe at 280 nm. The amounts of reduction in enzyme activity according to the elasped time were measured and the natural logarithmic values(ln) of the measured amounts were plotted against time to obtain a linear graph and $k_{obs}$ was calculated from the slope of the linear graph.

The inhibition constant was calculated according to the following equation:

$$\frac{1}{k_{obs}} = \frac{1}{k_{ina}} + \frac{K_I}{k_{ina}} \cdot \frac{1}{[I]}$$

wherein:

$k_{obs}$ is a rate constant indicating the rate of reduction in enzyme activity according to the elapsed time under the presence of a given concentration of inhibitor, $k_{ina}$ is a rate constant indicating the rate of chemical reaction forming covalent bond between an enzyme and an inhibitor in Michaelis-Menten complex, $K_I$ is an inhibition constant indicating the dissociation rate of Michaelis-Menten complex into an enzyme and an inhibitor, and

[I] means the inhibitor concentration.

The above equation is applicable to an experiment carried out under the condition in which the concentration of inhibitor is far higher than that of enzyme (Steady State Kinetic). In case that the experiment was carried out under the condition in which the concentrations of inhibitor and enzyme were about the same, because of the superior inhibition effect of the inhibitor, the mechanism equation of

(wherein, E means an enzyme, I means an inhibitor, EI means a Michaelis-Menten complex and EI' means a complex having convalent bond formed between an enzyme and an inhibitor; and $K_I$ and $k_{ina}$ have the same meanings as defined above) was used to calculate the relative concentration of active enzyme, i.e., [E]/([E]+[EI]+[EI']) in every given time. The inhibition constants $K_I$ and $k_{ina}$ and second order rate constant $k_{ina}/K_I$ were obtained by inputting the value of [E]/([E]+[EI]+[EI']) into KINSIM/FITSIM program. FIG. 1 exemplifies a result of the experiment determining the binding ratio of enzymes and inhibitors, which result was obtained by reacting the enzyme and the inhibitor in various concentration ratios for a sufficient time period (at least for 30 minutes), and then plotting the relative activity of the remaining enzyme against [conc. of inhibitor]/[conc. of enzyme].

FIG. 1 was obtained using Compound No. 1; however, other compounds of the present invention are believed to yield substantially same results. The stoichiometric ratio of inhibitor to enzyme was 1:1; and this proves that one inhibitor is required to inactivate one enzyme. The above result gives a basis for inputting the said mechanism equations into KINSIM/FITSIM program.

The activity of HIV protease inactivated by an inhibitor of the present invention failed to return or recover even after a vigorous dialysis for 24 hours. The inhibition constants obtained in the above assay are shown in Table 3 below; and the results fully demonstrate that the compounds of the present invention inhibit HIV protease irreversibly.

Determination of anti-viral activity and cytotoxicity

The anti-viral activity of the compounds of the present invention was determined by measuring the concentration of the compounds that inhibits the proliferation of HIV by 50% (IC$_{50}$) through a survey for syncytium formation or reverse transcriptase assay.

1×10$^5$ cells of each of H9(ATCC HTB 176) and Sup T1 cell lines were added to the wells of a 24-well microtiter plate and various concentrations of the Compounds 1 to 30 of the present invention were added thereto. 200 TCID$_{50}$ (200-fold of 50% tissue culture infection dose) of HIV-1 inoculum and rpmi-1640 medium(Sigma Chemical Co., U.S.A) were added successively to the wells and the plate was incubated at 37° C. In case of Sup T1, the number of syncytium formed was investigated after 3 to 9 days. IC$_{50}$ of each compound was determined by measuring the concentration of inhibitor that can reduce the number of syncytium by 50% compared with those formed in the same condition without the inhibitor.

In case of H9, three-quarters(¾) of the culture medium in volume was refreshed every 3 days; and 6 ml of the culture fluid was centrifuged at 1000 rpm for 10 minutes. To 5 ml of the resulting supernatant were added 2.5 ml of 30% polyethyleneglycol(PEG, M.W. 6000–8000) and 0.4M NaCl. The resulting solution was allowed to stand at 0° C. overnight to precipitate virus particles. The solution was centrifuged at 2000 rpm for 45 minutes, the supernatant was discarded therefrom and the precipitate was diluted with 20 µl of a reverse transcriptase suspension buffer(50 mM tris-HCl, pH 7.5, 1 mM dithiothreitol, 20% glycerol, 0.25M KCl and 0.25% Triton X-100). The resulting suspension was stored in an Effendorf tube at −70° C. until used. A procedure of freezing said virus suspension for 2 minutes in dry ice and thawing same at 37° C. for 2 minutes was repeated three times and the resulting suspension was centrifuged at 4° C. The resulting supernatant was used in carrying out the reverse transcriptase assay.

10 µl of the said viral suspension was added to a solution of: 10 µl of buffer solution(250 mM tris-HCl, pH 7.5, 37.5 mM MgCl$_2$, 0.25% triton X-100), 1.2 µl of 200 mM dithiothreitol, 5 µl of 10 µM oligo(dT)-poly(A)(Boeringer Manheim, 12–18 oligomer), 1 µl (1 µCi) of $^3$H-TTP (Thymidinetri-phosphate) and 23.6 µl of water; and the resulting mixture was placed at 37° C. After 1 hour, the mixture was poured onto a WHATMAN DEB1 filter and the filter was washed three times with 5 ml of 2× SSC buffer solution(17.53 g of sodium chloride, 8.82 g of sodium citrate, pH 7.0, 1 liter of water) for about 10 minutes each time and twice with 95% ethanol for 10 seconds. The filter was put onto aluminum foil and dried with an infra-red lamp. The amount of radioactivity was counted using a liquid scintillation counter. $IC_{50}$ of each compound was determined by measuring the concentration of inhibitor that can reduce the activity of reverse transcriptase by 50%.

To determine the cytotoxicity of the compounds of the present invention, 0.1 μM to 100 μM of the Compounds 1 to 30 were added to H9 cell or Sup T1 cell and the mixture was cultivated on a rpmi-1640 medium at 37° C. The medium was refreshed every 3 days and the extent of cell proliferation was observed using Hemacytometer according to the trypan blue dye exclusion technique which is well known in the art. $CT_{50}$(i.e., concentration that causes death of cells by 50%) was determined. For reference, AZT(Burrows-Wellcome), A-75925 (Abbott, $C_2$ symmetric compound) and Ro-31-8959(F. Hofmann-La Roche) were used as control compounds.

Then, the anti-viral activity of Compound Nos. 31 to 53 of the present invention was determined by the procedures as described below.

HIV-1 was cultured as follows: COS cell line, which is African monkey's kidney cell transformed with Simian virus 40, was cultured in Dulbecco's modified Eagle's medium (DMEM) and 1 ml ($10^7$ cells) of the culture fluid was mixed with 20 μg of plasmid pNL 4-3 containing HIV-1 gene in an electroporation vessel. The mixture was then electroporated in rpmi medium containing 20% FBS(fetal bovine serum) using cell-porator(BRL) at 800 μF and 250V. The electroporated cells were allowed to stand in ice for 10 minutes, then added to 15 ml of DMEM containing 10% FBS in T75 flaskand and incubated in the presence of $CO_2$. After 24 hours, the culture medium refreshed with 10 ml of the same medium and on the 2nd day, the collected culture fluid was centrifuged. The resulting supernatant was passed through a 0.22 mm filter and the filtrate was placed at −70° C. Thereafter, the HIV-1 cells were amplified by infecting MT-2 cell line therewith. That is, $4\times10_6$ cells of MT-2 cell line were infected with 1500 $TCID_{50}$ of NL 43 virus and on the 7th day, when the syncytium formation was prosperous, 5 fold of uninfected MT-2 cells were added thereto. Two days later, the culture fluid was collected for 3 days and the collected fluid was centrifuged. The resulting supernatant was passed through a 0.22 mm filter and the filtrate was placed at −70° C. Thus obtained HIV-1 contained 131 ng/ml of p24 and exhibited $4\times10^4$ of $TCID_{50}$ and $3.8\times10^5$ cpm/ml of reverse transcriptase activity.

On the other hand, PBMC(peripheral blood mononuclear cells) was isolated from the blood which was obtained from Daejeon Blood Bank in Korea by using Ficoll-Hypaque (Pharmacia) and cultivated in rpmi-1640 medium containing 20% FBS, IL-2(20 Units/ml), penicilline(100 Units/ml), streptomycin (100 μg/ml) and amphotericin B(0.25 μg/ml) in the presence of 5 μg/ml of PHA-P(Sigma Chemical Co.). 3 days later, after being washed with rpmi medium, $1.2\times10^7$ cells were mixed with 12,000 $TCID_{50}$ of HIV-1 at 37° C. for 2 hours. After centrifuging the mixture, the resulting supernatant was washed twice with rpmi medium and the number of cell was adjusted to $2\times10^6$ cells/ml. Then, 200 μl of each of 200, 63.2, 20, 6.32, 3.56, 2, 0.632, 0.2, 0.0632 and 0 μM solution of the Compound Nos. 31 to 53 of the present invention in DMSO was prepared. 495 μl of rpmi-1640 were added to the wells of a 24-well microtiter plate, and 5 μl of each of the present compound and 500 μl($1\times10^6$ cells) of the cells infected with HIV-1 were added successively thereto. Therefore, the final concentration of each compound in the solution was 1000, 316, 100, 31.6, 17.78, 10, 3.16, 1, 0.31 and 0 nM, respectively. The plate was incubated at 37° C. After 4 days, 750 μl of the culture medium was discarded and 1 ml of the same medium containing each compound of the present invention was added to the wells. After 7 days, $IC_{50}$ of each compound was determined by measuring the amount of p24 or the activity of the reverse transcriptase.

The amount of p24 was measured by employing HIV-1 p24 Core Profile ELISA(NEN Cat # NEK-060, Du Pont) or Retro-tekTM HIV-1 p24 antigen ELISA (CPI Cat #0801111, Cellular Products Inc.).

The reverse transcriptase activity was measured as follows: 800 μl of the culture fluid was mixed with 400 μl of 30% polyethyleneglycol(PEG, M.W. 8000, 0.4M NaCl) and the mixture was placed at 4° C. overnight to precipitate virus particles. The solution was centrifuged in Effendorf centrifuger at 15000 rpm for 20 minutes, and the precipitate of virus cells was diluted with 40 μl of buffer 1(25 mM tris-HCl, pH 7.8, 0.25 mM EDTA, 0.025% triton X-100, 50% glycerol, 10 mM DTT and 100 mM KCl) and 20 μl of buffer 2(0.9% triton X-100 and 43.7 mM KCl). 10 μl of the resulting viral suspension was mixed with 90 ml of a buffer solution[46.5 mM tris-HCl, pH 7.8, 8.89 mM DTT, 11.1 mM $MgCl_2$, 3.75 mM NaCl, 2.5 μCi 3H-TTP(NEN-Du Pont, 10–25 Ci/mmol), 0.556 μ/ml poly(rA): oligo(dT) (Pharmacia)] and the mixture was reacted for 1 hour at 37° C. The reaction was quenched with 9 μl of 0.25M EDTA and the mixture was poured onto a WHATMAN DEAE filter(DE 81, Whatmann Cat #3658N323) and the filter was dried and washed with 5 ml of 2× SSC buffer solution. The filter was put onto aluminum foil and dried with an intra-red lamp. The amount of radioactivity was counted using a liquid scintillation counter with addition of 5 ml of liquid scintillation solution.

To determine the cytotoxicity of the compounds 31 to 53 of the present invention, $1\times10^6$ PBMC, which is activated with PHA-P, and 0.1 μM to 100 μM of the compounds were added to the wells of a 24-well microtiter plate and the plate was incubated on rpmi-1640 medium at 37° C. The medium was refreshed every 4 days, and the extent of cell proliferation was observed and $CT_{50}$ was determined as described in the above.

Table 3 shows the anti-viral activities($IC_{50}$) and cytotoxicities ($CT_{50}$) of the tested compounds of the present invention and the above control compounds.

TABLE 3

| Comp.No. | $k_{inf}/K_i(min^{-1}M^{-1})$* | $IC_{50}$(nM) | $CT_{50}$(nM) |
|---|---|---|---|
| 1 | $10^9 - 10^{10}$ | 25 | >100,000 |
| 2 | $10^9 - 10^{10}$ | 30 | >100,000 |
| 3 | $10^9 - 10^{10}$ | 10 | >100,000 |
| 4 | $10^9 - 10^{10}$ | 1 | >100,000 |
| 5 | $10^9 - 10^{10}$ | 5 | >100,000 |
| 6 | $10^9 - 10^{10}$ | 5 | >100,000 |
| 7 | $10^9 - 10^{10}$ | 20 | >100,000 |
| 8 | $10^9 - 10^{10}$ | 10 | >100,000 |
| 9 | $10^9 - 10^{10}$ | 8 | >100,000 |
| 10 | $10^9 - 10^{10}$ | 12 | >100,000 |
| 11 | $10^9 - 10^{10}$ | 15 | >100,000 |
| 12 | $10^9 - 10^{10}$ | 50 | >100,000 |
| 13 | $10^9 - 10^{10}$ | 10 | >100,000 |
| 14 | $10^9 - 10^{10}$ | 15 | >100,000 |
| 15 | $5.0 \times 10^8$ | 18 | >100,000 |
| 16 | $10^9 - 10^{10}$ | 50 | >100,000 |
| 17 | $10^9 - 10^{10}$ | 35 | >100,000 |
| 18 | $3.5 \times 10^7$ | 40 | >100,000 |
| 19 | $2.5 \times 10^8$ | 100 | >100,000 |
| 20 | $5.0 \times 10^7$ | 150 | >100,000 |

TABLE 3-continued

| Comp.No. | $k_{inc}/K_i(min^{-1}M^{-1})$* | $IC_{50}(nM)$ | $CT_{50}(nM)$ |
|---|---|---|---|
| 21 | $2.4 \times 10^7$ | 140 | >100,000 |
| 22 | $5.0 \times 10^8$ | 200 | >100,000 |
| 23 | $5.0 \times 10^8$ | 250 | >100,000 |
| 24 | $2.0 \times 10^7$ | 300 | >100,000 |
| 25 | $10^9 - 10^{10}$ | 20 | >100,000 |
| 26 | $10^9 - 10^{10}$ | 17 | >100,000 |
| 27 | $10^9 - 10^{10}$ | 10 | >100,000 |
| 28 | $10^9 - 10^{10}$ | 8 | >100,000 |
| 29 | $10^9 - 10^{10}$ | 10 | >100,000 |
| 30 | $10^9 - 10^{10}$ | 14 | >100,000 |
| 31 | $1.88 \times 10^8$ | 169 | >10,000 |
| 32 | $<0.54 \times 10^7$ | >1000 | >10,000 |
| 33 | $3.1 \times 10^9$ | 23 | >10,000 |
| 34 | $1.3 \times 10^7$ | N.D. | >10,000 |
| 35 | $>3.5 \times 10^9$ | 54 | >10,000 |
| 36 | $2.0 \times 10^9$ | 25 | >10,000 |
| 37 | $<2.9 \times 10^6$ | N.D. | >10,000 |
| 38 | $2.9 \times 10^7$ | 523 | >10,000 |
| 39 | $>3.0 \times 10^9$ | 325 | >10,000 |
| 40 | $>3.1 \times 10^9$ | 457 | >10,000 |
| 41 | $>3.2 \times 10^9$ | 7.5 | >10,000 |
| 42 | $1.8 \times 10^8$ | 180 | >10,000 |
| 43 | $>3.0 \times 10^9$ | 10 | >10,000 |
| 44 | $>3.3 \times 10^9$ | 15 | >10,000 |
| 45 | $2.8 \times 10^9$ | 39 | >10,000 |
| 46 | $0.9 \times 10^7$ | 426 | >10,000 |
| 47 | $2.8 \times 10^6$ | >1000 | >10,000 |
| 48 | $0.8 \times 10^7$ | 550 | >10,000 |
| 49 | $3.3 \times 10^9$ | 125 | >10,000 |
| 50 | $0.9 \times 10^7$ | 327 | >10,000 |
| 51 | $2.3 \times 10^7$ | 670 | >10,000 |
| 52 | $0.3 \times 10^7$ | 750 | >10,000 |
| 53 | $<0.3 \times 10^5$ | >2000 | >10,000 |
| AZT | | 30 | >10,000 |
| A-75925 | | 100 | >10,000 |
| RO-31-8959 | | 25 | >10,000 |

N.D.: not determined
*If the value of $k_{inc}/K_i$ is greater than $10^9$, it is limited to calculate the precise numerical value in accordance with KINSIM/FITSIM(see, Williams, J. W. and Morrison, J. F., Methods. Enzymol., 63, 437-466(1979); and Zimmerle, C. T. and Frieden, C., Biochem. J., 258, 381-387(1989)).

As can be seen from the above results, the compounds of the present invention are superior HIV protease inhibitors having a higher inhibition effect and lower cytotoxicity than those of the prior art.

While the present invention has been shown and described with reference to the particular embodiments, it will be apparent to those skilled in the art that many changes and modifications may be made without departing from the spirit and scope of the invention as defined in the appended claims.

What is claimed is:

1. A cis-epoxide compound of formula (I) and the pharmacologically acceptable salts, hydrates and solvates thereof:

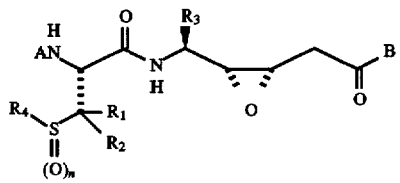

wherein:

$R_1$ and $R_2$ are independently a hydrogen or a lower alkyl group;

$R_3$ is an aryl group or a lower alkyl group optionally substituted with an aromatic or $C_3-C_8$ cyclic alkyl radical;

$R_4$ is a hydrogen or a $C_1-C_4$ alkyl group;

n is 0, 1 or 2;

A is a group of the formula $(X)(Y)_mR_5$ (wherein X is —CO—, —COCO—, —SO—, —SO$_2$— or —CS; Y is —O—, —CH$_2$—, —NH— or —NCH$_3$—; m is 0 or 1; and $R_5$ is a heterocycle, a straight, branched or cyclic $C_1-C_8$ alkyl radical, or a lower alkyl radical substituted with a heterocycle or cyclic alkyl substituent, a straight, branched or cyclic $C_1-C_8$ alkoxy radical, or an aryl-substituted lower alkoxy radical), or a group of the formula $NR_6R_7$(wherein $R_6$ is a straight or branched $C_1-C_8$ alkyl radical, or a cyclic alkyl radical, or a lower alkyl radical substituted with a cyclic alkyl substituent; and $R_7$ is a hydrogen or a lower alkyl radical ); and B is a group of the formula

(wherein Z is O, NH or NCH$_3$; and $R_8$ and $R_9$ are independently a lower alkyl radical optionally substituted with an aromatic hydrocarbon or cyclic alkyl substituent, or a $C_3-C_8$ cyclic alkyl radical, or an aromatic radical).

2. The cis-epoxide compound of claim 1, which has the following formula(I-1):

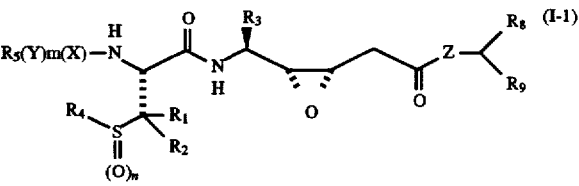

wherein:

$R_1$ and $R_2$ are independently a hydrogen, or a methyl or ethyl group;

$R_3$ is an isobutyl, cyclopentylmethyl, cyclohexylmethyl, benzyl or phenyl group;

$R_4$ is a hydorogen, or a methyl or ethyl group;

$R_5$ is a cyclohexylmethyl, benzyl, quinolinyl, tetrahydroquinolinyl, isoquinolinyl, indolyl, pyridyl, pyridylmethyl, isoquinolinyloxymethyl, naphtoxymethyl, tetrahydropyranyl, benzopyranyl or 4-oxo-4H-1-benzopyranyl group;

$R_8$ and $R_9$ are independently an isopropyl, isobutyl, isopentyl, benzyl, cyclopropyl, cyclobutyl, cyclopentyl, cyclopropylmethyl or phenyl group; and X, Y, Z, m and n have the same meanings as defined in claim 1.

3. The cis-epoxide compound of claim 1, which has the following formula (I-2):

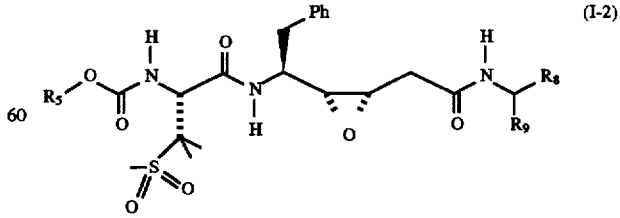

wherein:

$R_5$ is a straight or branched $C_1-C_8$ alkyl group, a lower alkyl group substituted with a heterocycle or cyclic alkyl radical, or a cyclic alkyl group; and R₈ and R₉ have the same meanings as defined in claim 1.

4. The cis-epoxide compound of claim 3, wherein R₅ is an isopropyl or cyclopropylmethyl group; R₈ is an isopropyl group; and R₉ is a benzyl group.

5. The cis-epoxide compound of claim 1, which has the following formula (I-3):

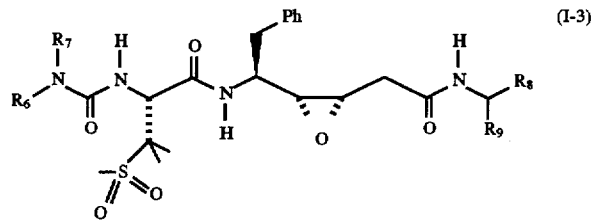

wherein:

R₆ is a straight or branched C₁-C₈ alkyl group, a cyclic alkyl group or a lower alkyl group substituted with a cyclic alkyl radical;

R₇ is a hydrogen or a lower alkyl group; and R₈ and R₉ have the same meanings as defined in claim 1.

6. The cis-epoxide compound of claim 5, wherein R₆ is a 2-furanylmethyl or benzyl group; R₇ is a benzyl group; R₈ is a hydrogen or a methyl group; and R₉ is an isopropyl group.

7. The cis-epoxide compound of claim 1, which has the following formula (I-4):

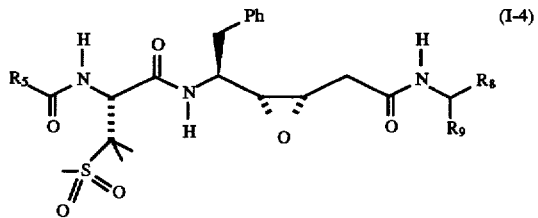

wherein:

R₅ is a cyclic C₁-C₈ alkyl group, or a heterocycle; and R₈ and R₉ have the same meanings as defined in claim 1.

8. The cis-epoxide compound of claim 7, wherein R₅ is a 2-thiopene, 2-furanyl or 4-oxo-2,3-dihydro-6,6-diphenylpirane group; R₈ is an isopropyl group; and R₉ is a benzyl group.

9. The cis-epoxide compound of claim 1, which has the following formula (I-5):

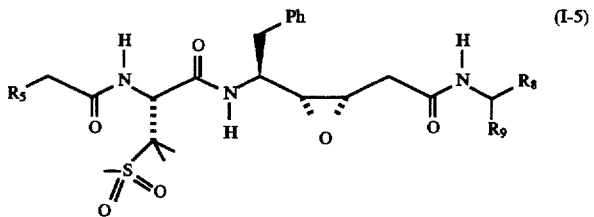

wherein:

R₅ is a straight, branched or cyclic C₁-C₈ alkyl group, a straight, branched or cyclic C₁-C₈ alkoxy group, an aryl-substituted lower alkoxy group, or a heterocycle; and R₈ and R₉ have the same meanings as defined in claim 1.

10. The cis-epoxide compound of claim 9, wherein R₅ is 3-thiopene; R₈ is an isopropyl group; and R₉ is a benzyl group.

11. The cis-epoixide compound of claim 1, which is selected from the group consisting of:

[(5S)-[N-(2-quinolinecarbonyl) -β-methanesulfonyl-L-alaninyl]amino]-(4R, 3S)-epoxy-6-phenyl-hexanoyl]-[(2S)-(1-phenyl-3-methyl)butyl]amide;

[(5S )-[N-(2-quinolinecarbonyl)-β-methanesulfonyl-L-alaninyl]amino]-(4R, 3S)-epoxy-6-phenyl-hexanoyl]-[(1R)-(1-phenyl-2 -methyl)propyl]amide;

[(5S)-[N-(2-quinolinecarbonyl)-β-methanesulfonyl-L-alaninyl]amino]-(4R,3S)-epoxy-6-phenyl-hexanoyl]-[di(isopropyl)methyl]amide;

[(5S)-[N-benzyloxycarbonyl-β-methanesulfonyl-L-valinyl]amino]-(4R,3S)-epoxy-6-phenyl-hexanoyl]-[(2S)-(1-phenyl-3-methyl)butyl]amide;

[(5S)-[N-benzyloxycarbonyl-β-methanesulfonyl-L-valinyl]amino]-(4R,3S)-epoxy-6-phenyl-hexanoyl]-[(1R)-(1-phenyl-2-methyl)propyl]amide;

[(5S)-[N-benzyloxycarbonyl-β-methanesulfonyl-L-valinyl]amino]-(4R,3S)-epoxy-6 -phenyl-hexanoyl]-[di(isopropyl)methyl]amide;

[(5S)-[N-(2-quinolinecarbonyl)-β-methanesulfonyl-L-valinyl]amino]-(4R,3S)-epoxy-6-phenyl-hexanoyl]-[(2S)-(1-phenyl-3 -methyl)butyl]amide;

[(5S)-[N-(2-quinolinecarbonyl)-β-methanesulfonyl-L-valinyl]amino]-(4R,3S)-epoxy-6-phenyl-hexanoyl]-[(1R)-(1-phenyl1-2-methyl) propyl]amide;

[(5S)-[N-(2-quinolinecarbonyl)-β-methanesulfonyl-L-valinyl]amino]-(4R,3 S)-epoxy-6-phenyl-hexanoyl]-[di(isopropyl)methyl ]amide;

[(5S)-[N-(2-pyridylmethoxy)carbonyl-β-methanesulfonyl-L-valinyl]amino]-(4R,3S)-epoxy-6-phenyl-hexanoyl]-[(2S)-(1-phenyl-3-methyl)butyl]amide;

[(5S)-[N-(2-pyridylmethoxy)carbonyl-β-methanesulfonyl-L-valinyl]amino]-(4R,3S)-epoxy-6-phenyl-hexanoyl]-[(1R)-(1-phenyl-3-methyl)propyl]amide;

[(5S)-[N-(2-pyridylmethoxy)carbonyl-β-methanesulfonyl-L-valinyl]amino]-(4R,3S)-epoxy-6-phenyl-hexanoyl]-[di(isopropyl)methyl]amide;

[(5S)-[N-(3-pyridylmethoxy)carbonyl-β-methanesulfonyl-L-valinyl]amino]-(4R,3S)-epoxy-6-phenyl-hexanoyl]-[(2S)-(1-phenyl-3-methyl)butyl]amide;

[(5S)-[N-(3-pyridylmethoxy)carbonyl-β-methanesulfonyl-L-valinyl]amino]-(4R,3S)-epoxy-6-phenyl-hexanoyl]-[(1R)-(1-phenyl-3-methyl)propyl]amide;

[(5S)-[N-(3-pyridylmethoxy)carbonyl-β-methanesulfonyl-L-valinyl]amino]-(4R,3S)-epoxy-6-phenyl-hexanoyl]-[di(isopropyl)methyl]amide;

[(5S)-[N-(4-pyridylmethoxy)carbonyl-β-methanesulfonyl-L-valinyl]amino]-(4R,3S)-epoxy-6-phenyl-hexanoyl]-[(2S)-(1-phenyl-3-methyl)butyl]amide;

[(5S)-[N-(4-pyridylmethoxy)carbonyl-β-methanesulfonyl-L-valinyl]amino]-(4R,3S)-epoxy-6-phenyl-hexanoyl]-[(1R)-(1-phenyl-3-methyl)propyl]amide;

[(5S)-[N-(4-pyridylmethoxy)carbonyl-β-methanesulfonyl-L-valinyl]amino]-(4R,3S)-epoxy-6-phenyl-hexanoyl]-[di(isopropyl)methyl]amide;

[(5S)-[(N-(1-quinolydine)acetyl-β-methanesulfonyl-L-valinyl]amino]-(4R,3S)-epoxy-6-phenyl-hexanoyl]-[(2S)-(1-phenyl-3-methyl)butyl]amide;

[(5S)-[(N-(1-quinolydine)acetyl-β-methanesulfonyl-L-valinyl]amino]-(4R,3S)-epoxy-6-phenyl-hexanoyl]-[(1R)-(1-phenyl-2-methyl)propyl]amide;

[(5S)-[(N-(1-quinolydine)acetyl-β-methanesulfonyl-L-valinyl]amino]-(4R,3S)-epoxy-6-phenyl-hexanoyl]-[di(isopropyl)methyl]amide;

[(5S)-[(N-acetyl)-β-methanesulfonyl-L-valinyl]amino]-(4R,3S)- epoxy-6-phenyl-hexanoyl]-[(2S)-(1-phenyl-3-methyl)butyl]amide;

[(5S)-[(N-acetyl)-β-methanesulfonyl-L-valinyl]amino]-(4R,3S)-epoxy-6-phenyl-hexanoyl]-[(1R)-(1-phenyl-2-methyl)propyl]amide;

[(5S)-[(N-acetyl)-β-methanesulfonyl-L-valinyl]amino]-(4R,3S)-epoxy-6-phenyl-hexanoyl]-[di(isopropyl)methyl]amide;

[(5S)-[N-(4-oxo-4H-1-benzopyran-2-carbonyl)-β-methanesulfonyl-L-valinyl]amino]-(4R,3S)-epoxy-6-phenyl-hexanoyl]-[(2S)-(1-phenyl-3-methyl)butyl]amide;

[(5S)-[N-(4-oxo-4H-1-benzopyran-2-carbonyl)-β-methanesulfonyl-L-valinyl]amino]-(4R,3S)-epoxy-6-phenyl-hexanoyl]-[(1R)-(1-phenyl-3-methyl)propyl]amide;

[(5S)-[N-(4-oxo-4H-1-benzopyran-2-carbonyl)-β-methanesulfonyl-L-valinyl]amino]-(4R,3S)-epoxy-6-phenyl-hexanoyl]-[di(isopropyl)methyl]amide;

[(5S)-[(N-(5-isoquinolinyloxy) acetyl-β-methanesulfonyl-L-valinyl]amino]-(4R,3S)-epoxy-6-phenyl-hexanoyl]-[di(isopropyl)methyl]amide;

[(5S)-[(N-(5-isoquinolinyloxy)acetyl-β-methanesulfonyl-L-valinyl]amino]-(4R,3S)-epoxy-6-phenyl-hexanoyl]-[(1R)-(1-phenyl-2-methyl)propyl]amide;

[(5S)-[(N-(5-isoquinolinyloxy)acetyl-β-methanesulfonyl-L-valinyl]amino]-(4R,3S)-epoxy-6-phenyl-hexanoyl]-[(2S)-(1-phenyl-3-methyl)butyl]amide;

[(5S)-[[(N-ethyloxycarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-ethyloxycarbonyl)-β-methanesulfonyl-L-valinyl]amino]-(4R,3S)-epoxy-6-phenyl-1-hexanoyl]-[di(isopropyl)methyl)butyl]amide;

[(5S)-[[(N-isopropyloxycarbonyl)-β-methanesulfonyl-L-valinyl valinyl]amino]-(4R,3S)-epoxy-6-phenyl-3-methyl)butyl]amide;

[(5S)-[[(N-cyclopentyloxycarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-2-furanyloxycarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-cyclopropylmethyloxycarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[[(N,N-cyclopropylmethyl)aminocarbonyl]-β-methanesulfonyl-L-valinyl]amino]-(4R,3S)-epoxy-6-phenyl-1-hexanoyl]-[(2S) -(1-phenyl-3-methyl)butyl]amide;

[(5S)-[[[(N,N-methylbutyl)aminocarbonyl]-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-benzylaminocarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-2-furanylmethylaminocarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-2-thiophenecarbonyl) -β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-2-furanecarbonyl)-β-methanesulfonyl-L-valinyl]amino]-(4R, 3S)-epoxy-6-phenyl-1-hexanoyl]-[(2S)-(1-phenyl-3-methyl)butyl]amide;

[(5S)-[[(N-2-pyridinecarbonyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-3-pyridinecarbonyl)-S-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-2-(4-oxo-2,3-dihydro-6,6-dimethylpyran)carbonyl]-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-methoxyacetyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-isopropyloxyacetyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-isovaleroyl)-β-methanesulfonyl-L-valinyl]amino]-(4R,3S)-epoxy-6-phenyl-1-hexanoyl]-[(2S)-(1-phenyl-3-methyl)butyl]amide;

[(5S)-[[(N-3-thiopheneacetyl)-β-methanesulfonyl-L-valinyl]amino]-(4R,3S)-epoxy-6-phenyl-1-hexanoyl]-[(2S)-(1-phenyl-3-methyl)butyl]amide; and

[(5S)-[[(N-3-furanacetyl)-β-methanesulfonyl-L-valinyl]amino]-(4R,3S)-epoxy-6-phenyl-1-hexanoyl]-[(2S)-(1-phenyl-3-methyl)butyl]amide.

12. A process for preparing a compound of formula(I) which comprises:

coupling the compound of formula(III) with the compound of formula(IV);

epoxidizing the resulting compound to give the compound of formula(V);

removing the protecting group from the compound of formula(V) to give the compound of formula(VI);

coupling the compound of formula(VI) with the compound of formula(VII);

oxidizing the resulting compound to give the compound of formula(VIII);

deprotecting the compound of formula(VIII) to give the compound of formula(IX); and coupling the compound of formula(IX) with the compound of formula(X) or (XI)

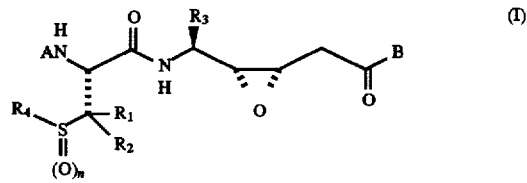

(I)

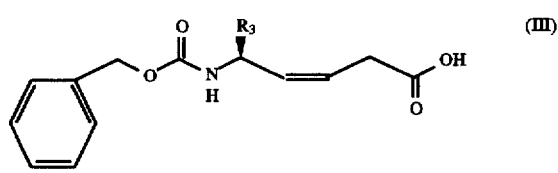

(III)

(IV)

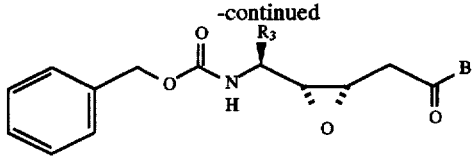 (V)
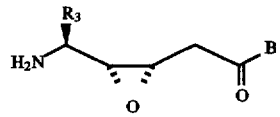 (VI)
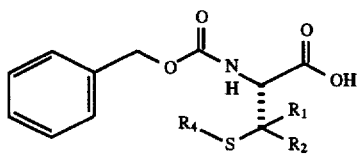 (VII)
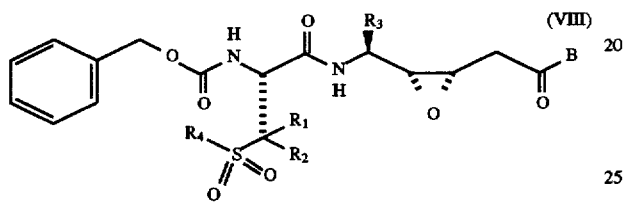 (VIII)
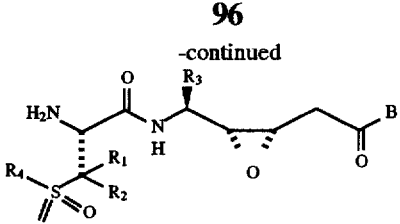 (IX)
A—OH (X)
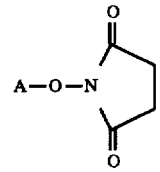 (XI)
wherein A, B and $R_1$ to $R_4$ have the same meanings as defined in claim 1.
13. A pharmaceutical composition comprising, a therapeutically effective amount of the cis-epoxide compound of claim 1 and a pharmaceutically acceptable carrier.
14. The composition of claim 13 further comprising an anti-AIDS agent or immunomodulator.
* * * * *